United States Patent [19]
Bischoff et al.

[11] Patent Number: 5,756,669
[45] Date of Patent: May 26, 1998

[54] P53-BINDING POLYPEPTIDES AND POLYNUCLEOTIDES ENCODING SAME

[75] Inventors: James R. Bischoff, Kensington; Lelia Wu, San Francisco, both of Calif.

[73] Assignee: Onyx Pharmaceuticals, Inc., Richmond, Calif.

[21] Appl. No.: 399,696

[22] Filed: Mar. 2, 1995

Related U.S. Application Data

[63] Continuation-in-part of Ser. No. 156,571, Nov. 22, 1993, abandoned.
[51] Int. Cl.⁶ .................... C07K 14/47; C12N 15/12; C12N 15/64
[52] U.S. Cl. .................... 530/350; 536/23.5; 435/69.1
[58] Field of Search ................. 530/350, 358; 536/23.5, 24.3, 24.31; 435/69.1, 91.2, 255.1

[56] References Cited

PUBLICATIONS

Iwabuchi, K et al. Proc. Natl. Acad. Sci USA vol 91 pp. 6098–6102 Jun., 1994.

*Primary Examiner*—Stephen Walsh
*Assistant Examiner*—Daryl A. Basham
*Attorney, Agent, or Firm*—Gregory J. Giotta; Nina M. Ashton, Esq.

[57] ABSTRACT

The invention provides mammalian polypeptides which bind wild-type and/or mutant mamalian p53 proteins, polynucleotides encoding such polypeptides, screening assays for drug development employing such polypeptides and polynucleotides, immunological and other reagents for diagnostic, therapeutic, and research applications.

15 Claims, 8 Drawing Sheets

```
    GGCACGAGGCGGACAGTGCGGAACTAAAGCAAATGGTTATGAGCCTTAGAGTTTCTGAAC
  1 ---------+---------+---------+---------+---------+---------+ 60
    CCGTGCTCCGCCTGTCACGCCTTGATTTCGTTTACCAATACTCGGAATCTCAAAGACTTG

TCCAAGTACTGTTGGGCTACGCGGGAGAAACAAGCACGGACGCAAACACGAACTTCTCAC
 61 ---------+---------+---------+---------+---------+---------+ 120
    AGGTTCATGACAACCCGATGCGCCCTCTTTGTTCGTGCCTGCGTTTGTGCTTGAAGAGTG

AAAAGCCCTGCATTTGCTAAAGGCTGGCTGTAGTCCTGCTGTGCAAATGAAAATTAAGGA
121 ---------+---------+---------+---------+---------+---------+ 180
    TTTTCGGGACGTAAACGATTTCCGACCGACATCAGGACGACACGTTTACTTTTAATTCCT
                                                      M  K  I  K  E

ACTCTATAGGCGGCGGTTCCCACAGAAAATCATGACGCCTGCAGACTTGTCCATCCCCAA
181 ---------+---------+---------+---------+---------+---------+ 240
    TGAGATATCCGCCGCCAAGGGTGTCTTTTAGTACTGCGGACGTCTGAACAGGTAGGGGTT
     L  Y  R  R  R  F  P  Q  K  I  M  T  P  A  D  L  S  I  P  N

CGTACATTCAAGTCCTATGCCAGCAACTTTGTCTCCATCTACCATTCCACAACTCACTTA
241 ---------+---------+---------+---------+---------+---------+ 300
    GCATGTAAGTTCAGGATACGGTCGTTGAAACAGAGGTAGATGGTAAGGTGTTGAGTGAAT
     V  H  S  S  P  M  P  A  T  L  S  P  S  T  I  P  Q  L  T  Y

CGATGGTCACCCTGCATCATCGCCATTACTCCCTGTTTCTCTTCTGGGACCTAAACATGA
301 ---------+---------+---------+---------+---------+---------+ 360
    GCTACCAGTGGGACGTAGTAGCGGTAATGAGGGACAAAGAGAAGACCCTGGATTTGTACT
     D  G  H  P  A  S  S  P  L  L  P  V  S  L  L  G  P  K  H  E

ACTGGAACTCCCACATCTTACATCAGCTCTTCACCCAGTCCATCCGGATATAAAACTTCA
361 ---------+---------+---------+---------+---------+---------+ 420
    TGACCTTGAGGGTGTAGAATGTAGTCGAGAAGTGGGTCAGGTAGGCCTATATTTTGAAGT
     L  E  L  P  H  L  T  S  A  L  H  P  V  H  P  D  I  K  L  Q

AAAATTACCATTTTATGATTTACTGGATGAACTGATAAAACCCACCAGTCTAGCATCAGA
421 ---------+---------+---------+---------+---------+---------+ 480
    TTTTAATGGTAAAATACTAAATGACCTACTTGACTATTTTGGGTGGTCAGATCGTAGTCT
     K  L  P  F  Y  D  L  L  D  E  L  I  K  P  T  S  L  A  S  D

CAACAGTCAGCGCTTTCGAGAAACCTGTTTTGCATTTGCCTTGACACCACAACAAGTGCA
481 ---------+---------+---------+---------+---------+---------+ 540
    GTTGTCAGTCGCGAAAGCTCTTTGGACAAAACGTAAACGGAACTGTGGTGTTGTTCACGT
     N  S  Q  R  F  R  E  T  C  F  A  F  A  L  T  P  Q  Q  V  Q

GCAAATCAGTAGTTCCATGGATATTTCTGGGACCAAATGTGACTTCACAGTACAGGTCCA
541 ---------+---------+---------+---------+---------+---------+ 600
    CGTTTAGTCATCAAGGTACCTATAAAGACCCTGGTTTACACTGAAGTGTCATGTCCAGGT
     Q  I  S  S  S  M  D  I  S  G  T  K  C  D  F  T  V  Q  V  Q

GTTAAGGTTTTGTTTATCAGAAACCAGTTGTCCACAAGAAGATCACTTCCCACCCAATCT
601 ---------+---------+---------+---------+---------+---------+ 660
    CAATTCCAAAACAAATAGTCTTTGGTCAACAGGTGTTCTTCTAGTGAAGGGTGGGTTAGA
     L  R  F  C  L  S  E  T  S  C  P  Q  E  D  H  F  P  P  N  L
```

FIGURE 1A

```
     TTGTGTGAAAGTGAATACAAAACCTTGCAGCCTTCCAGGTTACCTTCCACCTACAAAAAA
661  ------------+---------+---------+---------+---------+---------+ 720
     AACACACTTTCACTTATGTTTTGGAACGTCGGAAGGTCCAATGGAAGGTGGATGTTTTTT

C   V   K   V   N   T   K   P   C   S   L   P   G   Y   L   P   P   T   K   N

TGGCGTGGAACCAAAGCGACCCAGCCGACCAATTAATATCACCTCACTTGTCCGACTGTC
721  ------------+---------+---------+---------+---------+---------+ 780
     ACCGCACCTTGGTTTCGCTGGGTCGGCTGGTTAATTATAGTGGAGTGAACAGGCTGACAG

G   V   E   P   K   R   P   S   R   P   I   N   I   T   S   L   V   R   L   S

CACAACAGTACCAAACACGATTGTTGTTTCTTGGACTGCAGAAATTGGAAGAAACTATTC
781  ------------+---------+---------+---------+---------+---------+ 840
     GTGTTGTCATGGTTTGTGCTAACAACAAAGAACCTGACGTCTTTAACCTTCTTTGATAAG

T   T   V   P   N   T   I   V   V   S   W   T   A   E   I   G   R   N   Y   S

CATGGCAGTATATCTTGTAAAACAGTTGTCCTCAACAGTTCTTCTTCAGAGGTTACGAGC
841  ------------+---------+---------+---------+---------+---------+ 900
     GTACCGTCATATAGAACATTTTGTCAACAGGAGTTGTCAAGAAGAAGTCTCCAATGCTCG

M   A   V   Y   L   V   K   Q   L   S   S   T   V   L   L   Q   R   L   R   A

AAAGGGAATAAGGAATCCGGATCATTCTAGAGCTTTAATTAAAGAGAAGTTGACTGCGGA
901  ------------+---------+---------+---------+---------+---------+ 960
     TTTCCCTTATTCCTTAGGCCTAGTAAGATCTCGAAATTAATTTCTCTTCAACTGACGCCT

K   G   I   R   N   P   D   H   S   R   A   L   I   K   E   K   L   T   A   D

TCCAGACAGTGAAATAGCTACAACCAGCCTAAGGGTTTCTCTACTATGTCCACTTGGTAA
961  ------------+---------+---------+---------+---------+---------+ 1020
     AGGTCTGTCACTTTATCGATGTTGGTCGGATTCCCAAAGAGATGATACAGGTGAACCATT

P   D   S   E   I   A   T   T   S   L   R   V   S   L   L   C   P   L   G   K

AATGCGGCTGACAATTCCGTGTCGGGCCCTTACATGTTCTCATCTACAATGTTTTGACGC
1021 ------------+---------+---------+---------+---------+---------+ 1080
     TTACGCCGACTGTTAAGGCACAGCCCGGGAATGTACAAGAGTAGATGTTACAAAACTGCG

M   R   L   T   I   P   C   R   A   L   T   C   S   H   L   Q   C   F   D   A

AACTCTTTACATTCAGATGAATGAGAAAAAACCAACCTGGGTTTGTCCTGTCTGTGATAA
1081 ------------+---------+---------+---------+---------+---------+ 1140
     TTGAGAAATGTAAGTCTACTTACTCTTTTTTGGTTGGACCCAAACAGGACAGACACTATT

T   L   Y   I   Q   M   N   E   K   K   P   T   W   V   C   P   V   C   D   K

GAAGGCTCCATATGAACACCTTATTATTGATGGCTTGTTTATGGAAATCCTAAAGTACTG
1141 ------------+---------+---------+---------+---------+---------+ 1200
     CTTCCGAGGTATACTTGTGGAATAATAACTACCGAACAAATACCTTTAGGATTTCATGAC

K   A   P   Y   E   H   L   I   I   D   G   L   F   M   E   I   L   K   Y   C

TACAGACTGTGATGAAATACAATTTAAGGAGGATGGCACTTGGGCACCGATGAGATCAAA
1201 ------------+---------+---------+---------+---------+---------+ 1260
     ATGTCTGACACTACTTTATGTTAAATTCCTCCTACCGTGAACCCGTGGCTACTCTAGTTT

T   D   C   D   E   I   Q   F   K   E   D   G   T   W   A   P   M   R   S   K

AAAGGAAGTACAGGAAGTTTCTGCCTCTTACAATGGAGTCGATGGATGCTTGAGCTCCAC
1261 ------------+---------+---------+---------+---------+---------+ 1320
     TTTCCTTCATGTCCTTCAAAGACGGAGAATGTTACCTCAGCTACCTACGAACTCGAGGTG

```
      ATTGGAGCATCAGGTAGCGTCTCACCACCAGTCCTCAAATAAAAACAAGAAAGTAGAAGT
1321  ------------+---------+---------+---------+---------+---------+ 1380
      TAACCTCGTAGTCCATCGCAGAGTGGTGGTCAGGAGTTTATTTTTGTTCTTTCATCTTCA

L  E  H  Q  V  A  S  H  H  Q  S  S  N  K  N  K  K  V  E  V

GATTGACCTAACCATAGACAGTTCATCTGATGAAGAGGAAGAAGAGCCATCTGCCAAGAG
1381  ---------+---------+---------+---------+---------+---------+ 1440
      CTAACTGGATTGGTATCTGTCAAGTAGACTACTTCTCCTTCTTCTCGGTAGACGGTTCTC

I  D  L  T  I  D  S  S  S  D  E  E  E  E  P  S  A  K  R

GACCTGTCCTTCCCTATCTCCCACATCACCACTAAATAATAAAGGCATTTTAAGTCTTCC
1441  ---------+---------+---------+---------+---------+---------+ 1500
      CTGGACAGGAAGGGATAGAGGGTGTAGTGGTGATTTATTATTTCCGTAAAATTCAGAAGG

T  C  P  S  L  S  P  T  S  P  L  N  N  K  G  I  L  S  L  P

ACATCAAGCATCTCCAGTATCCCGCACCCCAAGCCTTCCTGCTGTAGACACAAGCTACAT
1501  ---------+---------+---------+---------+---------+---------+ 1560
      TGTAGTTCGTAGAGGTCATAGGGCGTGGGGTTCGGAAGGACGACATCTGTGTTCGATGTA

H  Q  A  S  P  V  S  R  T  P  S  L  P  A  V  D  T  S  Y  I

TAATACCTCCCTCATCCAAGACTATAGGCATCCTTTCCACATGACACCCATGCCTTACGA
1561  ---------+---------+---------+---------+---------+---------+ 1620
      ATTATGGAGGGAGTAGGTTCTGATATCCGTAGGAAAGGTGTACTGTGGGTACGGAATGCT

N  T  S  L  I  Q  D  Y  R  H  P  F  H  M  T  P  M  P  Y  D

CTTACAAGGATTAGATTTCTTTCCTTTCTTATCAGGAGACAATCAGCATTACAACACCTC
1621  ---------+---------+---------+---------+---------+---------+ 1680
      GAATGTTCCTAATCTAAAGAAAGGAAAGAATAGTCCTCTGTTAGTCGTAATGTTGTGGAG

L  Q  G  L  D  F  F  P  F  L  S  G  D  N  Q  H  Y  N  T  S

CTTGCTTGCCGCTGCAGCAGCAGCAGTTTCAGATGATCAAGACCTCCTACACTCGTCTCG
1681  ---------+---------+---------+---------+---------+---------+ 1740
      GAACGAACGGCGACGTCGTCGTCGTCAAAGTCTACTAGTTCTGGAGGATGTGAGCAGAGC

L  L  A  A  A  A  A  V  S  D  D  Q  D  L  L  H  S  S  R

GTTTTTCCCGTATACCTCCTCACAGATGTTTCTTGATCAGTTAAGTGCAGGAGGCAGTAC
1741  ---------+---------+---------+---------+---------+---------+ 1800
      CAAAAAGGGCATATGGAGGAGTGTCTACAAAGAACTAGTCAATTCACGTCCTCCGTCATG

F  F  P  Y  T  S  S  Q  M  F  L  D  Q  L  S  A  G  G  S  T

TTCTCTGCCAACCACCAATGGAAGCAGTAGTGGCAGTAACAGCAGCCTGGTTTCTTCCAA
1801  ---------+---------+---------+---------+---------+---------+ 1860
      AAGAGACGGTTGGTGGTTACCTTCGTCATCACCGTCATTGTCGTCGGACCAAAGAAGGTT

S  L  P  T  T  N  G  S  S  S  G  S  N  S  S  L  V  S  S  N

CAGCCTAAGGGAAAGCCATAGCCACACCGTCACAAACAGGAGCAGCACGGACACGGCATC
1861  ---------+---------+---------+---------+---------+---------+ 1920
      GTCGGATTCCCTTTCGGTATCGGTGTGGCAGTGTTTGTCCTCGTCGTGCCTGTGCCGTAG

S  L  R  E  S  H  S  H  T  V  T  N  R  S  S  T  D  T  A  S

CATCTTTGGCATCATACCAGACATTATTTCATTGGACTGATTCCCAGGCCCTGCTGCTCC
1921  ---------+---------+---------+---------+---------+---------+ 1980
      GTAGAAACCGTAGTATGGTCTGTAATAAAGTAACCTGACTAAGGGTCCGGGACGACGAGG

```
      CATCCCCACCCCAGATCGAATGAACTTGGCAGAAAGAAGAGAACTTTGTGCTCTGTTTTA
1981  ------------------+---------+---------+---------+---------+ 2040
      GTAGGGTGGGGTCTAGCTTACTTGAACCGTCTTTCTTCTCTTGAAACACGAGACAAAAT

CCTTACTCTGTTTAGAAAAGTATACAAGCGTGTTTTTTTTCCTTTTTTTAGGGAAAAAAT
2041  ---------+---------+---------+---------+---------+---------+ 2100
      GGAATGAGACAAATCTTTTCATATGTTCGCACAAAAAAAAGGAAAAAAATCCCTTTTTTA

TAAAAGAAATGTACAGAGAACAAAACTATATTTTCAGTTTTACTTTTGTATATAAATCTA
2101  ---------+---------+---------+---------+---------+---------+ 2160
      ATTTTCTTTACATGTCTCTTGTTTTGATATAAAAGTCAAAATGAAAACATATATTTAGAT

AGACTGCCTGTGTGATAAAACACTTGTTTAAAAAAAAAAAAAAAAAAAA
2161  ---------+---------+---------+---------+-------- 2208
      TCTGACGGACACACTATTTTGTGAACAAATTTTTTTTTTTTTTTTTTTT
```

FIGURE 1D

```
    CGAGGGACTTTGAACATGTCGGGGATCGCCCTCAGCAGACTCGCCCAGGAGAGGAAAGCA
  1 --------+---------+---------+---------+---------+---------+  60
    GCTCCCTGAAACTTGTACAGCCCCTAGCGGGAGTCGTCTGAGCGGGTCCTCTCCTTTCGT a    R  G  T  L  N  M  S  G  I  A  L  S  R  L  A  Q  E  R  K  A   -
b     E  G  L  *  T  C  R  G  S  P  S  A  D  S  P  R  R  G  K  H  -
c      R  D  F  E  H  V  G  D  R  P  Q  Q  T  R  P  G  E  E  S  M -

TGGAGGAAAGACCACCCATTTGGTTTCGTGGCTGTCCCAACAAAAAATCCCGATGGCACG
 61 --------+---------+---------+---------+---------+---------+ 120
    ACCTCCTTTCTGGTGGGTAAACCAAAGCACCGACAGGGTTGTTTTTTAGGGCTACCGTGC a    W  R  K  D  H  P  F  G  F  V  A  V  P  T  K  N  P  D  G  T   -
b     G  G  K  T  T  H  L  V  S  W  L  S  Q  Q  K  I  P  M  A  R  -
c      E  E  R  P  P  I  W  F  R  G  C  P  N  K  K  S  R  W  H  D -

ATGAACCTCATGAACTGGGAGAGCGCCATTCCAGGAAAGAAAGGGACTCCGTGGGAAGGA
121 --------+---------+---------+---------+---------+---------+ 180
    TACTTGGAGTACTTGACCCTCTCGCGGTAAGGTCCTTTCTTTCCCTGAGGCACCCTTCCT a    M  N  L  M  N  W  E  S  A  I  P  G  K  K  G  T  P  W  E  G   -
b     *  T  S  *  T  G  R  A  P  F  Q  E  R  K  G  L  R  G  K  E  -
c      E  P  H  E  L  G  E  R  H  S  R  K  E  R  D  S  V  G  R  R -

GGCTTGTTTAAACTACGGATGCTTTTCAAAGATGATTATCCATCTTCGCCACCAAAATGT
181 --------+---------+---------+---------+---------+---------+ 240
    CCGAACAAATTTGATGCCTACGAAAAGTTTCTACTAATAGGTAGAAGCGGTGGTTTTACA a    G  L  F  K  L  R  M  L  F  K  D  D  Y  P  S  S  P  P  K  C   -
b     A  C  L  N  Y  G  C  F  S  K  M  I  I  H  L  R  H  Q  N  V  -
c      L  V  *  T  T  D  A  F  Q  R  *  L  S  I  F  A  T  K  M  * -

AAATTCGAACCACCATTATTTCACCCGAATGTGTACTTCGGGACAGTGTGCCTGTCCATC
241 --------+---------+---------+---------+---------+---------+ 300
    TTTAAGCTTGGTGGTAATAAAGTGGGCTTACACATGAAGCCCTGTCACACGGACAGGTAG a    K  F  E  P  P  L  F  H  P  N  V  Y  F  G  T  V  C  L  S  I   -
b     N  S  N  H  H  Y  F  T  R  M  C  T  S  G  Q  C  A  C  P  S  -
c      I  R  T  T  I  I  S  P  E  C  V  L  R  D  S  V  P  V  H  L -

TTAGAGGAGGACAAGGACTGGAGGCCAGCCATCACAATCAAACAGATCCTATTAGGAATA
301 --------+---------+---------+---------+---------+---------+ 360
    AATCTCCTCCTGTTCCTGACCTCCGGTCGGTAGTGTTAGTTTGTCTAGGATAATCCTTAT a    L  E  E  D  K  D  W  R  P  A  I  T  I  K  Q  I  L  L  G  I   -
b     *  R  R  T  R  T  G  G  Q  P  S  Q  S  N  R  S  Y  *  E  Y  -
c      R  G  G  Q  G  L  E  A  S  H  H  N  Q  T  D  P  I  R  N  T -

CAGGAACTTCTAAATGAACCAAATATCCAAGACCCAGCTCAAGCAGAGGCCTACACGATT
361 --------+---------+---------+---------+---------+---------+ 420
    GTCCTTGAAGATTTACTTGGTTTATAGGTTCTGGGTCGAGTTCGTCTCCGGATGTGCTAA a    Q  E  L  L  N  E  P  N  I  Q  D  P  A  Q  A  E  A  Y  T  I   -
b     R  N  F  *  M  N  Q  I  S  K  T  Q  L  K  Q  R  P  T  R  F  -
c      G  T  S  K  *  T  K  Y  P  R  P  S  S  S  R  G  L  H  D  L -

TACTGCCAAAACAGAGTGGAGTACGAGAAAAGGGTCCGAGCTCAAGCCAAGAATTTGCGC
421 --------+---------+---------+---------+---------+---------+ 480
    ATGACGGTTTTGTCTCACCTCATGCTCTTTTCCCAGGCTCGAGTTCGGTTCTTAAACGCG a    Y  C  Q  N  R  V  E  Y  E  K  R  V  R  A  Q  A  K  N  L  R   -
b     T  A  K  T  E  W  S  T  R  K  G  S  E  L  K  P  R  I  C  A  -
c      L  P  K  Q  S  G  V  R  E  K  G  P  S  S  Q  E  F  A  P    -
```

FIGURE 2A

```
           CCTCATAAGCAGCGACCTTGTGGCATCGTCAGAAGGAAGGGATTGGTTTGGCAAGAACTT
       481 ------------------------------------------------------------ 540
           GGAGTATTCGTCGCTGGAACACCGTAGCAGTCTTCCTTCCCTAACCAAACCGTTCTTGAA a       P  H  K  Q  R  P  C  G  I  V  R  R  K  G  L  V  W  Q  E  L   -
    b       L  I  S  S  D  L  V  A  S  S  E  G  R  D  W  F  G  K  N  L   -
    c       S  *  A  A  T  L  W  H  R  Q  K  E  G  I  G  L  A  R  T  C   -

GTTTACAACATTTTTGCAAATCTAAAGTTGCTCCATACAATGACTAGTCACCTGGGGGGG
       541 ------------------------------------------------------------ 600
           CAAATGTTGTAAAAACGTTTAGATTTCAACGAGGTATGTTACTGATCAGTGGACCCCCCC a       V  Y  N  I  F  A  N  L  K  L  L  H  T  M  T  S  H  L  G  G   -
    b       F  T  T  F  L  Q  I  *  S  C  S  I  Q  *  L  V  T  W  G  G   -
    c       L  Q  H  F  C  K  S  K  V  A  P  Y  N  D  *  S  P  G  G  V   -

TTGGGCGGGCGCCATCTTCCATTGCCGCCGCGGGTGTGCGGTCTCGATTCGCTGAATTGC
       601 ------------------------------------------------------------ 660
           AACCCGCCCGCGGTAGAAGGTAACGGCGGCGCCCACACGCCAGAGCTAAGCGACTTAACG a       L  G  G  R  H  L  P  L  P  P  R  V  C  G  L  D  S  L  N  C   -
    b       W  A  G  A  I  F  H  C  R  R  G  C  A  V  S  I  R  *  I  A   -
    c       G  R  A  P  S  S  I  A  A  A  G  V  R  S  R  F  A  E  L  P   -

CCGTTTCCATACAGGGTCTCTTCTTCGGTCTTTTGTATTTTTGATTGTTATGTAAAACTC
       661 ------------------------------------------------------------ 720
           GGCAAAGGTATGTCCCAGAGAAGAAGCCAGAAAACATAAAAACTAACAATACATTTTGAG a       P  F  P  Y  R  V  S  S  S  V  F  C  I  F  D  C  Y  V  K  L   -
    b       R  F  H  T  G  S  L  L  R  S  F  V  F  L  I  V  M  *  N  S   -
    c       V  S  I  Q  G  L  F  F  G  L  L  Y  F  *  L  L  C  K  T  R   -

GCTTTTATTTTAATATTGATGTCAGTATTTCAACTGCTGTAAAATTATAAACTTTTATAC
       721 ------------------------------------------------------------ 780
           CGAAAATAAAATTATAACTACAGTCATAAAGTTGACGACATTTTAATATTTGAAAATATG a       A  F  I  L  I  L  M  S  V  F  Q  L  L  *  N  Y  K  L  L  Y   -
    b       L  L  F  *  Y  *  C  Q  Y  F  N  C  C  K  I  I  N  F  Y  T   -
    c       F  Y  F  N  I  D  V  S  I  S  T  A  V  K  L  *  T  F  I  L   -

TTGGGTAAGTCCCCCAGGGCGAGTTCCTCGCTCTGGGATGCAGGCATGCTTCTCACCGTG
       781 ------------------------------------------------------------ 840
           AACCCATTCAGGGGGTCCCGCTCAAGGAGCGAGACCCTACGTCCGTACGAAGAGTGGCAC a       L  G  K  S  P  R  A  S  S  S  L  W  D  A  G  M  L  L  T  V   -
    b       W  V  S  P  P  G  R  V  P  R  S  G  M  Q  A  C  F  S  P  C   -
    c       G  *  V  P  Q  G  E  F  L  A  L  G  C  R  H  A  S  H  R  A   -

CAGAGCTGCACTTGGCCTCAGCTGGCTGTATGGAAATGCACCCTCCCTCCTGCGCTCCTC
       841 ------------------------------------------------------------ 900
           GTCTCGACGTGAACCGGAGTCGACCGACATACCTTTACGTGGGAGGGAGGACGCGAGGAG a       Q  S  C  T  W  P  Q  L  A  V  W  K  C  T  L  P  P  A  L  L   -
    b       R  A  A  L  G  L  S  W  L  Y  G  N  A  P  S  L  L  R  S  S   -
    c       E  L  H  L  A  S  A  G  C  M  E  M  H  P  P  S  C  A  P  L   -

TCTAGAACCTTCTAGAACCTGGGCTGTGCTGCTTTTGAGCCTCAGACCCCAGGGCAGCAT
       901 ------------------------------------------------------------ 960
           AGATCTTGGAAGATCTTGGACCCGACACGACGAAAACTCGGAGTCTGGGGTCCCGTCGTA a       S  R  T  F  *  N  L  G  C  A  A  F  E  P  Q  T  P  G  Q  H   -
    b       L  E  P  S  R  T  W  A  V  L  L  L  S  L  R  P  Q  G  S  I   -
    c       *  N  L  L  E  P  G  L  C  C  F  *  A  S  D  P  R  A  A  S   -
```

FIGURE 2B

```
          TTCGGTTCTGCGCCACTTCCTTTGTGTTTATATGGCGTTTTGTCTGTGTTGCTGTTTAGA
    961   ------------------------------------------------------------  1020
          AAGCCAAGACGCGGTGAAGGAAACACAAATATACCGCAAAACAGACACAACGACAAATCT a        L  G  S  A  P  L  P  L  C  L  Y  G  V  L  S  V  L  L  F  R    -
    b         S  V  L  R  H  F  L  C  V  Y  M  A  F  C  L  C  C  C  L  E   -
    c          R  F  C  A  T  S  F  V  F  I  W  R  F  V  C  V  A  V  *  S  -

GTAAATAAACTGTTTATATAAAAAAAAAAAAAAAAAAAAAAAGTCCGAATTGCGCACGAGGCGC
    1021  ------------------------------------------------------------  1080
          CATTTATTTGACAAATATATTTTTTTTTTTTTTTTTTTTTTTCAGGCTTAACGCGTGCTCCGCG a        V  N  K  L  F  I  *  K  K  K  K  K  K  S  E  L  R  T  R  R    -
    b         *  I  N  C  L  Y  K  K  K  K  K  K  K  S  P  N  C  A  R  G  A -
    c          K  *  T  V  Y  I  K  K  K  K  K  K  V  R  I  A  H  E  A  L  -

TATCACCACCTCAGTTATACTCTTATTCCTAGATATTTGGGACATAAGAACCAAAATCTA
    1081  ------------------------------------------------------------  1140
          ATAGTGGTGGAGTCAATATGAGAATAAGGATCTATAAACCCTGTATTCTTGGTTTTAGAT a        Y  H  H  L  S  Y  T  L  I  P  R  Y  L  G  H  K  N  Q  N  L    -
    b         I  T  T  S  V  I  L  L  F  L  D  I  W  D  I  R  T  K  I  *   -
    c          S  P  P  Q  L  Y  S  Y  S  *  I  F  G  T  *  E  P  K  S  K  -

AAAATTAAGAGGTTTCCTCCTCAAATACAGAATAAAAGCTGCTATGCCTGAGGCATACAG
    1141  ------------------------------------------------------------  1200
          TTTTAATTCTCCAAAGGAGGAGTTTATGTCTTATTTTCGACGATACGGACTCCGTATGTC a        K  I  K  R  F  P  P  Q  I  Q  N  K  S  C  Y  A  *  G  I  Q    -
    b         K  L  R  G  F  L  L  K  Y  R  I  K  A  A  M  P  E  A  Y  R   -
    c          N  *  E  V  S  S  S  N  T  E  *  K  L  L  C  L  R  H  T  G -

GGCTTTGTTGGTCCGGCACATCATATTTTACTATTTGTTTGAGGTATTTGCCGAATCTTG
    1201  ------------------------------------------------------------  1260
          CCGAAACAACCAGGCCGTGTAGTATAAAATGATAAACAAACTCCATAAACGGCTTAGAAC a        G  F  V  G  P  A  H  H  I  L  L  F  V  *  G  I  C  R  I  L    -
    b         A  L  L  V  R  H  I  I  F  Y  Y  L  F  E  V  F  A  E  S  C   -
    c          L  C  W  S  G  T  S  Y  F  T  I  C  L  R  Y  L  P  N  L  V -

TTAATAACAGTGAATAATCTTGTCTTTTTATTTTAATATACACAGCACAGTAAAGAAAAG
    1261  ------------------------------------------------------------  1320
          AATTATTGTCACTTATTAGAACAGAAAAATAAAATTATATGTGTCGTGTCATTTCTTTTC a        L  I  T  V  N  N  L  V  F  L  F  *  Y  T  Q  H  S  K  E  K    -
    b         *  *  Q  *  I  I  L  S  F  Y  F  N  I  H  S  T  V  K  K  S   -
    c          N  N  S  E  *  S  C  L  F  I  L  I  Y  T  A  Q  *  R  K  A -

CATTAATTGCGTTTTGTGGACTTTACAACATGGCTAAACCCATATTCTTAGATTTGGACA
    1321  ------------------------------------------------------------  1380
          GTAATTAACGCAAAACACCTGAAATGTTGTACCGATTTGGGTATAAGAATCTAAACCTGT a        H  *  L  R  F  V  D  F  T  T  W  L  N  P  Y  S  *  I  W  T    -
    b         I  N  C  V  L  W  T  L  Q  H  G  *  T  H  I  L  R  F  G  H   -
    c          L  I  A  F  C  G  L  Y  N  M  A  K  P  I  F  L  D  L  D  I -

TAGATAGATGCTTAGTAAATACTAAATTGAAATGAATTAGGCCAGAGGAGATCAGACATA
    1381  ------------------------------------------------------------  1440
          ATCTATCTACGAATCATTTATGATTTAACTTTACTTAATCCGGTCTCCTCTAGTCTGTAT a        *  I  D  A  *  *  I  L  N  *  N  E  L  G  Q  R  R  S  D  I    -
    b         R  *  M  L  S  K  Y  *  I  E  M  N  *  A  R  G  D  Q  T  *   -
    c          D  R  C  L  V  N  T  K  L  K  *  I  R  P  E  E  I  R  H  R -
```

FIGURE 2C

```
       GGAATTTAAAGTTAGTCTTGAGAGAAACTTAGGTAAAAAGAAAAACAAAATTAAAGGAGG
  1441 ------------------------------------------------------------ 1500
       CCTTAAATTTCAATCAGAACTCTCTTTGAATCCATTTTTCTTTTTGTTTTAATTTCCTCC a      G  I  *  S  *  S  *  E  K  R  *  K  E  K  Q  N  *  R  R   -
b         E  F  K  V  S  L  E  R  N  L  G  K  K  K  N  K  I  K  G  G  -
c      N  L  K  L  V  L  R  E  T  *  V  K  R  K  T  K  L  K  E  Q -

ACTGTGTGTGAGAGTTGAAAGATATAAGTTCCAGAATGTTGTGGCAGGACAGTGAAATCT
  1501 ------------------------------------------------------------ 1560
       TGACACACACTCTCAACTTTCTATATTCAAGGTCTTACAACACCGTCCTGTCACTTTAGA a      T  V  C  E  S  *  K  I  *  V  P  E  C  C  G  R  T  V  K  S  -
b      L  C  V  R  V  E  R  Y  K  F  Q  N  V  V  A  G  Q  *  N  L  -
c         C  V  *  E  L  K  D  I  S  S  R  M  L  W  Q  D  S  E  I  F -

TCTGGTTCCTAAAGACGGAGGAGACTCTCTCCCAGCACCTGACTTCCACCCTCCCACTAC
  1561 ------------------------------------------------------------ 1620
       AGACCAAGGATTTCTGCCTCCTCTGAGAGAGGGTCGTGGACTGAAGGTGGGAGGGTGATG a      S  G  S  *  R  R  R  R  L  S  P  S  T  *  L  P  P  S  H  Y  -
b      L  V  P  K  D  G  G  D  S  L  P  A  P  D  F  H  P  P  T  T  -
c         W  F  L  K  T  E  E  T  L  S  Q  H  L  T  S  T  L  P  L  L -

TGCCAGACCTTTGCCTGGGCTGTTCCTAGCCTGGAGCACTGTCCCCCGTCTCGATCCTGC
  1621 ------------------------------------------------------------ 1680
       ACGGTCTGGAAACGGACCCGACAAGGATCGGACCTCGTGACAGGGGGCAGAGCTAGGACG a      C  Q  T  F  A  W  A  V  P  S  L  E  H  C  P  P  S  R  S  C  -
b      A  R  P  L  P  G  L  F  L  A  W  S  T  V  P  R  L  D  P  A  -
c         P  D  L  C  L  G  C  S  *  P  G  A  L  S  P  V  S  I  L  P -

CTTCCCCTGAAACCCCTGCAGGGGCTGCCCTCTTTTGGCCTCCCACTGTGTCCCTTCTCT
  1681 ------------------------------------------------------------ 1740
       GAAGGGGACTTTGGGGACGTCCCCGACGGGAGAAAACCGGAGGGTGACACAGGGAAGAGA a      L  P  L  K  P  L  Q  G  L  P  S  F  G  L  P  L  C  P  F  S  -
b      F  P  *  N  P  C  R  G  C  P  L  L  A  S  H  C  V  P  S  L  -
c         S  P  E  T  P  A  G  A  A  L  F  W  P  P  T  V  S  L  L  S -

CATGTGCATTAGATCTCAGCCTGGCCTTGAATGTCTCTTTCTCACCAGTACCTTGCACAG
  1741 ------------------------------------------------------------ 1800
       GTACACGTAATCTAGAGTCGGACCGGAACTTACAGAGAAAGAGTGGTCATGGAACGTGTC a      H  V  H  *  I  S  A  W  P  *  M  S  L  S  H  Q  Y  L  A  Q  -
b      M  C  I  R  S  Q  P  G  L  E  C  L  F  L  T  S  T  L  H  S  -
c         C  A  L  D  L  S  L  A  L  N  V  S  F  S  P  V  P  C  T  V -

TAAACATTCAAACTTACTGTGAATTCATCTGAAAAAAAAAAAAAAAAAAAA
  1801 -------------------------------------------------- 1849
       ATTTGTAAGTTTGAATGACACTTAAGTAGACTTTTTTTTTTTTTTTTTTTT a      *  T  F  K  L  T  V  N  S  S  E  K  K  K  K  K     -
b      K  H  S  N  L  L  *  I  H  L  K  K  K  K  K  K     -
c         N  I  Q  T  Y  C  E  F  I  *  K  K  K  K  K     -
s
```

FIGURE 2D 5,756,669

SEQUENCE LISTING ( 1 ) GENERAL INFORMATION:

( i i i ) NUMBER OF SEQUENCES: 126

( 2 ) INFORMATION FOR SEQ ID NO:1:

( i ) SEQUENCE CHARACTERISTICS:
        ( A ) LENGTH: 1962 base pairs
        ( B ) TYPE: nucleic acid
        ( C ) STRANDEDNESS: single
        ( D ) TOPOLOGY: linear ( i i ) MOLECULE TYPE: peptide ( i i i ) HYPOTHETICAL: NO ( i x ) FEATURE:
        ( A ) NAME/KEY: CDS
        ( B ) LOCATION: 118..591

( x i ) SEQUENCE DESCRIPTION: SEQ ID NO:1:

```
AATTCGGCAC  GAGGGGAAGT  CCCGAGACAA  AGGGAAGCGC  CGCCGCCGCC  GCCCGCTCG      60

GTCCTCCACC  TGTCCGCTAC  GCTCGCCGGG  GCTGCGGCCG  CCCGAGGGAC  TTTGAAC       117
```

-continued

```
ATG TCG GGG ATC GCC CTC AGC AGA CTC GCC CAG GAG AGG AAA GCA TGG    165
Met Ser Gly Ile Ala Leu Ser Arg Leu Ala Gln Glu Arg Lys Ala Trp
 1               5                  10                  15

AGG AAA GAC CAC CCA TTT GGT TTC GTG GCT GTC CCA ACA AAA AAT CCC    213
Arg Lys Asp His Pro Phe Gly Phe Val Ala Val Pro Thr Lys Asn Pro
             20                  25                  30

GAT GGC ACG ATG AAC CTC ATG AAC TGG GAG AGC GCC ATT CCA GGA AAG    261
Asp Gly Thr Met Asn Leu Met Asn Trp Glu Ser Ala Ile Pro Gly Lys
         35                  40                  45

AAA GGG ACT CCG TGG GAA GGA GGC TTG TTT AAA CTA CGG ATG CTT TTC    309
Lys Gly Thr Pro Trp Glu Gly Gly Leu Phe Lys Leu Arg Met Leu Phe
     50                  55                  60

AAA GAT GAT TAT CCA TGT TCG CCA CCA AAA TGT AAA TTC GAA CCA CCA    357
Lys Asp Asp Tyr Pro Cys Ser Pro Pro Lys Cys Lys Phe Glu Pro Pro
 65              70                  75                  80

TTA TTT CAC CCG AAT GTG TAC CCT TCG GGG ACA GTG TGC CTG TCC ATC    405
Leu Phe His Pro Asn Val Tyr Pro Ser Gly Thr Val Cys Leu Ser Ile
             85                  90                  95

TTA GAG GAG GAC AAG GAC TGG AGG CCA GCC ATC ACA ATC AAA CAG ATC    453
Leu Glu Glu Asp Lys Asp Trp Arg Pro Ala Ile Thr Ile Lys Gln Ile
        100                 105                 110

CTA TTA GGA ATA CAG GAA CTT CTA AAT GAA CCA AAT ATC CAA GAC CCA    501
Leu Leu Gly Ile Gln Glu Leu Leu Asn Glu Pro Asn Ile Gln Asp Pro
    115                 120                 125

GCT CAA GCA GAG GCC TAC ACG ATT TAC TGC CAA AAC AGA GTG GAG TAC    549
Ala Gln Ala Glu Ala Tyr Thr Ile Tyr Cys Gln Asn Arg Val Glu Tyr
130                 135                 140

GAG AAA AGG GTC CGA GCA CAA GCC AAG AAG TTT GCG CCC TCA              591
Glu Lys Arg Val Arg Ala Gln Ala Lys Lys Phe Ala Pro Ser
145                 150                 155

TAAGCAGCGA CCTTGTGGCA TCGTCAAAAG GAAGGGATTG GTTGGCAAG AACTTGTTTA    651
CAACATTTTT GCAAATCTAA AGTTGCTCCA TACATGACTA GTCACCTGGG GGGGTTGGGC    711
GGGCGCCATC TTCCATTGCC GCCGCGGGTG TGCGGTCTCG ATTCGCTGAA TTGCCCGTTT    771
CCATACAGGG TCTCTTCTTC GGTCTTTTGT ATTTTGATT GTTATGTAAA ACTCGCTTTT    831
ATTTTAATAT TGATGTCAGT ATTTCAACTG CTGTAAAATT ATAAACTTTT ATACTTGGGT    891
AAGTCCCCCA GGGCGAGTTC CTCGCTCTGG GATGCAGGCA TGCTTCTCAC CGTGCAGAGC    951
TGCACTTGGC CTCAGCTGGC TGTATGGAAA TGCACCCTCC CTCCTGCGCT CCTCTCTAGA   1011
ACCTTCTAGA ACCTGGGCTG TGCTGCTTTT GAGCCTCAGA CCCCAGGGCA GCATCTCGGT   1071
TCTGCGCCAC TTCCTTTGTG TTTATATGGC GTTTTGTCTG TGTTGCTGTT TAGAGTAAAT   1131
AAACTGTTTA TATAAAAAAA AAAAAAAAAA AAGTCCGAAT TGCGCACGAG GCGCTATCAC   1191
CACCTCAGTT ATACTCTTAT TCCTAGATAT TTGGGACATA AGAACCAAAA TCTAAAAATT   1251
AAGAGGTTTC CTCCTCAAAT ACAGAATAAA AGCTGCTATG CCTGAGGCAT ACAGGGCTTT   1311
GTTGGTCCGG CACATCATAT TTTACTATTT GTTGAGGTA TTTGCCGAAT CTTGTTAATA    1371
ACAGTGAATA ATCTTGTCTT TTTATTTTAA TATACACAGC ACAGTAAAGA AAAGCATTAA   1431
TTGCGTTTTG TGGACTTTAC AACATGGCTA AACCCATATT CTTAGATTTG GACATAGATA   1491
GATGCTTAGT AAATACTAAA TTGAAATGAA TTAGGCCAGA GGAGATCAGA CATAGGAATT   1551
TAAAGTTAGT CTTGAGAGAA ACTTAGGTAA AAAGAAAAC AAAATTAAAG GAGGACTGTG    1611
TGTGAGAGTT GAAAGATATA AGTTCCAGAA TGTTGTGGCA GGACAGTGAA ATCTTCTGGT   1671
TCCTAAAGAC GGAGGAGACT CTCTCCCAGC ACCTGACTTC CACCCTCCCA CTACTGCCAG   1731
ACCTTTGCCT GGGCTGTTCC TAGCCTGGAG CACTGTCCCC CGTCTCGATC CTGCCTTCCC   1791
```

```
CTGAAACCCC TGCAGGGGCT GCCCTCTTTT GGCCTCCCAC TGTGTCCCTT CTCTCATGTG    1851

CATTAGATCT CAGCCTGGCC TTGAATGTCT CTTTCTCACC AGTACCTTGC ACAGTAAACA    1911

TTCAAACTTA CTGTGAATTC ATCTGAAAAA AAAAAAAAA AAACTCGAAT C              1962
```

( 2 ) INFORMATION FOR SEQ ID NO:2:

( i ) SEQUENCE CHARACTERISTICS:
        ( A ) LENGTH: 158 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ser Gly Ile Ala Leu Ser Arg Leu Ala Gln Glu Arg Lys Ala Trp
 1               5                  10                  15

Arg Lys Asp His Pro Phe Gly Phe Val Ala Val Pro Thr Lys Asn Pro
            20                  25                  30

Asp Gly Thr Met Asn Leu Met Asn Trp Glu Ser Ala Ile Pro Gly Lys
        35                  40                  45

Lys Gly Thr Pro Trp Glu Gly Gly Leu Phe Lys Leu Arg Met Leu Phe
    50                  55                  60

Lys Asp Asp Tyr Pro Cys Ser Pro Pro Lys Cys Lys Phe Glu Pro Pro
65                  70                  75                  80

Leu Phe His Pro Asn Val Tyr Pro Ser Gly Thr Val Cys Leu Ser Ile
                85                  90                  95

Leu Glu Glu Asp Lys Asp Trp Arg Pro Ala Ile Thr Ile Lys Gln Ile
            100                 105                 110

Leu Leu Gly Ile Gln Glu Leu Leu Asn Glu Pro Asn Ile Gln Asp Pro
        115                 120                 125

Ala Gln Ala Glu Ala Tyr Thr Ile Tyr Cys Gln Asn Arg Val Glu Tyr
    130                 135                 140

Glu Lys Arg Val Arg Ala Gln Ala Lys Lys Phe Ala Pro Ser
145                 150                 155
```

( 2 ) INFORMATION FOR SEQ ID NO:3:

( i ) SEQUENCE CHARACTERISTICS:
        ( A ) LENGTH: 1849 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..759

( x i ) SEQUENCE DESCRIPTION: SEQ ID NO:3:

```
CGA GGG ACT TTG AAC ATG TCG GGG ATC GCC CTC AGC AGA CTC GCC CAG     48
Arg Gly Thr Leu Asn Met Ser Gly Ile Ala Leu Ser Arg Leu Ala Gln
 1               5                  10                  15

GAG AGG AAA GCA TGG AGG AAA GAC CAC CCA TTT GGT TTC GTG GCT GTC     96
Glu Arg Lys Ala Trp Arg Lys Asp His Pro Phe Gly Phe Val Ala Val
            20                  25                  30

CCA ACA AAA AAT CCC GAT GGC ACG ATG AAC CTC ATG AAC TGG GAG AGC    144
Pro Thr Lys Asn Pro Asp Gly Thr Met Asn Leu Met Asn Trp Glu Ser
        35                  40                  45

GCC ATT CCA GGA AAG AAA GGG ACT CCG TGG GAA GGA GGC TTG TTT AAA    192
Ala Ile Pro Gly Lys Lys Gly Thr Pro Trp Glu Gly Gly Leu Phe Lys
```

```
                                    50                              55                              60
CTA CGG ATG CTT TTC AAA GAT GAT TAT CCA TCT TCG CCA CCA AAA TGT                240
Leu Arg Met Leu Phe Lys Asp Asp Tyr Pro Ser Ser Pro Pro Lys Cys
65                       70                      75                      80

AAA TTC GAA CCA CCA TTA TTT CAC CCG AAT GTG TAC TTC GGG ACA GTG                288
Lys Phe Glu Pro Pro Leu Phe His Pro Asn Val Tyr Phe Gly Thr Val
                         85                      90                      95

TGC CTG TCC ATC TTA GAG GAG GAC AAG GAC TGG AGG CCA GCC ATC ACA                336
Cys Leu Ser Ile Leu Glu Glu Asp Lys Asp Trp Arg Pro Ala Ile Thr
                100                     105                     110

ATC AAA CAG ATC CTA TTA GGA ATA CAG GAA CTT CTA AAT GAA CCA AAT                384
Ile Lys Gln Ile Leu Leu Gly Ile Gln Glu Leu Leu Asn Glu Pro Asn
        115                     120                     125

ATC CAA GAC CCA GCT CAA GCA GAG GCC TAC ACG ATT TAC TGC CAA AAC                432
Ile Gln Asp Pro Ala Gln Ala Glu Ala Tyr Thr Ile Tyr Cys Gln Asn
        130                     135                     140

AGA GTG GAG TAC GAG AAA AGG GTC CGA GCT CAA GCC AAG AAT TTG CGC                480
Arg Val Glu Tyr Glu Lys Arg Val Arg Ala Gln Ala Lys Asn Leu Arg
145                     150                     155                     160

CCT CAT AAG CAG CGA CCT TGT GGC ATC GTC AGA AGG AAG GGA TTG GTT                528
Pro His Lys Gln Arg Pro Cys Gly Ile Val Arg Arg Lys Gly Leu Val
                165                     170                     175

TGG CAA GAA CTT GTT TAC AAC ATT TTT GCA AAT CTA AAG TTG CTC CAT                576
Trp Gln Glu Leu Val Tyr Asn Ile Phe Ala Asn Leu Lys Leu Leu His
                180                     185                     190

ACA ATG ACT AGT CAC CTG GGG GGG TTG GGC GGG CGC CAT CTT CCA TTG                624
Thr Met Thr Ser His Leu Gly Gly Leu Gly Gly Arg His Leu Pro Leu
        195                     200                     205

CCG CCG CGG GTG TGC GGT CTC GAT TCG CTG AAT TGC CCG TTT CCA TAC                672
Pro Pro Arg Val Cys Gly Leu Asp Ser Leu Asn Cys Pro Phe Pro Tyr
        210                     215                     220

AGG GTC TCT TCT TCG GTC TTT TGT ATT TTT GAT TGT TAT GTA AAA CTC                720
Arg Val Ser Ser Ser Val Phe Cys Ile Phe Asp Cys Tyr Val Lys Leu
225                     230                     235                     240

GCT TTT ATT TTA ATA TTG ATG TCA GTA TTT CAA CTG CTG TAAAATTATA                 769
Ala Phe Ile Leu Ile Leu Met Ser Val Phe Gln Leu Leu
                245                     250

AACTTTTATA CTTGGGTAAG TCCCCCAGGG CGAGTTCCTC GCTCTGGGAT GCAGGCATGC              829
TTCTCACCGT GCAGAGCTGC ACTTGGCCTC AGCTGGCTGT ATGGAAATGC ACCCTCCCTC              889
CTGCGCTCCT CTCTAGAACC TTCTAGAACC TGGGCTGTGC TGCTTTTGAG CCTCAGACCC              949
CAGGGCAGCA TCTCGGTTCT GCGCCACTTC CTTTGTGTTT ATATGGCGTT TTGTCTGTGT             1009
TGCTGTTTAG AGTAAATAAA CTGTTTATAT AAAAAAAAAA AAAAAAAAAG TCCGAATTGC             1069
GCACGAGGCG CTATCACCAC CTCAGTTATA CTCTTATTCC TAGATATTTG GGACATAAGA             1129
ACCAAAATCT AAAAATTAAG AGGTTCCTC CTCAAATACA GAATAAAAGC TGCTATGCCT              1189
GAGGCATACA GGGCTTTGTT GGTCCGGCAC ATCATATTTT ACTATTTGTT TGAGGTATTT             1249
GCCGAATCTT GTTAATAACA GTGAATAATC TTGTCTTTTT ATTTAATAT ACACAGCACA              1309
GTAAAGAAAA GCATTAATTG CGTTTGTGG ACTTACAAC ATGGCTAAAC CCATATTCTT               1369
AGATTTGGAC ATAGATAGAT GCTTAGTAAA TACTAAATTG AAATGAATTA GGCCAGAGGA             1429
GATCAGACAT AGGAATTTAA AGTTAGTCTT GAGAGAAACT TAGGTAAAAA GAAAACAAA              1489
ATTAAGGAG GACTGTGTGT GAGAGTTGAA AGATATAAGT TCCAGAATGT TGTGGCAGGA              1549
CAGTGAAATC TTCTGGTTCC TAAAGACGGA GGAGACTCTC TCCCAGCACC TGACTTCCAC             1609
CCTCCCACTA CTGCCAGACC TTTGCCTGGG CTGTTCCTAG CCTGGAGCAC TGTCCCCCGT             1669
```

| CTCGATCCTG | CCTTCCCCTG | AAACCCCTGC | AGGGGCTGCC | CTCTTTTGGC | CTCCCACTGT | 1729 |
| GTCCCTTCTC | TCATGTGCAT | TAGATCTCAG | CCTGGCCTTG | AATGTCTCTT | TCTCACCAGT | 1789 |
| ACCTTGCACA | GTAAACATTC | AAACTTACTG | TGAATTCATC | TGAAAAAAAA | AAAAAAAAAA | 1849 |

( 2 ) INFORMATION FOR SEQ ID NO:4:

( i ) SEQUENCE CHARACTERISTICS:
        ( A ) LENGTH: 253 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Arg Gly Thr Leu Asn Met Ser Gly Ile Ala Leu Ser Arg Leu Ala Gln
 1               5                  10                  15
Glu Arg Lys Ala Trp Arg Lys Asp His Pro Phe Gly Phe Val Ala Val
            20                  25                  30
Pro Thr Lys Asn Pro Asp Gly Thr Met Asn Leu Met Asn Trp Glu Ser
        35                  40                  45
Ala Ile Pro Gly Lys Lys Gly Thr Pro Trp Glu Gly Gly Leu Phe Lys
    50                  55                  60
Leu Arg Met Leu Phe Lys Asp Asp Tyr Pro Ser Ser Pro Pro Lys Cys
65                  70                  75                  80
Lys Phe Glu Pro Pro Leu Phe His Pro Asn Val Tyr Phe Gly Thr Val
                85                  90                  95
Cys Leu Ser Ile Leu Glu Glu Asp Lys Asp Trp Arg Pro Ala Ile Thr
            100                 105                 110
Ile Lys Gln Ile Leu Leu Gly Ile Gln Glu Leu Leu Asn Glu Pro Asn
        115                 120                 125
Ile Gln Asp Pro Ala Gln Ala Glu Ala Tyr Thr Ile Tyr Cys Gln Asn
    130                 135                 140
Arg Val Glu Tyr Glu Lys Arg Val Arg Ala Gln Ala Lys Asn Leu Arg
145                 150                 155                 160
Pro His Lys Gln Arg Pro Cys Gly Ile Val Arg Arg Lys Gly Leu Val
                165                 170                 175
Trp Gln Glu Leu Val Tyr Asn Ile Phe Ala Asn Leu Lys Leu Leu His
            180                 185                 190
Thr Met Thr Ser His Leu Gly Gly Leu Gly Gly Arg His Leu Pro Leu
        195                 200                 205
Pro Pro Arg Val Cys Gly Leu Asp Ser Leu Asn Cys Pro Phe Pro Tyr
    210                 215                 220
Arg Val Ser Ser Ser Val Phe Cys Ile Phe Asp Cys Tyr Val Lys Leu
225                 230                 235                 240
Ala Phe Ile Leu Ile Leu Met Ser Val Phe Gln Leu Leu
                245                 250
```

( 2 ) INFORMATION FOR SEQ ID NO:5:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

GCACGAGGCG GACAGTGCGG AACTAAAGCA AATGGTTATG    40

( 2 ) INFORMATION FOR SEQ ID NO:6:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

CTTCAAAAAT TACCATTTTA TGATTACTG GATGAACT     38

( 2 ) INFORMATION FOR SEQ ID NO:7:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

CATCAGACAA CAGTCAGCGC TTTCGAGAAA CCTGTTTTGC     40

( 2 ) INFORMATION FOR SEQ ID NO:8:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

CACAACAAGT GCAGCAAATC AGTAGTTCCA TGGATA     36

( 2 ) INFORMATION FOR SEQ ID NO:9:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

GTACAGGTCC AGTTAAGGTT TTGTTTATCA GAAACCAGTT G     41

( 2 ) INFORMATION FOR SEQ ID NO:10:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

TGAAAGTGAA TACAAAACCT TGCAGCCTTC CAGG     34

( 2 ) INFORMATION FOR SEQ ID NO:11:

( i ) SEQUENCE CHARACTERISTICS:

(A) LENGTH: 43 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:11:

CCACCTACAA AAAATGGCGT GGAACCAAAG CGACCCAGCC GAC    43

(2) INFORMATION FOR SEQ ID NO:12:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:12:

GACTGTCCAC AACAGTACCA AACACGATTG TTG    33

(2) INFORMATION FOR SEQ ID NO:13:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:13:

GGAAGAAACT ATTCCATGGC AGTATATCTT GTAAAACAGT    40

(2) INFORMATION FOR SEQ ID NO:14:

(i) SEQUENCE CHARACTERISTICS:
(A) LENGTH: 46 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:14:

CAGAGGTTAC GAGCAAAGGG AATAAGGAAT CCGGATCATT CTAGAG    46

(2) INFORMATION FOR SEQ ID NO:15:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:15:

GGATCCAGAC AGTGAAATAG CTACAACCAG CCTAAG    36

(2) INFORMATION FOR SEQ ID NO:16:

(i) SEQUENCE CHARACTERISTICS:
(A) LENGTH: 41 base pairs
(B) TYPE: nucleic acid
(C) STRANDEDNESS: single
(D) TOPOLOGY: linear ( i i ) MOLECULE TYPE: DNA ( x i ) SEQUENCE DESCRIPTION: SEQ ID NO:16:

CTTGGTAAAA TGCGGCTGAC AATTCCGTGT CGGGCCCTTA C                      41

( 2 ) INFORMATION FOR SEQ ID NO:17:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

CATCTACAAT GTTTGACGC AACTCTTTAC ATTCAGATG                          39

( 2 ) INFORMATION FOR SEQ ID NO:18:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

GTCCTGTCTG TGATAAGAAG GCTCCATATG AACACC                            36

( 2 ) INFORMATION FOR SEQ ID NO:19:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

TCCTAAAGTA CTGTACAGAC TGTGATGAAA TACAATTTAA GGAGGATG               48

( 2 ) INFORMATION FOR SEQ ID NO:20:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

GGAAGTACAG GAAGTTTCTG CCTCTTACAA TGGAGTC                           37

( 2 ) INFORMATION FOR SEQ ID NO:21:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:21:

CTTGAGCTCC ACATTGGAGC ATCAGGTAGC GTCTCACCAC                        40

( 2 ) INFORMATION FOR SEQ ID NO:22:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:22:

AGTGATTGAC CTAACCATAG ACAGTTCATC TGATGAAGAG GA        42

( 2 ) INFORMATION FOR SEQ ID NO:23:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:23:

CCAAGAGGAC CTGTCCTTCC CTATCTCCCA CATCACCACT        40

( 2 ) INFORMATION FOR SEQ ID NO:24:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:24:

CTTCCACATC AAGCATCTCC AGTATCCCGC ACCCCAAGCC TTC        43

( 2 ) INFORMATION FOR SEQ ID NO:25:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:25:

TAATACCTCC CTCATCCAAG ACTATAGGCA TCCTTTCC        38

( 2 ) INFORMATION FOR SEQ ID NO:26:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:26:

CCATGCCTTA CGACTTACAA GGATTAGATT TCTTTCCTTT CTTATCA        47

( 2 ) INFORMATION FOR SEQ ID NO:27:

( i ) SEQUENCE CHARACTERISTICS:

(A) LENGTH: 44 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:27:

ACAACACCTC CTTGCTTGCC GCTGCAGCAG CAGCAGTTTC AGAT 44

(2) INFORMATION FOR SEQ ID NO:28:

(i) SEQUENCE CHARACTERISTICS:
(A) LENGTH: 39 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:28:

CTACACTCGT CTCGGTTTTT CCCGTATACC TCCTCACAG 39

(2) INFORMATION FOR SEQ ID NO:29:

(i) SEQUENCE CHARACTERISTICS:
(A) LENGTH: 36 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:29:

GGAGGCAGTA CTTCTCTGCC AACCACCAAT GGAAGC 36

(2) INFORMATION FOR SEQ ID NO:30:

(i) SEQUENCE CHARACTERISTICS:
(A) LENGTH: 39 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:30:

GGTTTCTTCC AACAGCCTAA GGGAAAGCCA TAGCCACAC 39

(2) INFORMATION FOR SEQ ID NO:31:

(i) SEQUENCE CHARACTERISTICS:
(A) LENGTH: 40 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:31:

CGGACACGGC ATCCATCTTT GGCATCATAC CAGACATTAT 40

(2) INFORMATION FOR SEQ ID NO:32:

(i) SEQUENCE CHARACTERISTICS:
(A) LENGTH: 41 base pairs
(B) TYPE: nucleic acid
(C) STRANDEDNESS: single
(D) TOPOLOGY: linear ( i i ) MOLECULE TYPE: DNA ( x i ) SEQUENCE DESCRIPTION: SEQ ID NO:32:

GCTGCTCCCA TCCCCACCCC AGATCGAATG AACTTGGCAG A    41

( 2 ) INFORMATION FOR SEQ ID NO:33:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:33:

GTGCTCTGTT TTACCTTACT CTGTTTAGAA AAGTATACAA GCGTG    45

( 2 ) INFORMATION FOR SEQ ID NO:34:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:34:

GAAATGTACA GAGAACAAAA CTATATTTTC AGTT    34

( 2 ) INFORMATION FOR SEQ ID NO:35:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:35:

CTTTTGTATA TAAATCTAAG ACTGCCTGTG TGATAAAACA CTTG    44

( 2 ) INFORMATION FOR SEQ ID NO:36:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:36:

CACGAGGCGG ACAGTGCGGA ACTAAAGCAA ATGG    34

( 2 ) INFORMATION FOR SEQ ID NO:37:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:37:

CAAGTGTTTT ATCACACAGG CAGTCTTAGA T    31

( 2 ) INFORMATION FOR SEQ ID NO:38:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:38:

GGACTTTGAA CATGTCGGGG ATCGCCCTCA GCAGACTCGC CCAG     44

( 2 ) INFORMATION FOR SEQ ID NO:39:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:39:

AAGACCACCC ATTTGGTTTC GTGGCTGTCC CAACA     35

( 2 ) INFORMATION FOR SEQ ID NO:40:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:40:

CTCATGAACT GGGAGAGCGC CATTCCAGGA AAGAAAGGGA C     41

( 2 ) INFORMATION FOR SEQ ID NO:41:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:41:

ACTACGGATG CTTTTCAAAG ATGATTATCC ATCTTC     36

( 2 ) INFORMATION FOR SEQ ID NO:42:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:42:

CACCCGAATG TGTACTTCGG GACAGTGTGC CTGTCCATC     39

( 2 ) INFORMATION FOR SEQ ID NO:43:

( i ) SEQUENCE CHARACTERISTICS:

(A) LENGTH: 41 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:43:

AGGACAAGGA CTGGAGGCCA GCCATCACAA TCAAACAGAT C          41

(2) INFORMATION FOR SEQ ID NO:44:

(i) SEQUENCE CHARACTERISTICS:
(A) LENGTH: 43 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:44:

TGAACCAAAT ATCCAAGACC CAGCTCAAGC AGAGGCCTAC ACG         43

(2) INFORMATION FOR SEQ ID NO:45:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:45:

AACAGAGTGG AGTACGAGAA AAGGGTCCGA GCTCAAGCCA             40

(2) INFORMATION FOR SEQ ID NO:46:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:46:

AGCGACCTTG TGGCATCGTC AGAAGGAAGG GATTGGTTTG GC          42

(2) INFORMATION FOR SEQ ID NO:47:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:47:

TTGCAAATCT AAAGTTGCTC CATACAATGA CTAGTCACCT             40

(2) INFORMATION FOR SEQ ID NO:48:

(i) SEQUENCE CHARACTERISTICS:
(A) LENGTH: 40 base pairs
(B) TYPE: nucleic acid
(C) STRANDEDNESS: single
(D) TOPOLOGY: linear ( i i ) MOLECULE TYPE: DNA ( x i ) SEQUENCE DESCRIPTION: SEQ ID NO:48:

TCTTCCATTG CCGCCGCGGG TGTGCGGTCT CGATTCGCTG    40

( 2 ) INFORMATION FOR SEQ ID NO:49:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:49:

CATACAGGGT CTCTTCTTCG GTCTTTTGTA TTTTTGATTG    40

( 2 ) INFORMATION FOR SEQ ID NO:50:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:50:

ATATTGATGT CAGTATTTCA ACTGCTGTAA AATTATAAAC    40

( 2 ) INFORMATION FOR SEQ ID NO:51:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:51:

GGGCGAGTTC CTCGCTCTGG GATGCAGGCA TGCTTCTCAC    40

( 2 ) INFORMATION FOR SEQ ID NO:52:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:52:

GGCCTCAGCT GGCTGTATGG AAATGCACCC TCCCTCCTGC GCTC    44

( 2 ) INFORMATION FOR SEQ ID NO:53:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:53:

CTTCTAGAAC CTGGGCTGTG CTGCTTTTGA GCCTCAGACC CCAGG    45

(2) INFORMATION FOR SEQ ID NO:54:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:54:

```
TCTGCGCCAC TTCCTTTGTG TTTATATGGC GTTTGTCTG TG          42
```

(2) INFORMATION FOR SEQ ID NO:55:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:55:

```
CTGTGTTGCT GTTAGAGTA AATAAACTGT TTATATA              37
```

(2) INFORMATION FOR SEQ ID NO:56:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:56:

```
TCACCACCTC AGTTATACTC TTATTCCTAG ATATTGGGA CA          42
```

(2) INFORMATION FOR SEQ ID NO:57:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:57:

```
CCTCCTCAAA TACAGAATAA AAGCTGCTAT GCCTGAGGCA T          41
```

(2) INFORMATION FOR SEQ ID NO:58:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:58:

```
TTGTTGGTCC GGCACATCAT ATTTACTAT TTGTTTGAGG TATTTG       46
```

(2) INFORMATION FOR SEQ ID NO:59:

(i) SEQUENCE CHARACTERISTICS:

( A ) LENGTH: 41 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:59:

GTGAATAATC TTGTCTTTTT ATTTAATAT ACACAGCACA G          41

( 2 ) INFORMATION FOR SEQ ID NO:60:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:60:

TAATTGCGTT TTGTGGACTT TACAACATGG CTAAACCCAT          40

( 2 ) INFORMATION FOR SEQ ID NO:61:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:61:

TAAATTGAAA TGAATTAGGC CAGAGGAGAT CAGACAT            37

( 2 ) INFORMATION FOR SEQ ID NO:62:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:62:

GAATTTAAAG TTAGTCTTGA GAGAAACTTA GGTAAAAAG          39

( 2 ) INFORMATION FOR SEQ ID NO:63:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:63:

TGTGAGAGTT GAAAGATATA AGTTCCAGAA TGTTGTGGCA          40

( 2 ) INFORMATION FOR SEQ ID NO:64:

( i ) SEQUENCE CHARACTERISTICS:
( A ) LENGTH: 47 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:64:

CTGGTTCCTA AAGACGGAGG AGACTCTCTC CCAGCACCTG ACTTCCA 47

( 2 ) INFORMATION FOR SEQ ID NO:65:

( i ) SEQUENCE CHARACTERISTICS:
      ( A ) LENGTH: 44 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:65:

TGCCTGGGCT GTTCCTAGCC TGGAGCACTG TCCCCCGTCT CGAT 44

( 2 ) INFORMATION FOR SEQ ID NO:66:

( i ) SEQUENCE CHARACTERISTICS:
      ( A ) LENGTH: 46 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:66:

ACCCCTGCAG GGGCTGCCCT CTTTTGGCCT CCCACTGTGT CCCTTC 46

( 2 ) INFORMATION FOR SEQ ID NO:67:

( i ) SEQUENCE CHARACTERISTICS:
      ( A ) LENGTH: 40 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:67:

CTGGCCTTGA ATGTCTCTTT CTCACCAGTA CCTTGCACAG 40

( 2 ) INFORMATION FOR SEQ ID NO:68:

( i ) SEQUENCE CHARACTERISTICS:
      ( A ) LENGTH: 34 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:68:

GAGGGACTTT GAACATGTCG GGGATCGCCC TCAG 34

( 2 ) INFORMATION FOR SEQ ID NO:69:

( i ) SEQUENCE CHARACTERISTICS:
      ( A ) LENGTH: 35 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:69:

GAGACATTCA AGGCCAGGCT GAGATCTAAT GCACA 35

( 2 ) INFORMATION FOR SEQ ID NO:70:

( i ) SEQUENCE CHARACTERISTICS:
        ( A ) LENGTH: 20 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:70:

```
His Tyr Asn Thr Ser Leu Leu Ala Ala Ala Ala Ala Ala Val Ser Asp
 1               5                  10                  15
Asp Gln Asp Leu
            20
```

( 2 ) INFORMATION FOR SEQ ID NO:71:

( i ) SEQUENCE CHARACTERISTICS:
        ( A ) LENGTH: 21 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:71:

```
Leu His Ser Ser Arg Phe Phe Pro Tyr Thr Ser Ser Gln Met Phe Leu
 1               5                  10                  15
Asp Gln Leu Ser Ala
            20
```

( 2 ) INFORMATION FOR SEQ ID NO:72:

( i ) SEQUENCE CHARACTERISTICS:
        ( A ) LENGTH: 19 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:72:

```
Leu Pro Pro Thr Lys Asn Gly Val Glu Pro Lys Arg Pro Ser Arg Pro
 1               5                  10                  15
Ile Asn Ile
```

( 2 ) INFORMATION FOR SEQ ID NO:73:

( i ) SEQUENCE CHARACTERISTICS:
        ( A ) LENGTH: 19 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:73:

```
Ser Leu Val Arg Leu Ser Thr Thr Val Pro Asn Thr Ile Val Val Ser
 1               5                  10                  15
Trp Thr Ala
```

( 2 ) INFORMATION FOR SEQ ID NO:74:

( i ) SEQUENCE CHARACTERISTICS:
        ( A ) LENGTH: 22 amino acids ( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:74:

```
Lys Glu Leu Tyr Arg Arg Arg Phe Pro Gln Lys Ile Met Thr Pro Ala
1               5                   10                  15
Asp Leu Ser Ile Pro Asn
            20
```

( 2 ) INFORMATION FOR SEQ ID NO:75:

( i ) SEQUENCE CHARACTERISTICS:
( A ) LENGTH: 16 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:75:

```
Lys Leu Gln Lys Leu Pro Phe Tyr Asp Leu Leu Asp Glu Leu Ile Lys
1               5                   10                  15
```

( 2 ) INFORMATION FOR SEQ ID NO:76:

( i ) SEQUENCE CHARACTERISTICS:
( A ) LENGTH: 19 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:76:

```
Glu Lys Leu Thr Ala Asp Pro Asp Ser Glu Ile Ala Thr Thr Ser Leu
1               5                   10                  15
Arg Val Ser
```

( 2 ) INFORMATION FOR SEQ ID NO:77:

( i ) SEQUENCE CHARACTERISTICS:
( A ) LENGTH: 20 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:77:

```
Leu Leu Cys Pro Leu Gly Lys Met Arg Leu Thr Ile Pro Cys Arg Ala
1               5                   10                  15
Leu Thr Cys Ser
            20
```

( 2 ) INFORMATION FOR SEQ ID NO:78:

( i ) SEQUENCE CHARACTERISTICS:
( A ) LENGTH: 19 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:78:

```
    Ile  Gly  Arg  Asn  Tyr  Ser  Met  Ala  Val  Tyr  Leu  Val  Lys  Gln  Leu  Ser
    1              5                        10                        15

Ser  Thr  Val
```

( 2 ) INFORMATION FOR SEQ ID NO:79:

( i ) SEQUENCE CHARACTERISTICS:
        ( A ) LENGTH: 20 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:79:

```
    Leu  Leu  Gln  Arg  Leu  Arg  Ala  Lys  Gly  Ile  Arg  Asn  Pro  Asp  His  Ser
    1              5                        10                        15

Arg  Ala  Leu  Ile
                    20
```

( 2 ) INFORMATION FOR SEQ ID NO:80:

( i ) SEQUENCE CHARACTERISTICS:
        ( A ) LENGTH: 20 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:80:

```
    Asp  Phe  Thr  Val  Gln  Val  Gln  Leu  Arg  Phe  Cys  Leu  Ser  Glu  Thr  Ser
    1              5                        10                        15

Cys  Pro  Gln  Glu
                    20
```

( 2 ) INFORMATION FOR SEQ ID NO:81:

( i ) SEQUENCE CHARACTERISTICS:
        ( A ) LENGTH: 19 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:81:

```
    His  Phe  Pro  Pro  Asn  Leu  Cys  Val  Lys  Val  Asn  Thr  Lys  Pro  Cys  Ser
    1              5                        10                        15

Leu  Pro  Gly
```

( 2 ) INFORMATION FOR SEQ ID NO:82:

( i ) SEQUENCE CHARACTERISTICS:
        ( A ) LENGTH: 18 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:82:

```
    Thr  Ser  Leu  Ala  Ser  Asp  Asn  Ser  Gln  Arg  Phe  Arg  Glu  Thr  Cys  Phe
    1              5                        10                        15

Ala  Phe
```

( 2 ) INFORMATION FOR SEQ ID NO:83:

( i ) SEQUENCE CHARACTERISTICS:
        ( A ) LENGTH: 18 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:83:

```
Pro  Gln  Gln  Val  Gln  Gln  Ile  Ser  Ser  Ser  Met  Asp  Ile  Ser  Gly  Thr
 1              5                        10                            15

Lys  Cys
```

( 2 ) INFORMATION FOR SEQ ID NO:84:

( i ) SEQUENCE CHARACTERISTICS:
        ( A ) LENGTH: 19 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:84:

```
Leu  Gln  Cys  Phe  Asp  Ala  Thr  Leu  Tyr  Ile  Gln  Met  Asn  Glu  Lys  Lys
 1              5                        10                            15

Pro  Thr  Trp
```

( 2 ) INFORMATION FOR SEQ ID NO:85:

( i ) SEQUENCE CHARACTERISTICS:
        ( A ) LENGTH: 19 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:85:

```
Val  Cys  Pro  Val  Cys  Asp  Lys  Lys  Ala  Pro  Tyr  Glu  His  Leu  Ile  Ile
 1              5                        10                            15

Asp  Gly  Leu
```

( 2 ) INFORMATION FOR SEQ ID NO:86:

( i ) SEQUENCE CHARACTERISTICS:
        ( A ) LENGTH: 19 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:86:

```
Glu  Ile  Leu  Lys  Tyr  Cys  Thr  Asp  Cys  Asp  Glu  Ile  Gln  Phe  Lys  Glu
 1              5                        10                            15

Asp  Gly  Thr
```

( 2 ) INFORMATION FOR SEQ ID NO:87:

( i ) SEQUENCE CHARACTERISTICS:
        ( A ) LENGTH: 20 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:87:

```
Trp Ala Pro Met Arg Ser Lys Lys Glu Val Gln Glu Val Ser Ala Ser
1               5                   10                  15
Tyr Asn Gly Val
            20
```

( 2 ) INFORMATION FOR SEQ ID NO:88:

( i ) SEQUENCE CHARACTERISTICS:
    ( A ) LENGTH: 20 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:88:

```
Asp Gly Cys Leu Ser Ser Thr Leu Glu His Gln Val Ala Ser His His
1               5                   10                  15
Gln Ser Ser Asn
            20
```

( 2 ) INFORMATION FOR SEQ ID NO:89:

( i ) SEQUENCE CHARACTERISTICS:
    ( A ) LENGTH: 22 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:89:

```
Lys Asn Lys Lys Val Glu Val Ile Asp Leu Thr Ile Asp Ser Ser Ser
1               5                   10                  15
Asp Glu Glu Glu Glu Glu
            20
```

( 2 ) INFORMATION FOR SEQ ID NO:90:

( i ) SEQUENCE CHARACTERISTICS:
    ( A ) LENGTH: 20 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:90:

```
Glu Glu Pro Ser Ala Lys Arg Thr Cys Pro Ser Leu Ser Pro Thr Ser
1               5                   10                  15
Pro Leu Asn Asn
            20
```

( 2 ) INFORMATION FOR SEQ ID NO:91:

( i ) SEQUENCE CHARACTERISTICS:
    ( A ) LENGTH: 20 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:91:

```
Lys Gly Ile Leu Ser Leu Pro His Gln Ala Ser Pro Val Ser Arg Thr
1               5                   10                  15

Pro Ser Leu Pro
            20
```

( 2 ) INFORMATION FOR SEQ ID NO:92:

( i ) SEQUENCE CHARACTERISTICS:
        ( A ) LENGTH: 20 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:92:

```
Ala Val Asp Thr Ser Tyr Ile Asn Thr Ser Leu Ile Gln Asp Tyr Arg
1               5                   10                  15

His Pro Phe His
            20
```

( 2 ) INFORMATION FOR SEQ ID NO:93:

( i ) SEQUENCE CHARACTERISTICS:
        ( A ) LENGTH: 19 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:93:

```
Thr Pro Met Pro Tyr Asp Leu Gln Gly Leu Asp Phe Phe Pro Phe Leu
1               5                   10                  15

Ser Gly Asp
```

( 2 ) INFORMATION FOR SEQ ID NO:94:

( i ) SEQUENCE CHARACTERISTICS:
        ( A ) LENGTH: 19 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:94:

```
Ser Leu Val Ser Ser Asn Ser Leu Arg Glu Ser His Ser His Thr Val
1               5                   10                  15

Thr Asn Arg
```

( 2 ) INFORMATION FOR SEQ ID NO:95:

( i ) SEQUENCE CHARACTERISTICS:
        ( A ) LENGTH: 19 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:95:

```
Ser Ser Thr Asp Thr Ala Ser Ile Phe Gly Ile Ile Pro Asp Ile Ile
1               5                   10                  15

Ser Leu Asp
```

( 2 ) INFORMATION FOR SEQ ID NO:96:

( i ) SEQUENCE CHARACTERISTICS:
        ( A ) LENGTH: 21 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:96:

```
His Ser Ser Pro Met Pro Ala Thr Leu Ser Pro Ser Thr Ile Pro Gln
 1               5                  10                  15
Leu Thr Tyr Asp Gly
            20
```

( 2 ) INFORMATION FOR SEQ ID NO:97:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:97:

```
His Pro Ala Ser Ser Pro Leu Leu Pro Val Ser Leu Leu Gly Pro Lys
 1               5                  10                  15
His Glu Leu Glu Leu Pro His
            20
```

( 2 ) INFORMATION FOR SEQ ID NO:98:

( i ) SEQUENCE CHARACTERISTICS:
        ( A ) LENGTH: 19 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:98:

```
Glu Leu Pro His Leu Thr Ser Ala Leu His Pro Val His Pro Asp Ile
 1               5                  10                  15
Lys Leu Gln
```

( 2 ) INFORMATION FOR SEQ ID NO:99:

( i ) SEQUENCE CHARACTERISTICS:
        ( A ) LENGTH: 24 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:99:

```
Phe Ala Phe Ala Leu Thr Pro Gln Gln Val Gln Gln Ile Ser Ser Ser
 1               5                  10                  15
Met Asp Ile Ser Gly Thr Lys Cys
            20
```

( 2 ) INFORMATION FOR SEQ ID NO:100:

( i ) SEQUENCE CHARACTERISTICS:
        ( A ) LENGTH: 20 amino acids
        ( B ) TYPE: amino acid ( C ) STRANDEDNESS: unknown
            ( D ) TOPOLOGY: unknown ( i i ) MOLECULE TYPE: peptide ( x i ) SEQUENCE DESCRIPTION: SEQ ID NO:100:

Pro Ala Ser Ser Pro Leu Leu Pro Val Ser Leu Leu Gly Pro Lys His
1               5                   10                  15

Glu Leu Glu His
            20

( 2 ) INFORMATION FOR SEQ ID NO:101:

( i ) SEQUENCE CHARACTERISTICS:
            ( A ) LENGTH: 59 amino acids
            ( B ) TYPE: amino acid
            ( C ) STRANDEDNESS: unknown
            ( D ) TOPOLOGY: unknown ( i i ) MOLECULE TYPE: peptide ( i x ) FEATURE:
            ( A ) NAME/KEY: Peptide
            ( B ) LOCATION: 19
            ( D ) OTHER INFORMATION: /note= "X is a peptide spacer of at
                    least one amino acid and less than 1000 amino
                    acids; and is a sequence and length selected
                    independently from the spacer located at 40.

( i x ) FEATURE:
            ( A ) NAME/KEY: Peptide
            ( B ) LOCATION: 40
            ( D ) OTHER INFORMATION: /note= "X is a peptide spacer of at
                    least one amino acid and less than 1000 amino
                    acids; and is a sequence and length selected
                    independently from the spacer located at position 19.

( x i ) SEQUENCE DESCRIPTION: SEQ ID NO:101:

Pro Gln Gln Val Gln Gln Ile Ser Ser Ser Met Asp Ile Ser Gly Thr
1               5                   10                  15

Lys Cys Xaa Glu Glu Pro Ser Ala Lys Arg Thr Cys Pro Ser Leu Ser
            20                  25                  30

Pro Thr Ser Pro Leu Asn Asn Xaa Ser Leu Val Ser Ser Asn Ser Leu
            35                  40                  45

Arg Glu Ser His Ser His Thr Val Thr Asn Arg
            50              55

( 2 ) INFORMATION FOR SEQ ID NO:102:

( i ) SEQUENCE CHARACTERISTICS:
            ( A ) LENGTH: 597 amino acids
            ( B ) TYPE: amino acid
            ( C ) STRANDEDNESS: unknown
            ( D ) TOPOLOGY: unknown ( i i ) MOLECULE TYPE: peptide ( x i ) SEQUENCE DESCRIPTION: SEQ ID NO:102:

Met Lys Ile Lys Glu Leu Tyr Arg Arg Arg Phe Pro Gln Lys Ile Met
1               5                   10                  15

Thr Pro Ala Asp Leu Ser Ile Pro Asn Val His Ser Ser Pro Met Pro
            20                  25                  30

Ala Thr Leu Ser Pro Ser Thr Ile Pro Gln Leu Thr Tyr Asp Gly His
            35                  40                  45

Pro Ala Ser Ser Pro Leu Leu Pro Val Ser Leu Leu Gly Pro Lys His
            50                  55                  60

Glu Leu Glu Leu Pro His Leu Thr Ser Ala Leu His Pro Val His Pro

```
                65                      70                      75                      80
    Asp  Ile  Lys  Leu  Gln  Lys  Leu  Pro  Phe  Tyr  Asp  Leu  Leu  Asp  Glu  Leu
                        85                      90                      95
    Ile  Lys  Pro  Thr  Ser  Leu  Ala  Ser  Asp  Asn  Ser  Gln  Arg  Phe  Arg  Glu
                        100                     105                     110
    Thr  Cys  Phe  Ala  Phe  Ala  Leu  Thr  Pro  Gln  Gln  Val  Gln  Gln  Ile  Ser
                        115                     120                     125
    Ser  Ser  Met  Asp  Ile  Ser  Gly  Thr  Lys  Cys  Asp  Phe  Thr  Val  Gln  Val
                        130                     135                     140
    Gln  Leu  Arg  Phe  Cys  Leu  Ser  Glu  Thr  Ser  Cys  Pro  Gln  Glu  Asp  His
    145                     150                     155                     160
    Phe  Pro  Pro  Asn  Leu  Cys  Val  Lys  Val  Asn  Thr  Lys  Pro  Cys  Ser  Leu
                        165                     170                     175
    Pro  Gly  Tyr  Leu  Pro  Pro  Thr  Lys  Asn  Gly  Val  Glu  Pro  Lys  Arg  Pro
                        180                     185                     190
    Ser  Arg  Pro  Ile  Asn  Ile  Thr  Ser  Leu  Val  Arg  Leu  Ser  Thr  Thr  Val
                        195                     200                     205
    Pro  Asn  Thr  Ile  Val  Val  Ser  Trp  Thr  Ala  Glu  Ile  Gly  Arg  Asn  Tyr
                        210                     215                     220
    Ser  Met  Ala  Val  Tyr  Leu  Val  Lys  Gln  Leu  Ser  Ser  Thr  Val  Leu  Leu
    225                     230                     235                     240
    Gln  Arg  Leu  Arg  Ala  Lys  Gly  Ile  Arg  Asn  Pro  Asp  His  Ser  Arg  Ala
                        245                     250                     255
    Leu  Ile  Lys  Glu  Lys  Leu  Thr  Ala  Asp  Pro  Asp  Ser  Glu  Ile  Ala  Thr
                        260                     265                     270
    Thr  Ser  Leu  Arg  Val  Ser  Leu  Leu  Cys  Pro  Leu  Gly  Lys  Met  Arg  Leu
                        275                     280                     285
    Thr  Ile  Pro  Cys  Arg  Ala  Leu  Thr  Cys  Ser  His  Leu  Gln  Cys  Phe  Asp
                        290                     295                     300
    Ala  Thr  Leu  Tyr  Ile  Gln  Met  Asn  Glu  Lys  Lys  Pro  Thr  Trp  Val  Cys
    305                     310                     315                     320
    Pro  Val  Cys  Asp  Lys  Lys  Ala  Pro  Tyr  Glu  His  Leu  Ile  Ile  Asp  Gly
                        325                     330                     335
    Leu  Phe  Met  Glu  Ile  Leu  Lys  Tyr  Cys  Thr  Asp  Cys  Asp  Glu  Ile  Gln
                        340                     345                     350
    Phe  Lys  Glu  Asp  Gly  Thr  Trp  Ala  Pro  Met  Arg  Ser  Lys  Lys  Glu  Val
                        355                     360                     365
    Gln  Glu  Val  Ser  Ala  Ser  Tyr  Asn  Gly  Val  Asp  Gly  Cys  Leu  Ser  Ser
                        370                     375                     380
    Thr  Leu  Glu  His  Gln  Val  Ala  Ser  His  His  Gln  Ser  Ser  Asn  Lys  Asn
    385                     390                     395                     400
    Lys  Lys  Val  Glu  Val  Ile  Asp  Leu  Thr  Ile  Asp  Ser  Ser  Ser  Asp  Glu
                        405                     410                     415
    Glu  Glu  Glu  Glu  Pro  Ser  Ala  Lys  Arg  Thr  Cys  Pro  Ser  Leu  Ser  Pro
                        420                     425                     430
    Thr  Ser  Pro  Leu  Asn  Asn  Lys  Gly  Ile  Leu  Ser  Leu  Pro  His  Gln  Ala
                        435                     440                     445
    Ser  Pro  Val  Ser  Arg  Thr  Pro  Ser  Leu  Pro  Ala  Val  Asp  Thr  Ser  Tyr
                        450                     455                     460
    Ile  Asn  Thr  Ser  Leu  Ile  Gln  Asp  Tyr  Arg  His  Pro  Phe  His  Met  Thr
    465                     470                     475                     480
    Pro  Met  Pro  Tyr  Asp  Leu  Gln  Gly  Leu  Asp  Phe  Phe  Pro  Phe  Leu  Ser
                        485                     490                     495
```

```
Gly Asp Asn Gln His Tyr Asn Thr Ser Leu Leu Ala Ala Ala Ala Ala
            500             505             510

Ala Val Ser Asp Asp Gln Asp Leu Leu His Ser Ser Arg Phe Phe Pro
        515             520             525

Tyr Thr Ser Ser Gln Met Phe Leu Asp Gln Leu Ser Ala Gly Gly Ser
    530             535             540

Thr Ser Leu Pro Thr Thr Asn Gly Ser Ser Ser Gly Ser Asn Ser Ser
545             550             555                     560

Leu Val Ser Ser Asn Ser Leu Arg Glu Ser His Ser His Thr Val Thr
            565             570             575

Asn Arg Ser Ser Thr Asp Thr Ala Ser Ile Phe Gly Ile Ile Pro Asp
            580             585             590

Ile Ile Ser Leu Asp
            595
```

( 2 ) INFORMATION FOR SEQ ID NO:103:

( i ) SEQUENCE CHARACTERISTICS:
      ( A ) LENGTH: 152 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:103:

```
Glu Leu Pro His Leu Thr Ser Ala Leu His Pro Val His Pro Asp Ile
1               5                   10                  15

Lys Leu Gln Lys Leu Pro Phe Tyr Asp Leu Leu Asp Glu Leu Ile Lys
            20              25                  30

Pro Thr Ser Leu Ala Ser Asp Asn Ser Gln Arg Phe Arg Glu Thr Cys
        35              40                  45

Phe Ala Phe Ala Leu Thr Pro Gln Gln Val Gln Gln Ile Ser Ser Ser
    50              55                  60

Met Asp Ile Ser Gly Thr Lys Cys Asp Phe Thr Val Gln Val Gln Leu
65              70                  75                  80

Arg Phe Cys Leu Ser Glu Thr Ser Cys Pro Gln Glu Asp His Phe Pro
                85              90                  95

Pro Asn Leu Cys Val Lys Val Asn Thr Lys Pro Cys Ser Leu Pro Gly
            100             105                 110

Tyr Leu Pro Pro Thr Lys Asn Gly Val Glu Pro Lys Arg Pro Ser Arg
        115             120                 125

Pro Ile Asn Ile Thr Ser Leu Val Arg Leu Ser Thr Thr Val Pro Asn
    130             135                 140

Thr Ile Val Val Ser Trp Thr Ala
145             150
```

( 2 ) INFORMATION FOR SEQ ID NO:104:

( i ) SEQUENCE CHARACTERISTICS:
      ( A ) LENGTH: 19 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:104:

```
Gly Thr Leu Asn Met Ser Gly Ile Ala Leu Ser Arg Leu Ala Gln Glu
1               5                   10                  15
```

Arg Lys Ala ( 2 ) INFORMATION FOR SEQ ID NO:105:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:105:

Asp His Pro Phe Gly Phe Val Ala Val Pro Thr Lys Asn Pro Asp Gly
1               5                   10                  15

Thr Met Asn Leu Met Asn Trp
            20

( 2 ) INFORMATION FOR SEQ ID NO:106:

( i ) SEQUENCE CHARACTERISTICS:
        ( A ) LENGTH: 24 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:106:

Thr Pro Trp Glu Gly Gly Leu Phe Lys Leu Arg Met Leu Phe Lys Asp
1               5                   10                  15

Asp Tyr Pro Ser Ser Pro Pro Lys
            20

( 2 ) INFORMATION FOR SEQ ID NO:107:

( i ) SEQUENCE CHARACTERISTICS:
        ( A ) LENGTH: 20 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:107:

Val Tyr Phe Gly Thr Val Cys Leu Ser Ile Leu Glu Glu Asp Lys Asp
1               5                   10                  15

Trp Arg Pro Ala
            20

( 2 ) INFORMATION FOR SEQ ID NO:108:

( i ) SEQUENCE CHARACTERISTICS:
        ( A ) LENGTH: 25 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:108:

Gln Glu Leu Leu Asn Glu Pro Asn Ile Gln Asp Pro Ala Gln Ala Glu
1               5                   10                  15

Ala Tyr Thr Ile Tyr Cys Gln Asn Arg
            20                  25

( 2 ) INFORMATION FOR SEQ ID NO:109:

( i ) SEQUENCE CHARACTERISTICS:
  ( A ) LENGTH: 17 amino acids
  ( B ) TYPE: amino acid
  ( C ) STRANDEDNESS: unknown
  ( D ) TOPOLOGY: unknown ( i i ) MOLECULE TYPE: peptide ( x i ) SEQUENCE DESCRIPTION: SEQ ID NO:109:

Ala Gln Ala Lys Asn Leu Arg Pro His Lys Gln Arg Pro Cys Gly Ile
1               5                   10                  15
Val ( 2 ) INFORMATION FOR SEQ ID NO:110:

( i ) SEQUENCE CHARACTERISTICS:
  ( A ) LENGTH: 25 amino acids
  ( B ) TYPE: amino acid
  ( C ) STRANDEDNESS: unknown
  ( D ) TOPOLOGY: unknown ( i i ) MOLECULE TYPE: peptide ( x i ) SEQUENCE DESCRIPTION: SEQ ID NO:110:

Arg Val Cys Gly Leu Asp Ser Leu Asn Cys Pro Phe Pro Tyr Arg Val
1               5                   10                  15
Ser Ser Ser Val Phe Cys Ile Phe Asp
            20                  25

( 2 ) INFORMATION FOR SEQ ID NO:111:

( i ) SEQUENCE CHARACTERISTICS:
  ( A ) LENGTH: 24 amino acids
  ( B ) TYPE: amino acid
  ( C ) STRANDEDNESS: unknown
  ( D ) TOPOLOGY: unknown ( i i ) MOLECULE TYPE: peptide ( x i ) SEQUENCE DESCRIPTION: SEQ ID NO:111:

Leu Phe Lys Leu Arg Met Leu Phe Lys Asp Asp Tyr Pro Ser Ser Pro
1               5                   10                  15
Pro Lys Cys Lys Phe Glu Pro Pro
            20

( 2 ) INFORMATION FOR SEQ ID NO:112:

( i ) SEQUENCE CHARACTERISTICS:
  ( A ) LENGTH: 20 amino acids
  ( B ) TYPE: amino acid
  ( C ) STRANDEDNESS: unknown
  ( D ) TOPOLOGY: unknown ( i i ) MOLECULE TYPE: peptide ( x i ) SEQUENCE DESCRIPTION: SEQ ID NO:112:

Arg Lys Ala Trp Arg Lys Asp His Pro Phe Gly Phe Val Ala Val Pro
1               5                   10                  15
Thr Lys Asn Pro
            20

( 2 ) INFORMATION FOR SEQ ID NO:113:

( i ) SEQUENCE CHARACTERISTICS:
  ( A ) LENGTH: 22 amino acids
  ( B ) TYPE: amino acid
  ( C ) STRANDEDNESS: unknown (D) TOPOLOGY: unknown (ii) MOLECULE TYPE: peptide (xi) SEQUENCE DESCRIPTION: SEQ ID NO:113:

```
Asn Ile Gln Asp Pro Ala Gln Ala Glu Ala Tyr Thr Ile Tyr Cys Gln
1               5                   10                  15
Asn Arg Val Glu Tyr Glu
            20
```

(2) INFORMATION FOR SEQ ID NO:114:

(i) SEQUENCE CHARACTERISTICS:
        (A) LENGTH: 20 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:114:

```
Gly Leu Val Trp Gln Glu Leu Val Tyr Asn Ile Phe Ala Asn Leu Lys
1               5                   10                  15
Leu Leu His Thr
            20
```

(2) INFORMATION FOR SEQ ID NO:115:

(i) SEQUENCE CHARACTERISTICS:
        (A) LENGTH: 20 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:115:

```
Gly Leu Asp Ser Leu Asn Cys Pro Phe Pro Tyr Arg Val Ser Ser Ser
1               5                   10                  15
Val Phe Cys Ile
            20
```

(2) INFORMATION FOR SEQ ID NO:116:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:116:

```
Lys Leu Ala Phe Ile Leu Ile Leu Met Ser Val Phe Gln Leu
1               5                   10
```

(2) INFORMATION FOR SEQ ID NO:117:

(i) SEQUENCE CHARACTERISTICS:
        (A) LENGTH: 61 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Peptide
        (B) LOCATION: 17

(D) OTHER INFORMATION: /note= "X is a peptide spacer of at
least one amino acid and less than 1000 amino
acids; and is a sequence and length selected
independently from the spacer located at position 40.

(ix) FEATURE:
(A) NAME/KEY: Peptide
(B) LOCATION: 40
(D) OTHER INFORMATION: /note= "X is a peptide spacer of at
least one amino acid and less than 1000 amino
acids; and is a sequence and length selected
independently from the spacer located at position 17.

(xi) SEQUENCE DESCRIPTION: SEQ ID NO:117:

```
Thr Leu Asn Met Ser Gly Ile Ala Leu Ser Arg Leu Ala Gln Glu Arg
 1               5                  10                  15
Xaa Gly Ile Gln Glu Leu Leu Asn Glu Pro Asn Ile Gln Asp Pro Ala
            20                  25                  30
Gln Ala Glu Ala Tyr Thr Ile Xaa Ala Gly Met Leu Leu Thr Val Gln
        35                  40                  45
Ser Cys Thr Trp Pro Gln Leu Ala Val Trp Lys Cys Thr
        50                  55              60
```

(2) INFORMATION FOR SEQ ID NO:118:

(i) SEQUENCE CHARACTERISTICS:
(A) LENGTH: 253 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:118:

```
Arg Gly Thr Leu Asn Met Ser Gly Ile Ala Leu Ser Arg Leu Ala Gln
 1               5                  10                  15
Glu Arg Lys Ala Trp Arg Lys Asp His Pro Phe Gly Phe Val Ala Val
            20                  25                  30
Pro Thr Lys Asn Pro Asp Gly Thr Met Asn Leu Met Asn Trp Glu Ser
        35                  40                  45
Ala Ile Pro Gly Lys Lys Gly Thr Pro Trp Glu Gly Gly Leu Phe Lys
    50                  55                  60
Leu Arg Met Leu Phe Lys Asp Tyr Pro Ser Ser Pro Pro Lys Cys
65                  70                  75              80
Lys Phe Glu Pro Pro Leu Phe His Pro Asn Val Tyr Phe Gly Thr Val
                    85                  90                  95
Cys Leu Ser Ile Leu Glu Glu Asp Lys Asp Trp Arg Pro Ala Ile Thr
                100                 105                 110
Ile Lys Gln Ile Leu Leu Gly Ile Gln Glu Leu Leu Asn Glu Pro Asn
            115                 120                 125
Ile Gln Asp Pro Ala Gln Ala Glu Ala Tyr Thr Ile Tyr Cys Gln Asn
    130                 135                 140
Arg Val Glu Tyr Glu Lys Arg Val Arg Ala Gln Ala Lys Asn Leu Arg
145                 150                 155                 160
Pro His Lys Gln Arg Pro Cys Gly Ile Val Arg Arg Lys Gly Leu Val
                    165                 170                 175
Trp Gln Glu Leu Val Tyr Asn Ile Phe Ala Asn Leu Lys Leu Leu His
                180                 185                 190
Thr Met Thr Ser His Leu Gly Gly Leu Gly Gly Arg His Leu Pro Leu
            195                 200                 205
Pro Pro Arg Val Cys Gly Leu Asp Ser Leu Asn Cys Pro Phe Pro Tyr
```

```
                          210                         215                         220
     Arg  Val  Ser  Ser  Ser  Val  Phe  Cys  Ile  Phe  Asp  Cys  Tyr  Val  Lys  Leu
     225                         230                         235                         240

Ala  Phe  Ile  Leu  Ile  Leu  Met  Ser  Val  Phe  Gln  Leu  Leu
                              245                         250
```

( 2 ) INFORMATION FOR SEQ ID NO:119:

( i ) SEQUENCE CHARACTERISTICS:
        ( A ) LENGTH: 15 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:119:

```
     Glu  Leu  Pro  His  Leu  Thr  Ser  Ala  Leu  His  Pro  Val  His  Pro  Asp
     1                   5                              10                          15
```

( 2 ) INFORMATION FOR SEQ ID NO:120:

( i ) SEQUENCE CHARACTERISTICS:
        ( A ) LENGTH: 399 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:120:

```
CACAGAAAAT   CATGACGCCT   GCAGACTTGT   CCATCCCCAA   CGTACATTCA   AGTCCTATGC        60
CAGCAACTTT   GTCTCCATCT   ACCATTCCAC   AACTCACTTA   CGATGGTCAC   CCTGCATCAT       120
CGCCATTACT   CCCTGTTTCT   CTTCTGGGAC   CTAAACATGA   ACTGGAACTC   CCACATCTTA       180
CATCAGCTCT   TCACCCAGTC   CATCCGGATA   TAAAACTTCA   AAAATTACCA   TTTTATGATT       240
TACTGGATGA   ACTGATAAAA   CCCACCAGTC   TAGCATCAGA   CAACAGTCAG   CGCTTTCGAG       300
AAACCTGTTT   TGCATTTGCC   TTGACACCAC   AACAAGTGCA   GCAAATCAGT   AGTTCCATGG       360
ATATTTCTGG   GACCAAATGT   GACTTCACAG   TACAGGTCC                                  399
```

( 2 ) INFORMATION FOR SEQ ID NO:121:

( i ) SEQUENCE CHARACTERISTICS:
        ( A ) LENGTH: 351 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:121:

```
CTGACTTGTC   CATCCCCAAC   GTACATTCAA   GTCCTATGCC   AGCAACTTTG   TCTCCATCTA        60
CCATTCCACA   ACTCACTTAC   GATGGTCACC   CTGCATCATC   GCCATTACTC   CCTGTTTCTC       120
TTCTGGGACC   TAAACATGAA   CTGGAACTCC   CACATCTTAC   ATCAGCTCTT   CACCCAGTCC       180
ATCCGGATAT   AAAACTTCAA   AAATTACCAT   TTTATGATTT   ACTGGATGAA   CTGATAAAAC       240
CCACCAGTCT   AGCATCAGAC   AACAGTCAGC   GCTTTCGAGA   AACCTGTTTT   GCATTTGCCT       300
TGACACCACA   ACAAGTNGCA   GCAAATCAGT   AGTTCCATGG   GTATTTCTGG   G                351
```

( 2 ) INFORMATION FOR SEQ ID NO:122:

( i ) SEQUENCE CHARACTERISTICS:

(A) LENGTH: 539 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:122:

```
Leu Leu Gly Pro Lys His Glu Leu Glu Pro His Leu Thr Ser Ala
 1               5                  10                  15

Leu His Pro Val His Pro Asp Ile Lys Leu Gln Lys Leu Pro Phe Tyr
                20                  25                  30

Asp Leu Leu Asp Glu Leu Ile Lys Pro Thr Ser Leu Ala Ser Asp Asn
            35                  40                  45

Ser Gln Arg Phe Arg Glu Thr Cys Phe Ala Phe Ala Leu Thr Pro Gln
    50                  55                  60

Gln Val Gln Gln Ile Ser Ser Met Asp Ile Ser Gly Thr Lys Cys
65                  70                  75                  80

Asp Phe Thr Val Gln Val Gln Leu Arg Phe Cys Leu Ser Glu Thr Ser
                85                  90                  95

Cys Pro Gln Glu Asp His Phe Pro Pro Asn Leu Cys Val Lys Val Asn
            100                 105                 110

Thr Lys Pro Cys Ser Leu Pro Gly Tyr Leu Pro Pro Thr Lys Asn Gly
        115                 120                 125

Val Glu Pro Lys Arg Pro Ser Arg Pro Ile Asn Ile Thr Ser Leu Val
    130                 135                 140

Arg Leu Ser Thr Thr Val Pro Asn Thr Ile Val Val Ser Trp Thr Ala
145                 150                 155                 160

Glu Ile Gly Arg Asn Tyr Ser Met Ala Val Tyr Leu Val Lys Gln Leu
                165                 170                 175

Ser Ser Thr Val Leu Leu Gln Arg Leu Arg Ala Lys Gly Ile Arg Asn
            180                 185                 190

Pro Asp His Ser Arg Ala Leu Ile Lys Glu Lys Leu Thr Ala Asp Pro
        195                 200                 205

Asp Ser Glu Ile Ala Thr Thr Ser Leu Arg Val Ser Leu Leu Cys Pro
    210                 215                 220

Leu Gly Lys Met Arg Leu Thr Ile Pro Cys Arg Ala Leu Thr Cys Ser
225                 230                 235                 240

His Leu Gln Cys Phe Asp Ala Thr Leu Tyr Ile Gln Met Asn Glu Lys
                245                 250                 255

Lys Pro Thr Trp Val Cys Pro Val Cys Asp Lys Lys Ala Pro Tyr Glu
            260                 265                 270

His Leu Ile Ile Asp Gly Leu Phe Met Glu Ile Leu Lys Tyr Cys Thr
        275                 280                 285

Asp Cys Asp Glu Ile Gln Phe Lys Glu Asp Gly Thr Trp Ala Pro Met
    290                 295                 300

Arg Ser Lys Lys Glu Val Gln Glu Val Ser Ala Ser Tyr Asn Gly Val
305                 310                 315                 320

Asp Gly Cys Leu Ser Ser Thr Leu Glu His Gln Val Ala Ser His His
                325                 330                 335

Gln Ser Ser Asn Lys Asn Lys Lys Val Glu Val Ile Asp Leu Thr Ile
            340                 345                 350

Asp Ser Ser Ser Asp Glu Glu Glu Glu Pro Ser Ala Lys Arg Thr
    355                 360                 365

Cys Pro Ser Leu Ser Pro Thr Ser Pro Leu Asn Asn Lys Gly Ile Leu
370                 375                 380
```

| | | | | | | | | | | | | | | |
|---|---|---|---|---|---|---|---|---|---|---|---|---|---|---|
| Ser 385 | Leu | Pro | His | Gln | Ala 390 | Ser | Pro | Val | Ser 395 | Thr | Pro | Ser | Leu | Pro 400 |
| Ala | Val | Asp | Thr | Ser 405 | Tyr | Ile | Asn | Thr | Ser 410 | Leu | Ile | Gln | Asp | Tyr | Arg 415 |
| His | Pro | Phe | His 420 | Met | Thr | Pro | Met | Pro 425 | Tyr | Asp | Leu | Gln | Gly 430 | Leu | Asp |
| Phe | Phe | Pro 435 | Phe | Leu | Ser | Gly | Asp 440 | Asn | Gln | His | Tyr | Asn 445 | Thr | Ser | Leu |
| Leu | Ala 450 | Ala | Ala | Ala | Ala | Ala 455 | Val | Ser | Asp | Asp | Gln 460 | Asp | Leu | Leu | His |
| Ser 465 | Ser | Arg | Phe | Phe | Pro 470 | Tyr | Thr | Ser | Ser | Gln 475 | Met | Phe | Leu | Asp | Gln 480 |
| Leu | Ser | Ala | Gly | Gly 485 | Ser | Thr | Ser | Leu | Pro 490 | Thr | Thr | Asn | Gly | Ser 495 | Ser |
| Ser | Gly | Ser | Asn 500 | Ser | Ser | Leu | Val | Ser 505 | Ser | Asn | Ser | Leu | Arg 510 | Glu | Ser |
| His | Ser | His 515 | Thr | Val | Thr | Asn | Arg 520 | Ser | Ser | Thr | Asp | Thr 525 | Ala | Ser | Ile |
| Phe | Gly 530 | Ile | Ile | Pro | Asp | Ile 535 | Ile | Ser | Leu | Asp | | | | | |

(2) INFORMATION FOR SEQ ID NO:123:

(i) SEQUENCE CHARACTERISTICS:
    (A) LENGTH: 11 amino acids
    (B) TYPE: amino acid
    (C) STRANDEDNESS: single
    (D) TOPOLOGY: linear (ii) MOLECULE TYPE: DNA (xi) SEQUENCE DESCRIPTION: SEQ ID NO:123:

Glu Leu Pro His Leu Thr Ser Ala Leu His Pro
1               5                   10

(2) INFORMATION FOR SEQ ID NO:124:

(i) SEQUENCE CHARACTERISTICS:
    (A) LENGTH: 37 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:124:

GACTTGTCCA TCCCCAACGT ACATTCAAGT CCTATGC    37

(2) INFORMATION FOR SEQ ID NO:125:

(i) SEQUENCE CHARACTERISTICS:
    (A) LENGTH: 2192 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:125:

GGCACGAGGC GGACAGTGCG GAACTAAAGC AAATGGTTAT GAGCCTTAGA GTTTCTGAAC    60

TCCAAGTACT GTTGGGCTAC GCGGGAGAAA CAAGCACGGA CGCAAACACG AACTTCTCAC    120

AAAAGCCCTG CATTTGCTAA AGGCTGGCTG TAGTCCTGCT GTGCAAATGA AAATTAAGGA    180

| | | | | | |
|---|---|---|---|---|---|
| ACTCTATAGG | CGGCGGTTCC | CACAGAAAAT | CATGACGCCT | GCAGACTTGT | CCATCCCCAA | 240
| CGTACATTCA | AGTCCTATGC | CAGCAACTTT | GTCTCCATCT | ACCATTCCAC | AACTCACTTA | 300
| CGATGGTCAC | CCTGCATCAT | CGCCATTACT | CCCTGTTTCT | CTTCTGGGAC | CTAAACATGA | 360
| ACTGGAACTC | CCACATCTTA | CATCAGCTCT | TCACCCAGTC | CATCCGGATA | TAAAACTTCA | 420
| AAAATTACCA | TTTTATGATT | TACTGGATGA | ACTGATAAAA | CCCACCAGTC | TAGCATCAGA | 480
| CAACAGTCAG | CGCTTTCGAG | AAACCTGTTT | TGCATTGCC | TTGACACCAC | AACAAGTGCA | 540
| GCAAATCAGT | AGTTCCATGG | ATATTTCTGG | GACCAAATGT | GACTTCACAG | TACAGGTCCA | 600
| GTTAAGGTTT | TGTTTATCAG | AAACCAGTTG | TCCACAAGAA | GATCACTTCC | CACCCAATCT | 660
| TTGTGTGAAA | GTGAATACAA | AACCTTGCAG | CCTTCCAGGT | TACCTTCCAC | CTACAAAAAA | 720
| TGGCGTGGAA | CCAAAGCGAC | CCAGCCGACC | AATTAATATC | ACCTCACTTG | TCCGACTGTC | 780
| CACAACAGTA | CCAAACACGA | TTGTTGTTTC | TTGGACTGCA | GAAATTGGAA | GAAACTATTC | 840
| CATGGCAGTA | TATCTTGTAA | AACAGTTGTC | CTCAACAGTT | CTTCTTCAGA | GGTTACGAGC | 900
| AAAGGGAATA | AGGAATCCGG | ATCATTCTAG | AGCTTTAATT | AAAGAGAAGT | TGACTGCGGA | 960
| TCCAGACAGT | GAAATAGCTA | CAACCAGCCT | AAGGGTTTCT | CTACTATGTC | CACTTGGTAA | 1020
| AATGCGGCTG | ACAATTCCGT | GTCGGCCCT | TACATGTTCT | CATCTACAAT | GTTTGACGC | 1080
| AACTCTTTAC | ATTCAGATGA | ATGAGAAAAA | ACCAACCTGG | GTTGTCCTG | TCTGTGATAA | 1140
| GAAGGCTCCA | TATGAACACC | TTATTATTGA | TGGCTTGTTT | ATGGAAATCC | TAAAGTACTG | 1200
| TACAGACTGT | GATGAAATAC | AATTTAAGGA | GGATGGCACT | TGGGCACCGA | TGAGATCAAA | 1260
| AAGGAAGTA | CAGGAAGTTT | CTGCCTCTTA | CAATGGAGTC | GATGGATGCT | TGAGCTCCAC | 1320
| ATTGGAGCAT | CAGGTAGCGT | CTCACCACCA | GTCCTCAAAT | AAAAACAAGA | AAGTAGAAGT | 1380
| GATTGACCTA | ACCATAGACA | GTTCATCTGA | TGAAGAGGAA | GAAGAGCCAT | CTGCCAAGAG | 1440
| GACCTGTCCT | TCCCTATCTC | CCACATCACC | ACTAAATAAT | AAAGGCATTT | TAAGTCTTCC | 1500
| ACATCAAGCA | TCTCCAGTAT | CCCGCACCCC | AAGCCTTCCT | GCTGTAGACA | CAAGCTACAT | 1560
| TAATACCTCC | CTCATCCAAG | ACTATAGGCA | TCCTTTCCAC | ATGACACCCA | TGCCTTACGA | 1620
| CTTACAAGGA | TTAGATTTCT | TTCCTTTCTT | ATCAGGAGAC | AATCAGCATT | ACAACACCTC | 1680
| CTTGCTTGCC | GCTGCAGCAG | CAGCAGTTTC | AGATGATCAA | GACCTCCTAC | ACTCGTCTCG | 1740
| GTTTTCCCG | TATACCTCCT | CACAGATGTT | TCTTGATCAG | TTAAGTGCAG | GAGGCAGTAC | 1800
| TTCTCTGCCA | ACCACCAATG | GAAGCAGTAG | TGGCAGTAAC | AGCAGCCTGG | TTTCTTCCAA | 1860
| CAGCCTAAGG | GAAAGCCATA | GCCACACCGT | CACAAACAGG | AGCAGCACGG | ACACGGCATC | 1920
| CATCTTTGGC | ATCATACCAG | ACATTATTTC | ATTGGACTGA | TTCCCAGGCC | CTGCTGCTCC | 1980
| CATCCCCACC | CCAGATCGAA | TGAACTTGGC | AGAAAGAAGA | GAACTTTGTG | CTCTGTTTTA | 2040
| CCTTACTCTG | TTTAGAAAAG | TATACAAGCG | TGTTTTTTTT | CCTTTTTTTA | GGGAAAAAAT | 2100
| TAAAAGAAAT | GTACAGAGAA | CAAAACTATA | TTTTCAGTTT | TACTTTTGTA | TATAAATCTA | 2160
| AGACTGCCTG | TGTGATAAAA | CACTTGTTTA | AA | | | 2192

( 2 ) INFORMATION FOR SEQ ID NO:126:

( i ) SEQUENCE CHARACTERISTICS:
( A ) LENGTH: 1840 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:126:

```
CGAGGGACTT TGAACATGTC GGGGATCGCC CTCAGCAGAC TCGCCCAGGA GAGGAAAGCA        60
TGGAGGAAAG ACCACCCATT TGGTTTCGTG GCTGTCCCAA CAAAAAATCC CGATGGCACG       120
ATGAACCTCA TGAACTGGGA GAGCGCCATT CCAGGAAAGA AAGGGACTCC GTGGGAAGGA       180
GGCTTGTTTA AACTACGGAT GCTTTTCAAA GATGATTATC CATCTTCGCC ACCAAAATGT       240
AAATTCGAAC CACCATTATT TCACCCGAAT GTGTACTTCG GGACAGTGTG CCTGTCCATC       300
TTAGAGGAGG ACAAGGACTG GAGGCCAGCC ATCACAATCA AACAGATCCT ATTAGGAATA       360
CAGGAACTTC TAAATGAACC AAATATCCAA GACCCAGCTC AAGCAGAGGC CTACACGATT       420
TACTGCCAAA ACAGAGTGGA GTACGAGAAA AGGGTCCGAG CTCAAGCCAA GAATTTGCGC       480
CCTCATAAGC AGCGACCTTG TGGCATCGTC AGAAGGAAGG GATTGGTTTG GCAAGAACTT       540
GTTACAACA TTTTTGCAAA TCTAAAGTTG CTCCATACAA TGACTAGTCA CCTGGGGGGG       600
TTGGGCGGGC GCCATCTTCC ATTGCCGCCG CGGGTGTGCG GTCTCGATTC GCTGAATTGC       660
CCGTTTCCAT ACAGGGTCTC TTCTTCGGTC TTTTGTATTT TTGATTGTTA TGTAAAACTC       720
GCTTTTATTT TAATATTGAT GTCAGTATTT CAACTGCTGT AAAATTATAA ACTTTTATAC       780
TTGGGTAAGT CCCCCAGGGC GAGTTCCTCG CTCTGGGATG CAGGCATGCT TCTCACCGTG       840
CAGAGCTGCA CTTGGCCTCA GCTGGCTGTA TGGAAATGCA CCCTCCCTCC TGCGCTCCTC       900
TCTAGAACCT TCTAGAACCT GGGCTGTGCT GCTTTGAGC CTCAGACCCC AGGGCAGCAT       960
CTCGGTTCTG CGCCACTTCC TTTGTGTTTA TATGGCGTTT TGTCTGTGTT GCTGTTTAGA      1020
GTAAATAAAC TGTTTATATA AAAAAAAAA AAAAAAAGT CCGAATTGCG CACGAGGCGC       1080
TATCACCACC TCAGTTATAC TCTTATTCCT AGATATTTGG GACATAAGAA CCAAAATCTA      1140
AAAATTAAGA GGTTTCCTCC TCAAATACAG AATAAAAGCT GCTATGCCTG AGGCATACAG      1200
GGCTTTGTTG GTCCGGCACA TCATATTTTA CTATTTGTTT GAGGTATTTG CCGAATCTTG      1260
TTAATAACAG TGAATAATCT TGTCTTTTTA TTTAATATA CACAGCACAG TAAAGAAAAG      1320
CATTAATTGC GTTTTGTGGA CTTTACAACA TGGCTAAACC CATATTCTTA GATTTGGACA      1380
TAGATAGATG CTTAGTAAAT ACTAAATTGA AATGAATTAG GCCAGAGGAG ATCAGACATA      1440
GGAATTTAAA GTTAGTCTTG AGAGAAACTT AGGTAAAAAG AAAAACAAAA TTAAAGGAGG      1500
ACTGTGTGTG AGAGTTGAAA GATATAAGTT CCAGAATGTT GTGGCAGGAC AGTGAAATCT      1560
TCTGGTTCCT AAAGACGGAG GAGACTCTCT CCCAGCACCT GACTTCCACC CTCCCACTAC      1620
TGCCAGACCT TTGCCTGGGC TGTTCCTAGC CTGGAGCACT GTCCCCGTC TCGATCCTGC      1680
CTTCCCCTGA AACCCCTGCA GGGGCTGCCC TCTTTTGGCC TCCCACTGTG TCCCTTCTCT      1740
CATGTGCATT AGATCTCAGC CTGGCCTTGA ATGTCTCTTT CTCACCAGTA CCTTGCACAG      1800
TAAACATTCA AACTTACTGT GAATTCATCT GAAAAAAAA                             1840
```

P53-BINDING POLYPEPTIDES AND POLYNUCLEOTIDES ENCODING SAME

CROSS-REFERENCE TO RELATED APPLICATION

This application is a continuation-in-part of U.S. Ser. No. 08/156,571 filed 22 Nov. 1993 and PCT/US94/13499 filed 21 Nov. 1994.

TECHNICAL FIELD

The invention provides novel polypeptides which are associated with cellular proliferation and neoplastic transformation, polynucleotides encoding such polypeptides, antibodies which are reactive with such polypeptides, polynucleotide hybridization probes and PCR amplification probes for detecting polynucleotides which encode such novel polypeptides, transgenes which encode such polypeptides, homologous targeting constructs that encode such polypeptides and/or homologously integrate in or near endogenous genes encoding such polypeptides, nonhuman transgenic animals which comprise functionally disrupted endogenous genes that normally encode such polypeptides, and transgenic nonhuman animals which comprise transgenes encoding such polypeptides. The invention also provides methods for detecting neoplastic or preneoplastic conditions in a patient, methods for treating neoplastic and preneoplastic conditions, methods for screening for antineoplastic agents and carcinogens, methods for diagnostic staging of neoplasia, methods for producing cell proliferation control proteins for use as research or diagnostic reagents, methods for producing antibodies reactive with the novel polypeptides, and methods for producing transgenic nonhuman animals expressing the novel polypeptides encoded by a transgene.

BACKGROUND

The proliferation of normal cells is thought to be regulated by growth-promoting proto-oncogenes counterbalanced by growth-constraining tumor-suppressor genes. Mutations that potentiate the activities of proto-oncogenes create the oncogenes that force the growth of neoplastic cells.

Conversely, genetic lesions that inactivate tumor suppressor genes, generally through mutation(s) that lead to a cell being homozygous for the inactivated tumor suppressor allele, can liberate the cell from the normal replicative constraints imposed by these genes. Often, an inactivated tumor suppressor gene (e.g., p53, RB, DCC, NF-1) in combination with the formation of an activated oncogene (i.e., a proto-oncogene containing an activating structural or regulatory mutation) can yield a neoplastic cell capable of essentially unconstrained growth (i.e., a transformed cell).

While different types of genetic alterations may all lead to altered expression or function of cell-growth regulatory genes and to abnormal growth, it is generally believed that more than one event is required to lead to neoplastic transformation of a normal cell to a malignant one (Land et al. (1983) Nature 304: 596; Weinberg RA (1989) Cancer Res. 49: 3713. The precise molecular pathways and secondary changes leading to malignant transformation for most cell types are not clear. A number of cases have been reported in which altered expression or activity of some proteins, such as the tumor suppressor gene protein p53, appears to be causally linked to the aberrant cell proliferation and growth control observed in neoplastic cells.

Recent advances in molecular genetics have uncovered a number of genes that exhibit structural alterations in clonal human tumors and are therefore presumed to play important roles in carcinogenesis. A variety of cancer-related genes have been classified in the broad categories of either dominantly acting oncogenes or recessive tumor suppressor genes (reviewed in Weinberg RA (1989) Cancer Res. 49: 3713 and Marshall CJ (1991) Cell 64: 313). The distinction between these two categories has been somewhat blurred by the discovery of genes that can, under appropriate assay conditions, act as either oncogenes or tumor suppressor genes. This phenomenon is exemplified by the p53 gene, whose wild-type form has tumor suppressive properties and some of whose mutants exhibit dominant oncogene-like properties (Lane DP and Benchimol S (1990) Genes Dev. 4: 1; Michalovitz et al. (1990) Cell 62: 671; Eliyahu et al. (1989) Proc. Natl. Acad. Sci. (U.S.A.) 86: 8763; Finlay et al. (1989) Cell 57: 1083; Lane DP (1992) Nature 358: 15).

The p53 gene product is a nuclear phosphoprotein involved in the control of cell proliferation, and mutations in the p53 gene are commonly found to be associated with diverse type of human cancer (Levine et al. (1991) Nature 351: 453). The p53 phosphoprotein associates with the SV40 large T antigen, adenovirus E1b protein, and human papillomavirus E6 protein, each of which are proteins implicated in the oncogenic activity of their respective viruses. These associations between p53 and viral oncoproteins may repress the activity of wild-type p53 by targeting it for rapid degradation or by sequestering it in inactive complexes (Scheffner et al. (1991) Cell 63: 1129; Oren et al. (1981) Mol. Cell. Biol. 1: 101; Yew P R and Berk A J (1992) Nature 357: 82). Wild-type p53 exhibits DNA-binding activity (Kern et al. (1991) Science 252: 1708) and transcriptional activation properties (Fields S and Jang S K (1990) Science 249: 1046; Raycroft et al. (1990) Science 249: 1049; Bargonetti et al. (1991) Cell 65: 1083; Agoff et al. (1993) Science 259: 84). Point mutated forms of p53 found associated with transformed cells have been observed to have lost the sequence-specific DNA binding function (Kern et al. (1991) op.cit; Bargonetti et al. (1991) op.cit.: El-Deiry et al. (1992) Nature Genetics 1: 45). Moreover, many of the mutant p53 proteins can act as dominant negatives to inhibit this activity of wild-type p53. Interestingly, some of the viral-encoded oncoproteins (e.g., SV40 large T antigen) also inhibit the DNA-binding activity of p53 apparently as a consequence of forming complexes with the p53 protein (Bargonetti et al. (1991) op.cit.).

A rat protein that co-immunoprecipitates with the p53 protein has been identified as the rat homologue of the mouse MDM2 protein (Barak Y and Oren M (1992) EMBO J. 11: 2115). The MDM2 gene was originally identified as a dominant transforming oncogene present on mouse double minute chromosomes; the human homologue of MDM2 has been cloned and the human MDM2 protein binds p53 (Fakharzadeh et al. (1991) EMBO J. 10: 1565; Oliner et al. (1992) Nature 358: 80).

Transgenic animals harboring a functionally disrupted p53 gene (Donehower et al. (1992) Nature 356: 215) has been described for use in carcinogen screening assays, among others.

Cell Proliferation Control and Neoplasia

Many pathological conditions result, at least in part, from aberrant control of cell proliferation, differentiation, and/or apoptosis. For example, neoplasia is characterized by a clonally derived cell population which has a diminished capacity for responding to normal cell proliferation control signals. Oncogenic transformation of cells leads to a number of changes in cellular metabolism, physiology, and morphology. One characteristic alteration of oncogenically transformed cells is a loss of responsiveness to constraints on cell proliferation and differentiation normally imposed by the appropriate expression of cell growth regulatory genes.

Despite progress in developing a more defined model of the molecular mechanisms underlying the transformed phenotype and neoplasia, few significant therapeutic methods applicable to treating cancer beyond conventional chemotherapy have resulted. The observation that aberrant p53 function is frequently correlated with neoplasia supports a model wherein p53 protein is involved in control of cell proliferation, and may be involved in one or more signalling pathways that transduce growth regulatory signals. If such a model were correct, p53 and biological macromolecules (i.e., proteins) that specifically interact with p53 would be candidate targets for therapeutic manipulation. For example and not limitation, if a hypothetical protein X bound to p53 forming a complex and thereby stimulated neoplastic growth of cells, agents that would selectively inhibit formation of the protein X: p53 complex or otherwise modulate p53 activity may be candidate antineoplastic agents.

The identification of proteins that interact with p53 protein provide a basis for screening assays for identifying agents that specifically interfere with the intermolecular association between p53 protein and such interacting proteins. These screening assays can be used to identify candidate p53 modulating agents that can serve as candidate therapeutic agents. Such p53 modulating agents can provide novel chemotherapeutic agents for treatment of neoplasia, cell proliferative conditions, arthritis, inflammation, autoimmune diseases, and the like. The present invention fulfills these and other needs.

Thus there exists a need in the art for identification and isolation of novel genes associated with neoplasia, methods for employing those genes for diagnostic and therapeutic applications, and polynucleotide constructs and transgenic animals having modified variants of such genes. The present invention fulfills these and other needs.

The references discussed herein are provided solely for their disclosure prior to the filing date of the present application. Nothing herein is to be construed as an admission that the inventors are not entitled to antedate such disclosure by virtue of prior invention.

SUMMARY OF THE INVENTION

The present invention provides several novel methods and compositions for modulating p53 activities and for screening for modulators of p53 activities. These methods utilize polynucleotide sequences encoding p53-interacting proteins and polynucleotides which are substantially identical to naturally-occurring polynucleotide sequences (e.g., cDNA or genomic gene) that encode such p53-interacting proteins.

In one aspect of the invention, p53-interacting polypeptides and compositions thereof are provided. In one embodiment, p53-interacting polypeptides comprise polypeptide sequences which are substantially identical to a sequence shown in FIG. 1A–1D, designated WBP1, or FIG. 2, designated p53UBC, or a cognate gene sequence in another species. An example of a WBP1 polypeptide is the 158 amino acid long polypeptide of SEQ ID NO: 2. An example of a p53UBC polypeptide is the 158 amino acid long polypeptide of SEQ ID NO: 4. Muteins, fragments, and other structural variants, including naturally-occurring alleleic variant are also encompassed in the invention.

Polynucleotide sequences encoding p53-interacting polypeptides are provided. The characteristics of the cloned sequences are given, including the nucleotide and predicted amino acid sequences in FIGS. 1A–1D (SEQ ID NO: 1) or FIG. 2 (SEQ ID NO: 3). Polynucleotides comprising these sequences can serve as templates for the recombinant expression of quantities of p53-interacting polypeptide polypeptides, such as human WBP1 and human p53UBC, and variants thereof, such as muteins and the like. Polynucleotides comprising these sequences can also serve as probes for nucleic acid hybridization to detect the transcription rate and mRNA abundance of p53-interacting polypeptide mRNA (e.g., WBP1 and p53UBC) in individual lymphocytes (or other cell types) by in situ hybridization, and in specific cell populations by Northern blot analysis and/or by in situ hybridization (Alwine et al.(1977) Proc. Natl. Acad. Sci. U.S.A. 74: 5350) and/or PCR amplification and/or LCR detection. Such recombinant polypeptides and nucleic acid hybridization probes have utility for in vitro screening methods for therapeutic agents (e.g., antineoplastic agents), for diagnosis and treatment of neoplastic or preneoplastic pathological conditions and genetic diseases, and for forensic identification of human individuals, among other uses apparent to those of skill in the art.

In one embodiment, candidate therapeutic agents are identified by their ability to block the binding of a p53-interacting polypeptide to a p53 polypeptide. The p53 polypeptide preferably is a full-length mature p53 protein and frequently is phosphorylated, although the phosphorylation state of individual p53 species can be variable. Typically, the p53 polypeptide comprises an amino acid sequence identical to a wild-type p53 protein sequence, although mutant p53 polypeptides are sometimes used if the mutant p53 polypeptide binds to the p53-interacting polypeptide under control assay conditions (e.g., physiological conditions). Agents are tested for their ability to alter binding between a p53 polypeptide and a p53-interacting polypeptide under suitable assay binding conditions. One means for detecting binding of a p53 polypeptide to a p53-interacting polypeptide is to immobilize the p53 polypeptide, such as by covalent or noncovalent chemical linkage to a solid support, and to contact the immobilized p53 polypeptide with a p53-interacting polypeptide that has been labeled with a detectable marker (e.g., by incorporation of radiolabeled amino acid, by epitope tagging and reporting with a fluorescent-labelled anti-epitope tag antibody, and the like). Such contacting is typically performed in aqueous conditions which permit binding of a p53 polypeptide to a p53-interacting polypeptide comprising a functional p53 binding site. Binding of the labeled p53-interacting polypeptide to the immobilized p53 is measured by determining the extent to which the labeled p53-interacting polypeptide is immobilized as a result of a specific binding interaction. Such specific binding may be reversible, or may be optionally irreversible if a cross-linking agent is added in appropriate experimental conditions. Alternatively, the p53 polypeptide may be labelled and the p53-interacting polypeptide immobilized. In one variation, the binding assay is performed with soluble (i.e., non-immobilized) p53 and p53-binding polypeptides and the resultant bound complexes (p53:p53-binding polypeptide) are separated from unbound p53 and p53-binding polypeptides, and the bound complexes are quantitated. Agents that inhibit or augment the formation of bound complexes as compared to a control binding reaction lacking agent are thereby identified as p53-modulating agents and are candidate therapeutic agents.

In one variation, the binding assay is performed in vivo in a cell, such as a yeast cell (e.g., Saccharomyces), and agents which inhibit intermolecular binding between a p53 protein and a p53-interacting polypeptide are identified as p53-modulating agents. Frequently, the in vivo screening assay is a yeast two-hybrid system wherein the yeast cells express: (1) a first fusion protein comprising p53 and a first transcriptional regulatory protein sequence (e.g., GAL4 activation domain), (2) a second fusion protein comprising a p53-interacting polypeptide and a second transcriptional regulatory protein sequence (e.g., GAL4 DNA-binding domain), and (3) a reporter gene (e.g., β-galactosidase) which is transcribed when an intermolecular complex comprising the first fusion protein and the second fusion protein is formed. If a functional p53:p53-interacting polypeptide complex forms, such as in a control assay lacking agent, the cell expresses the reporter gene which can be detected. Agents which inhibit or augment formation of functional p53:p53-interacting polypeptide complexes (and thus reporter gene expression) are thereby identified as p53-modulating agents.

The invention also provides antisense polynucleotides complementary to polynucleotides encoding p53-interacting polypeptide sequences. Such antisense polynucleotides are employed to inhibit transcription and/or translation of the p53-interacting polypeptide mRNA species and thereby effect a reduction in the amount of the respective p53-interacting polypeptide in a cell (e.g., a lymphocytic leukemia cell of a patient). Such antisense polynucleotides can function as p53-modulating agents by inhibiting the formation of p53-interacting polypeptides required for modulation of p53 function by the p53-interacting polypeptide.

In a variation of the invention, polynucleotides of the invention are employed for diagnosis of pathological conditions or genetic disease that involve neoplasia of other medical conditions related to p53 function, and more specifically conditions and diseases that involve alterations in the structure or abundance of a p53-interacting polypeptide, such as WBP1 or p53UBC.

The invention also provides antibodies which bind to Lyar with an affinity of about at least $1 \times 10^7$ $M^{-1}$ and which lack specific high affinity binding for a p53-interacting polypeptide, such as WBP1 or p53UBC. Such antibodies can be used as diagnostic reagents to identify cells exhibiting altered p53 function (e.g., preneoplastic or neoplastic cells) in a cellular sample from a patient (e.g., a lymphocyte sample, a solid tissue biopsy) as being cells which contain an increased amount of p53-interacting polypeptide as compared to non-neoplastic cells of the same cell type(s). Frequently, anti-p53-interacting polypeptide antibodies are included as diagnostic reagents for immunohistopathology staining of cellular samples in situ. Additionally, anti-p53-interacting polypeptide antibodies may be used therapeutically by targeted delivery to neoplastic cells (e.g., by cationization or by liposome/immunoliposome delivery).

The invention also provides p53-interacting polypeptide polynucleotide probes for diagnosis of disease states (e.g., neoplasia or preneoplasia) by detection of a p53-interacting polypeptide mRNA or rearrangements or amplification of the p53-interacting polypeptide gene in cells explanted from a patient, or detection of a pathognomonic p53-interacting polypeptide allele (e.g., by RFLP or allele-specific PCR analysis). Typically, the detection will be by in situ hybridization using a labeled (e.g., $^{32}P$, $^{35}S$, $^{14}C$, $^{3}H$, fluorescent, biotinylated, digoxigeninylated) p53-interacting polypeptide polynucleotide, although Northern blotting, dot blotting, or solution hybridization on bulk RNA or poly $A^+$ RNA isolated from a cell sample may be used, as may PCR amplification using p53-interacting polypeptide-specific primers. Cells which contain an altered amount of p53-interacting polypeptide mRNA as compared to non-neoplastic cells of the same cell type(s) will be identified as candidate diseased cells. Similarly, the detection of pathognomonic rearrangements or amplification of the p53-interacting polypeptide gene locus or closely linked loci in a cell sample will identify the presence of a pathological condition or a predisposition to developing a pathological condition (e.g., cancer, genetic disease). The polynucleotide probes are also used for forensic identification of individuals, such as for paternity testing or identification of criminal suspects or unknown decedents.

The present invention also provides a method for diagnosing a disease (e.g., neoplasia) in a human patient, wherein a diagnostic assay (e.g., immunohistochemical staining of fixed cells by an antibody that specifically binds human p53-interacting polypeptide) is used to determine if a predetermined pathognomonic concentration of p53-interacting polypeptide or its encoding mRNA is present in a biological sample from a human patient; if the assay indicates the presence of p53-interacting polypeptide or its encoding mRNA outside of the normal range (e.g., beyond the predetermined pathognomonic concentration), the patient is diagnosed as having a disease condition or predisposition.

The invention also provides therapeutic agents which inhibit neoplasia or apoptosis by modulating p53 function by inhibiting or augmenting formation of complexes of p53:p53-interacting polypeptide, such agents can be used as pharmaceuticals. Such pharmaceuticals will be used to treat a variety of human and veterinary diseases, such as: reperfusion injury, myocardial infarction, stroke, traumatic brain injury, neurodegenerative diseases, aging, ischemia, toxemia, infection, AIDS, hepatitis, and the like.

The invention also provides methods for identifying polypeptide sequences which bind to a p53-interacting polypeptide. By definition, one member of the set of interacting proteins is p53. For example, a yeast two-hybrid screening system can be used for identifying polypeptide sequences that bind to WBP1 or p53UBC. Yeast two-hybrid systems wherein one GAL4 fusion protein comprises a p53-interacting polypeptide sequence, typically a full-length of near full-length WBP1 or P53UBC polypeptide sequence (e.g., a polypeptide sequence of FIGS. 1A-D or 2), and the other GAL4 fusion protein comprises a cDNA library member can be used to identify cDNAs encoding proteins which interact with the p53-interacting polypeptide, can be screened according to the general method of Chien et al. (1991) op.cit. Alternatively, an *E. coli*/BCCP interactive screening system (Germino et al. (1993) *Proc. Natl. Acad. Sci. (U.S.A.)* 90: 933; Guarente L (1993) *Proc. Natl. Acad. Sci. (U.S.A.)* 90: 1639, incorporated herein by reference) can be used to identify interacting protein sequences. Also, an expression library, such as a λgt11 cDNA expression library, can be screened with a labelled p53-interacting polypeptide to identify cDNAs encoding polypeptides which specifically bind to the p53-interacting polypeptide. For these procedures, cDNA libraries usually comprise mammalian cDNA populations, typically human, mouse, or rat, and may represent cDNA produced from RNA of one cell type, tissue, or organ and one or more developmental stage. Specific binding for screening cDNA expression libraries is usually provided by including one or more blocking agent (e.g., albumin, nonfat dry milk solids, etc.) prior to and/or concomitant with contacting the labeled p53-interacting polypeptide (and/or labeled anti-p53-interacting polypeptide antibody).

BRIEF DESCRIPTION OF THE DRAWINGS

FIGS. 1A–1D (SEQ. ID NOS: 1 and 2) show the nucleotide sequence and deduced amino acid sequence of human WBP1.

FIG. 2 (SEQ. ID NOS: 3) shows the nucleotide sequence and deduced amino acid sequence of human p53UBC. The translational frame is shown as the deduced amino acid sequence of the p53UBC protein.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, the twenty conventional amino acids and their abbreviations follow conventional usage (*Immunology - A Synthesis*, 2nd Edition, E. S. Golub and D. R. Gren, Eds., Sinauer Associates, Sunderland, Mass. (1991), which is incorporated herein by reference). Stereoisomers (e.g., D-amino acids) of the twenty conventional amino acids, unnatural amino acids such as α, α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N ,N, N-trimethyllysine, ε-N-acetyllysine, O-phosphoserine, N-acetylserine, N-formylmethionine, 3 -methylhistidine, 5-hydroxylysine, ω-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence of FIGS. 1A–1D or FIG. 2, or may comprise a complete cDNA or gene sequence.

Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci. (U.S.A.)* 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wisc.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the human WBP1 polynucleotide sequence shown in FIGS. 1A–1D or the human p53UBC polynucleotide sequence shown in FIG. 2.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "WBP1 native protein" and "p53UBC native protein" as used herein refers to a naturally-occurring WBP1 or p53UBC polypeptide corresponding to the deduced amino acid sequence shown in FIGS. 1A–1D or 2, respectively, or corresponding to the deduced amino acid sequence of a WBP1 or p53UBC full-length cDNA produced from a mammalian mRNA sample, such as a human mRNA sample. Also for example, a native WBP1 or p53UBC protein present in naturally-occurring human cells which express the WBP1 or p53UBC gene are considered full-length proteins.

The term "fragment" as used herein refers to a polypeptide that has an amino-terminal and/or carboxy-terminal deletion, but where the remaining amino acid sequence is identical to the corresponding positions in the naturally-occurring (e.g., mature protein) sequence deduced, for example, from a full-length cDNA sequence (e.g., the CDNA sequence shown in FIGS. 1A–1D or 2). Fragments typically are at least 14 amino acids long, preferably at least 20 amino acids long, usually at least 50 amino acids long or longer.

The term "analog" as used herein refers to polypeptides which are comprised of a segment of at least 25 amino acids that has substantial identity to a portion of the deduced amino acid sequence shown in FIGS. 1A–1D or FIG. 2, and which has at least one of the following properties: (1) specific binding to a p53 polypeptide (e.g., human p53 phosphoprotein) under suitable binding conditions, or (2) ability to modulate p53 activity when expressed in a mammalian cell (e.g., mimic a p53 mutant phenotype). Typically, analog polypeptides comprise a conservative amino acid substitution (or addition or deletion) with respect to the naturally-occurring sequence. Analogs typically are at least 20 amino acids long, preferably at least 50 amino acids long or longer, most usually being as long as full-length naturally-occurring p53-interacting polypeptide (e.g., as shown in FIGS. 1A–1D or 2). Some p53-interacting polypeptide analogs may lack biological activity but may still be employed for various uses, such as for raising antibodies to p53-interacting polypeptide epitopes, as an immunological reagent to detect and/or purify α-p53-interacting polypeptide antibodies by affinity chromatography, or as a competitive or noncompetitive agonist, antagonist, or partial agonist of native p53-interacting polypeptide function.

The term "polypeptide" is used herein as a generic term to refer to native protein, fragments, or analogs of a polypeptide sequence. Hence, native protein, fragments, and analogs are species of the polypeptide genus. Preferred p53-interacting polypeptides include: the human full-length protein comprising the polypeptide sequence shown in FIGS. 1A–1D or 2, or polypeptides consisting essentially of a sequence shown in Table III or Table IV.

The term "cognate" as used herein refers to a gene sequence that is evolutionarily and functionally related between species. For example but not limitation, in the human genome, the human CD4 gene is the cognate gene to the mouse CD4 gene, since the sequences and structures of these two genes indicate that they are highly homologous and both genes encode a protein which functions in signaling T cell activation through MHC class II-restricted antigen recognition. Thus, the cognate murine gene to the human WBP1 gene is the murine gene which encodes an expressed protein which has the greatest degree of sequence identity to the human WBP1 protein and which exhibits an expression pattern similar to that of the human WBP1 gene. Preferred cognate WBP1 and p53UBC genes are: rat WBP1 or p53UBC, rabbit WBP1 or p53UBC, canine WBP1 or p53UBC, nonhuman primate WBP1 or p53UBC, porcine WBP1 or p53UBC, bovine WBP1 or p53UBC, murine WBP1 or p53UBC, and hamster WBP1 or p53UBC.

The term "modulation of p53" is used herein to refer to the capacity to either enhance or inhibit a functional property of p53 (e.g., DNA-binding activity, transcriptional enhancement activity, cell replication phenotype); such enhancement or inhibition may be contingent on the occurrence of a specific event, such as activation of a signal transduction pathway, and/or may be manifest only is particular cell types. The altered ability of p53 to modulate transcriptional enhancement or inhibition may affect the inducible transcription of a gene or may effect the basal level transcription of a gene, or both.

The term "agent" is used herein to denote a chemical compound, a mixture of chemical compounds, a biological macromolecule, or an extract made from biological materials such as bacteria, plants, fungi, or animal (particularly mammalian) cells or tissues. Agents are evaluated for potential activity as p53 modulatory agents (e.g., antineoplastic agents, cytotoxic agents, cell proliferation-promoting agents, and the like) by inclusion in screening assays described hereinbelow.

The term "candidate agent" is used herein to refer to an agent which is identified by one or more screening method(s) of the invention as a putative p53 modulatory agent. Some candidate p53 modulatory agents may have therapeutic potential as drugs for human use.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). Various methods of labeling polypeptides and glycoproteins are known in the art and may be used. Examples of labels for polypeptides include, but are not limited to, the following: radioisotopes (e.g., $^3$H, $^{14}$C, $^{35}$S, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

As used herein, "substantially pure" means an object species is the predominant species present (i.e., on a molar basis it is more abundant than any other individual macromolecular species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

As used herein the terms "pathognomonic concentration", "pathognomonic amount", and "pathognomonic staining pattern" refer to a concentration, amount, or localization pattern, respectively, of a p53-interacting polypeptide or mRNA in a sample, that indicates the presence of a disease condition or a predisposition to developing a disease, such as neoplasia or senescence. A pathognomonic amount is an amount of a p53-interacting polypeptide or encoding mRNA in a cell or cellular sample that falls outside the range of normal clinical values that is established by prospective and/or retrospective statistical clinical studies. Generally, an individual having a disease (e.g., neoplasia) will exhibit an amount of a p53-interacting polypeptide or mRNA in a cell or tissue sample that is significantly higher or lower than the range of concentrations that characterize normal, undiseased individuals; typically the pathognomonic concentration is at least about one standard deviation above or below the mean normal value, more usually it is at least about two standard deviations or more above or below the mean normal value. However, essentially all clinical diagnostic tests produce some percentage of false positives and false negatives. The sensitivity and selectivity of the diagnostic assay must be sufficient to satisfy the diagnostic objective and any relevant regulatory requirements. In general, the diagnostic methods of the invention are used to identify individuals as disease candidates, providing an additional parameter in a differential diagnosis of disease made by a competent health professional.

DETAILED DESCRIPTION

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y., which is incorporated herein by reference) which are provided throughout this document. The procedures therein are believed to be well known in the art and are provided for the convenience of the reader. All the information contained therein is incorporated herein by reference.

Oligonucleotides can be synthesized on an Applied Bio Systems oligonucleotide synthesizer according to specifications provided by the manufacturer.

Methods for PCR amplification are described in the art (PCR Technology: Principles and Applications for DNA Amplification ed. H A Erlich, Freeman Press, New York, NY (1992); PCR Protocols: A Guide to Methods and Applications, eds. Innis, Gelfland, Snisky, and White, Academic Press, San Diego, Calif. (1990); Mattila et al. (1991) Nucleic Acids Res. 19: 4967; Eckert, K. A. and Kunkel, T. A. (1991) PCR Methods and Applications 1: 17; PCR, eds. McPherson, Quirkes, and Taylor, IRL Press, Oxford; and U.S. Pat. No. 4,683,202, which are incorporated herein by reference).

Co-pending applications U.S. Ser. No. 08/156,571 filed 22 Nov. 1993 and PCT/US94/13499 filed 21 Nov. 1994 are incorporated herein by reference.

Identification of p53-Interacting Polypeptide Sequences

Polypeptide sequences which interact with mammalian p53 polypeptide sequences may be identified by a variety of methods, including but not limited to: (1) co-immunoprecipitation of proteins associated with p53 in extracts of mammalian cells or cell nuclei, (2) screening of an expression library using a two-hybrid reporter system, such as a yeast two-hybrid system (Chien et al. (1991) Proc. Natl. Acad. Sci. (U.S.A.) 88: 9578; Zervos et al. (1993) Cell 72: 223), and (3) screening cDNA expression libraries with labeled p53 protein (or p53 protein which is subsequently detected with a labelled antibody) (Ayer et al. (1993) Cell 72: 211). Alternatively, an E. coli/BCCP interactive screening system (Germino et al. (1993) Proc. Natl. Acad. Sci. (U.S.A.) 90: 933; Guarente L (1993) Proc. Natl. Acad. Sci. (U.S.A.) 90: 1639, incorporated herein by reference) can be used to identify interacting protein sequences.

For proteins isolated by co-immunoprecipitation with p53 using and α-p53 antibody, generally the isolated p53-interacting polypeptide is purified to homogeneity and sequenced by Edman degradation. From the amino acid sequence(s) thus generated, degenerate oligonucleotide probes encoding the amino acid sequence(s) are produced and labelled for screening a cDNA or genomic library.

For polypeptide sequences identified by two-hybrid screening or CDNA library screening with p53 protein, the polynucleotide sequences encoding the p53-interacting polypeptide sequence are isolated and sequenced (e.g., by Sanger dideoxy sequencing), and the correct deduced amino acid sequence is determined.

For exemplification, the human WBP1 and p53UBC polynucleotide and deduced polypeptide sequences were isolated by screening a two-hybrid yeast expression system for polynucleotides encoding polypeptide sequences that bind to human a p53 fusion protein (see, Experimental Examples, infra).

The invention also provides methods for identifying polypeptide sequences which bind to a p53-interacting polypeptide. For example, polynucleotides encoding polypeptide sequences that bind to WBP1 or p53UBC can be identified by these methods. By definition, one member of each set of interacting proteins is p53. For example, a yeast two-hybrid screening system can be used to screen a mammalian (e.g., human) cDNA bank for identifying cDNA species which encode polypeptide sequences that bind to WBP1 or p53UBC, and will identify clones encoding p53 (wild-type) if such p53 clones are represented in the clone bank.

Cloning of WBP1 and p53UBC Polynucleotides

Genomic or cDNA clones encoding WBP1 or p53UBC conveniently may be isolated from clone libraries (e.g., available from Clontech, Palo Alto, Calif.) using hybridization probes designed on the basis of the nucleotide sequences shown in FIGS. 1A-1D and FIG. 2 and using conventional hybridization screening methods (e.g., Benton W D and Davis R W (1977) Science 196: 180; Goodspeed et al. (1989) Gene 76: 1; Dunn et al. (1989) J. Biol. Chem. 264: 13057). Where a cDNA clone is desired, clone libraries containing cDNA derived from cells expressing significant amounts of WBP1 or p53UBC mRNA is preferred. Alternatively, synthetic polynucleotide sequences corresponding to all or part of the sequences shown in FIGS. 1A-1D and 2 may be constructed by chemical synthesis of oligonucleotides. Additionally, polymerase chain reaction (PCR) using primers based on the sequence data disclosed in FIGS. 1A-1D and 2 may be used to amplify DNA fragments from genomic DNA, mRNA pools, or from cDNA clone libraries. U.S. Pat. Nos. 4,683,195 and 4,683,202 describe the PCR method. Additionally, PCR methods employing one primer that is based on the sequence data disclosed in FIGS. 1A-1D or FIG. 2 and a second primer that is not based on that sequence data may be used. For example, a second primer that is homologous to or complementary to a polyadenylation segment or randomer may be used.

It is apparent to one of skill in the art that nucleotide substitutions, deletions, and additions may be incorporated into the polynucleotides of the invention. Nucleotide sequence variation may result from sequence polymorphisms of various WBP1 or p53UBC alleles, minor sequencing errors, and the like. However, such nucleotide substitutions, deletions, and additions should not substantially disrupt the ability of the polynucleotide to hybridize to one of the polynucleotide sequences shown in FIGS. 1A-1D or 2 under hybridization conditions that are sufficiently stringent to result in specific hybridization.

Specific hybridization is defined herein as the formation of hybrids between a probe polynucleotide (e.g., a polynucleotide of the invention which may include substitutions, deletion, and/or additions) and a specific target polynucleotide (e.g., a polynucleotide having a sequence shown in FIGS. 1A-1D or FIG. 2), wherein the probe preferentially hybridizes to the specific target such that, for example, a single band corresponding to WBP1 or p53UBC mRNA (or bands corresponding to multiple alternative splicing products of the WBP1 or p53UBC gene) can be identified on a Northern blot of RNA prepared from a suitable cell source (e.g., a cell expression WBP1 or p53UBC mRNA). Polynucleotides of the invention and recombinantly produced WBP1 or p53UBC, and fragments or analogs thereof, may be prepared on the basis of the sequence data provided in FIGS. 1A-1D or FIG. 2 according to methods known in the art and described in Maniatis et al., Molecular Cloning: A Laboratory Manual, 2nd Ed., (1989), Cold Spring Harbor, N.Y. and Berger and Kimmel, Methods in Enzymology, Volume 152, Guide to Molecular Cloning Techniques (1987), Academic Press, Inc., San Diego, Calif., which are incorporated herein by reference.

WBP1 or p53UBC polynucleotides may be short oligonucleotides (e.g., 25-100 bases long), such as for use as hybridization probes and PCR (or LCR) primers. WBP1 or p53UBC polynucleotide sequences may also comprise part of a larger polynucleotide (e.g., a cloning vector comprising a WBP1 or p53UBC clone) and may be fused, by polynucleotide linkage, in frame with another polynucleotide sequence encoding a different protein (e.g., glutathione S-transferase or β-galactosidase) for encoding expression of a fusion protein. Typically, WBP1 or p53UBC polynucleotides comprise at least 25 consecutive nucleotides which are substantially identical to a naturally-occurring WBP1 or p53UBC sequence (e.g., FIGS. 1A-1D or FIG. 2), more usually WBP1 or p53UBC polynucleotides comprise at least 50 to 100 consecutive nucleotides which are substantially identical to a naturally-occurring WBP1 or p53UBC sequence. However, it will be recognized by those of skill that the minimum length of a WBP1 or p53UBC polynucleotide required for specific hybridization to a WBP1 or p53UBC, respectively, target sequence will depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others.

For example but not limitation, suitable hybridization probes for detecting and/or quantifying the presence of WBP1 mRNA in a sample generally comprise at least one, preferably at least two, frequently five, occasionally nine, and more preferably all of the following human WBP1 sequences shown in Table I, or their complements:

TABLE I

| Selected Human WBP1 Polynucleotide Sequences | |
|---|---|
| 5'-GCACGAGGCGGACAGTGCGGAACTAAAGCAAATGGTTATG-3' | (SEQ ID NO:5) |
| 5'-CTTCAAAAATTACCATTTTATGATTTACTGGATGAACT-3' | (SEQ ID NO:6) |
| 5'-CATCAGACAACAGTCAGCGCTTTCGAGAAACCTGTTTTGC-3' | (SEQ ID NO:7) |
| 5'-CACAACAAGTGCAGCAAATCAGTAGTTCCATGGATA-3' | (SEQ ID NO:8) |
| 5'-GTACAGGTCCAGTTAAGGTTTTTGTTTATCAGAAACCAGTTG-3' | (SEQ ID NO:9) |
| 5'-TGAAAGTGAATACAAAACCTTGCAGCCTTCCAGG-3' | (SEQ IS NO:10) |
| 5'-CCACCTACAAAAAATGGCGTGGAACCAAAGCGACCCAGCCGAC-3' | (SEQ ID NO:11) |
| 5'-GACTGTCCACAACAGTACCAAACACGATTGTTG-3' | (SEQ ID NO:12) |
| 5'-GGAAGAAACTATTCCATGGCAGTATATCTTGTAAAACAGT-3' | (SEQ ID NO:13) |
| 5'-CAGAGGTTACGAGCAAAGGGAATAAGGAATCCGGATCATTCTAGAG-3' | (SEQ ID NO:14) |

TABLE I-continued

Selected Human WBP1 Polynucleotide Sequences

| Sequence | ID |
|---|---|
| 5'-GGATCCAGACAGTGAAATAGCTACAACCAGCCTAAG-3' | (SEQ ID NO:15) |
| 5'-CTTGGTAAAATGCGGCTGACAATTCCGTGTCGGGCCCTTAC-3' | (SEQ ID NO:16) |
| 5'-CATCTACAATGTTTTGACGCAACTCTTTACATTCAGATG-3' | (SEQ ID NO:17) |
| 5'-GTCCTGTCTGTGATAAGAAGGCTCCATATGAACACC-3' | (SEQ ID NO:18) |
| 5'-TCCTAAAGTACTGTACAGACTGTGATGAAATACAATTTAAGGAGGATG-3' | (SEQ ID NO:19) |
| 5'-GGAAGTACAGGAAGTTTCTGCCTCTTACAATGGAGTC-3' | (SEQ ID NO:20) |
| 5'-CTTGAGCTCCACATTGGAGCATCAGGTAGCGTCTCACCAC-3' | (SEQ ID NO:21) |
| 5'-AGTGATTGACCTAACCATAGACAGTTCATCTGATGAAGAGGA-3' | (SEQ ID NO:22) |
| 5'-CCAAGAGGACCTGTCCTTCCCTATCTCCCACATCACCACT-3' | (SEQ ID NO:23) |
| 5'-CTTCCACATCAAGCATCTCCAGTATCCCGCACCCCAAGCCTTC-3' | (SEQ ID NO:24) |
| 5'-TAATACCTCCCTCATCCAAGACTATAGGCATCCTTTCC-3' | (SEQ ID NO:25) |
| 5'-CCATGCCTTACGACTTACAAGGATTAGATTTCTTTCCTTTCTTATCA-3' | (SEQ ID NO:26) |
| 5'-ACAACACCTCCTTGCTTGCCGCTGCAGCAGCAGCAGTTTCAGAT-3' | (SEQ ID NO:27) |
| 5'-CTACACTCGTCTCGGTTTTTCCCGTATACCTCCTCACAG-3' | (SEQ ID NO:28) |
| 5'-GGAGGCAGTACTTCTCTGCCAACCACCAATGGAAGC-3' | (SEQ ID NO:29) |
| 5'-GGTTTCTTCCAACAGCCTAAGGGAAAGCCATAGCCACAC-3' | (SEQ ID NO:30) |
| 5'-CGGACACGGCATCCATCTTTGGCATCATACCAGACATTAT-3' | (SEQ ID NO:31) |
| 5'-GCTGCTCCCATCCCCACCCCAGATCGAATGAACTTGGCAGA-3' | (SEQ ID NO:32) |
| 5'-GTGCTCTGTTTTACCTTACTCTGTTTAGAAAAGTATACAAGCGTG-3' | (SEQ ID NO:33) |
| 5'-GAAATGTACAGAGAACAAAACTATATTTTCAGTT-3' | (SEQ ID NO:34) |
| 5'-CTTTTGTATATAAATCTAAGACTGCCTGTGTGATAAAACACTTG-3' | (SEQ ID NO:35) |

Sequences of Table I or their complements are selected independently to form WBP1 polynucleot des useful as hybridization probes. Typically, such sequences are placed in the same orientation and order as found in the naturally-occurring WBP1 mRNA and/or gene, and may comprise one or more spacers of irrelevant sequence (e.g., pBR322, random-sequence, and the like), such spacer sequences are typically selected independently and comprise between 0-300 nucleotides (0-100 amino acids, if fused in translational frame).

Also for example but not limitation, the following pair of PCR primers (amplimers) may be used to amplify murine or human WBP1 sequences (e.g., by reverse transcriptase initiated PCR of RNA from WBP1 expressing cells):

| | |
|---|---|
| (foward) 5'-CACGAGGCGGACAGTGCGGAACTAAAGCAAATGG-3' | (SEQ ID NO:36) |
| (reverse) 5'-CAAGTGTTTTATCACACAGGCAGTCTTAGAT-3' | (SEQ ID NO: 37) |

If desired, PCR amplimers for amplifying substantially full-length cDNA copies may be selected at the discretion of the practitioner. Similarly, amplimers to amplify single WBP1 exons or portions of the WBP1 gene (murine or human) may be selected.

Each of these sequences may be used as hybridization probes or PCR amplimers to detect the presence of WBP1 mRNA, for example to diagnose a disease characterized by the presence of an elevated WBP1 mRNA level in cells, or to perform tissue typing (i.e., identify tissues characterized by the expression of WBP1 mRNA), and the like. The sequences may also be used for detecting genomic WBP1 gene sequences in a DNA sample, such as for forensic DNA analysis (e.g., by RFLP analysis, PCR product length(s) distribution, etc.) or for diagnosis of diseases characterized by amplification and/or rearrangements of the WBP1 gene.

For example but not limitation, suitable hybridization probes for detecting and/or quantifying the presence of p53UBC MRNA in a sample generally comprise at least one, preferably at least two, and more preferably all of the following human p53UBC sequences shown in Table II, or their complements:

TABLE II

Selected Human p53UBC Polynucleotide Sequences

| Sequence | ID |
|---|---|
| 5'-GGACTTTGAACATGTCGGGGATCGCCCTCAGCAGACTCGCCCAG-3' | (SEQ ID NO:38) |
| 5'-AAGACCACCCATTTGGTTTCGTGGCTGTCCCAACA-3' | (SEQ ID NO:39) |
| 5'-CTCATGAACTGGGAGAGCGCCATTCCAGGAAAGAAAGGGAC-3' | (SEQ ID NO:40) |
| 5'-ACTACGGATGCTTTTCAAAGATGATTATCCATCTTC-3' | (SEQ ID NO:41) |
| 5'-CACCCGAATGTGTACTTCGGGACAGTGTGCCTGTCCATC-3' | (SEQ ID NO:42) |
| 5'-AGGACAAGGACTGGAGGCCAGCCATCACAATCAAACAGATC-3' | (SEQ ID NO:43) |
| 5'-TGAACCAAATATCCAAGACCCAGCTCAAGCAGAGGCCTACACG-3' | (SEQ ID NO:44) |
| 5'-AACAGAGTGGAGTACGAGAAAAGGGTCCGAGCTCAAGCCA-3' | (SEQ ID NO:45) |
| 5'-AGCGACCTTGTGGCATCGTCAGAAGGAAGGGATTGGTTTGGC-3' | (SEQ ID NO:46) |
| 5'-TTGCAAATCTAAAGTTGCTCCATACAATGACTAGTCACCT-3' | (SEQ ID NO:48) |
| 5'-TCTTCCATTGCCGCCGCGGGTGTGCGGTCTCGATTCGCTG-3' | (SEQ ID NO:48) |
| 5'-CATACAGGGTCTCTTCTTCGGTCTTTTGTATTTTTGATTG-3' | (SEQ ID NO:49) |
| 5'-ATATTGATGTCAGTATTTCAACTGCTGTAAAATTATAAAC-3' | (SEQ ID NO:50) |
| 5'-GGGCGAGTTCCTCGCTCTGGGATGCAGGCATGCTTCTCAC-3' | (SEQ ID NO:51) |
| 5'-GGCCTCAGCTGGCTGTATGGAAATGCACCCTCCCTCCTGCGCTC-3' | (SEQ ID NO:52) |
| 5'-CTTCTAGAACCTGGGCTGTGCTGCTTTTGAGCCTCAGACCCCAGG-3' | (SEQ ID NO:53) |

TABLE II-continued

Selected Human p53UBC Polynucleotide Sequences

| | |
|---|---|
| 5'-TCTGCGCCACTTCCTTTGTGTTTATATGGCGTTTTGTCTGTG-3' | (SEQ ID NO:54) |
| 5'-CTGTGTTGCTGTTTAGAGTAAATAAACTGTTTATATA-3' | (SEQ ID NO:55) |
| 5'-TCACCACCTCAGTTATACTCTTATTCCTAGATATTTGGGACA-3' | (SEQ ID NO:56) |
| 5'-CCTCCTCAAATACAGAATAAAAGCTGCTATGCCTGAGGCAT-3' | (SEQ ID NO:57) |
| 5'-TTGTTGGTCCGGCACATCATATTTTACTATTTGTTTGAGGTATTTG-3' | (SEQ ID NO:58) |
| 5'-GTGAATAATCTTGTCTTTTTATTTTAATATACACAGCACAG-3' | (SEQ ID NO:59) |
| 5'-TAATTGCGTTTTGTGGACTTTACAACATGGCTAAACCCAT-3' | (SEQ ID NO:60) |
| 5'-TAAATTGAAATGAATTAGGCCAGAGGAGATCAGACAT-3' | (SEQ ID NO:61) |
| 5'-GAATTTAAAGTTAGTCTTGAGAGAAACTTAGGTAAAAAG-3' | (SEQ ID NO:62) |
| 5'-TGTGAGAGTTGAAAGATATAAGTTCCAGAATGTTGTGGCA-3' | (SEQ ID NO:63) |
| 5'-CTGGTTCCTAAAGACGGAGGAGACTCTCTCCCAGCACCTGACTTCCA-3' | (SEQ ID NO:64) |
| 5'-TGCCTGGGCTGTTCCTAGCCTGGAGCACTGTCCCCCGTCTCGAT-3' | (SEQ ID NO:65) |
| 5'-ACCCCTGCAGGGGCTGCCCTCTTTTGGCCTCCCACTGTGTCCCTTC-3' | (SEQ ID NO:66) |
| 5'-CTGGCCTTGAATGTCTCTTTCTCACCAGTACCTTGCACAG-3' | (SEQ ID NO:67) |

Also for example but not limitation, the following pair of PCR primers (amplimers) may be used to amplify murine or human p53UBC sequences (e.g., by reverse transcriptase initiated PCR of RNA from p53UBC expressing cells):

| | |
|---|---|
| (foward) 5'-GAGGGACTTTGAACATGTCGGGGATCGCCCTCAG-3' | (SEQ ID NO:68) |
| (reverse) 5'-GAGACATTCAAGGCCAGGCTGAGATCTAATGCACA-3' | (SEQ ID NO:69) |

If desired, PCR amplimers for amplifying substantially full-length cDNA copies may be selected at the discretion of the practitioner. Similarly, amplimers to amplify single p53UBC exons or portions of the p53UBC gene (murine or human) may be selected.

Each of these sequences may be used as hybridization probes or PCR amplimers to detect the presence of p53UBC mRNA, for example to diagnose a disease characterized by the presence of an elevated p53UBC mRNA level in cells, or to perform tissue typing (i.e., identify tissues characterized by the expression of p53UBC mRNA), and the like. The sequences may also be used for detecting genomic p53UBC gene sequences in a DNA sample, such as for forensic DNA analysis (e.g., by RFLP analysis, PCR product length(s) distribution, etc.) or for diagnosis of diseases characterized by amplification and/or rearrangements of the p53UBC gene.

Production of WBP1 and p53UBC Polypeptides

The nucleotide and amino acid sequences shown in FIGS. 1A–1D and 2 enable those of skill in the art to produce polypeptides corresponding to all or part of the full-length human WBP1 or p53UBC polypeptide sequence, respectively. Such polypeptides may be produced in prokaryotic or eukaryotic host cells by expression of polynucleotides encoding WBP1 or p53UBC, or fragments and analogs thereof. Alternatively, such polypeptides may be synthesized by chemical methods or produced by in vitro translation systems using a polynucleotide template to direct translation. Methods for expression of heterologous proteins in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N.Y. and Berger and Kimmel, *Methods in Enzymology*, Volume 152, *Guide to Molecular Cloning Techniques* (1987), Academic Press, Inc., San Diego, Calif.

Fragments or analogs of WBP1 or p53UBC may be prepared by those of skill in the art. Preferred amino- and carboxy-termini of fragments or analogs of WBP1 or p53UBC occur near boundaries of functional domains. For example, but not for limitation, such functional domains include: (1) domains conferring the property of binding to p53, or (2) domains conferring the property of inducing a dominant p53 mutant phenotype when expressed at sufficient levels in cells expressing wild-type p53. Additionally, such functional domains might include: (1) domains conferring the property of binding to RNA polymerase species, (2) domains having the capacity to directly alter local chromatin structure, which may comprise catalytic activities (e.g., topoisomerases, endonucleases) and/or which may comprise structural features (e.g., zinc fingers, histone-binding moieties), and (3) domains which may interact with accessory proteins and/or transcription factors.

One method by which structural and functional domains may be identified is by comparison of the nucleotide and/or amino acid sequence data shown in FIGS. 1A–1D and 2 to public or proprietary sequence databases. Preferably, computerized comparison methods are used to identify sequence motifs or predicted protein conformation domains that occur in other proteins of known structure and/or function, such as the zinc fingers. For example, the NAD-binding domains of dehydrogenases, particularly lactate dehydrogenase and malate dehydrogenase, are similar in conformation and have amino acid sequences that are detectably homologous (*Proteins, Structures and Molecular Principles*, (1984) Creighton (ed.), W. H. Freeman and Company, New York, which is incorporated herein by reference). Further, a method to identify protein sequences that fold into a known three-dimensional structure are known (Bowie et al. (1991) *Science* 253: 164). Thus, the foregoing examples demonstrate that those of skill in the art can recognize sequence motifs and structural conformations that may be used to define structural and functional domains in the WBP1 and p53UBC sequences of the invention.

Additionally, computerized comparison of sequences shown in FIGS. 1A–1D and 2 to existing sequence databases can identify sequence motifs and structural conformations found in other proteins or coding sequences that indicate similar domains of the WBP1 and p53UBC proteins. For example but not for limitation, the programs GAP, BESTFIT, FASTA, and TFASTA in the Wisconsin Genetics Software Package (Genetics Computer Group, 575 Science Dr., Madison, Wisc.) can be used to identify sequences in databases, such as GenBank/EMBL, that have regions of homology with a WBP1 or p53UBC sequences. Such homologous regions are candidate structural or functional domains. Alternatively, other algorithms are provided for identifying such domains from sequence data. Further, neural network methods, whether implemented in hardware or software, may be used to: (1) identify related protein sequences and nucleotide sequences, and (2) define structural or functional domains in WBP1 or p53UBC polypeptides (Brunak et al. (1991) *J. Mol. Biol.* 220: 49, which is incorporated herein by reference).

Fragments or analogs comprising substantially one or more functional domain may be fused to heterologous polypeptide sequences, wherein the resultant fusion protein exhibits the functional property(ies) conferred by the WBP1 or p53UBC fragment. Alternatively, WBP1 or p53UBC polypeptides wherein one or more functional domain have been deleted will exhibit a loss of the property normally conferred by the missing fragment.

Although one class of preferred embodiments are fragments having amino- and/or carboxy-termini corresponding to amino acid positions near functional domains borders, alternative WBP1 or p53UBC fragments may be prepared. The choice of the amino- and carboxy-termini of such fragments rests with the discretion of the practitioner and will be made based on experimental considerations such as ease of construction, stability to proteolysis, thermal stability, immunological reactivity, amino- or carboxyl-terminal residue modification, or other considerations.

In addition to fragments, analogs of WBP1 or p53UBC can be made. Such analogs may include one or more deletions or additions of amino acid sequence, either at the amino- or carboxy-termini, or internally, or both; analogs may further include sequence transpositions. Analogs may also comprise amino acid substitutions, preferably conservative substitutions. Additionally, analogs may include heterologous sequences generally linked at the amino- or carboxy-terminus, wherein the heterologous sequence(s) confer a functional property to the resultant analog which is not indigenous to the native WBP1 or p53UBC protein. However, WBP1 or p53UBC analogs must comprise a segment of 25 amino acids that has substantial similarity to a portion of the amino acid sequence shown in FIGS. 1A–1D or 2, respectively, and which has at least one of the requisite functional properties enumerated (supra). Preferred amino acid substitutions are those which: (1) reduce susceptibility to proteolysis, (2) reduce susceptibility to oxidation, (3) alter post-translational modification of the analog, possibly including phosphorylation, and (4) confer or modify other physicochemical or functional properties of such analogs, possibly including interaction with p53 or phosphorylation or dephosphorylation thereof. WBP1 or p53UBC analogs include various muteins of a WBP1 or p53UBC sequence other than the naturally-occurring peptide sequence. For example, single or multiple amino acid substitutions (preferably conservative amino acid substitutions) may be made in the naturally-occurring WBP1 or p53UBC sequence (preferably in the portion of the polypeptide outside the functional domains).

Conservative amino acid substitution is a substitution of an amino acid by a replacement amino acid which has similar characteristics (e.g., those with acidic properties: Asp and Glu). A conservative (or synonymous) amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles*, (1984) Creighton (ed.), W. H. Freeman and Company, New York; *Introduction to Protein Structure*, (1991), C. Branden and J. Tooze, Garland Publishing, New York, N.Y.; and Thornton et al. (1991) *Nature* 354: 105; which are incorporated herein by reference).

Native WBP1 or p53UBC proteins, fragments thereof, or analogs thereof can be used as reagents in p53 binding assays for identifying agents that interfere with p53 function, said agents are thereby identified as p53-modulatory agents, which are candidate drugs. Typically, in vitro p53 binding assays that measure binding of WBP1 or p53UBC polypeptides to p53. WBP1 or p53UBC polypeptides are typically contacted with p53 polypeptide(s) under aqueous conditions that permit specific binding in control binding reactions with a binding affinity of about $1 \times 10^6$ M$^{-1}$ or greater (e.g., 10–250 mM NaCl or KCl and 5–100 mM Tris HCl pH 5–9, usually pH 6–8), generally may including $Zn^{+2}$ and/or $Mn^{+2}$ and/or $Mg^{+2}$ in the nanomolar to micromolar range (1 nM to 999 µM). Specificity of binding is typically established by adding unlabeled competitor at various concentrations selected at the discretion of the practitioner. Examples of unlabeled protein competitors include, but are not limited to, the following: unlabeled WBP1 or ps3UBC polypeptide, bovine serum albumin, dry milk fractions, and nuclear protein extracts. Binding reactions wherein one or more agents are added are performed in parallel with a control binding reaction that does not include an agent. Agents which inhibit the specific binding of WBP1 or p53UBC polypeptides to p53, as compared to a control reaction, are identified as candidate p53-modulatory drugs.

WBP1 and p53UBC polypeptides have many utilities, including but not limited to their use as oncotic pressure-enhancing solutes (typically WBP1 and p53UBC polypeptides of 15–10,000 amino acids or more are dissolved in an aqueous solvent, such as PBS, to produce a solution having substantial oncotic pressure or as a non-specific blocking agent to replace albumin or milk whey proteins in immunoassay formats such as a Western blot preblock solution), their use as nutritive foodstuffs, their use as a combustible energy source, and other uses described herein or apparent to the practitioner.

Pentidomimetics of p53-Interacting Polypeptides

In addition to p53-interacting polypeptides consisting only of naturally-occuring amino acids, WBPL or p53UBC peptidomimetics are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) *Adv. Drug Res.* 15: 29; Veber and Freidinger (1985) *TINS* p.392; and Evans et al. (1987) *J. Med. Chem* 30: 1229, which are incorporated herein by reference) and are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biological or pharmacological activity), such as human WBP1 or p53UBC, but have one or more peptide linkages optionally replaced by a linkage selected from the group consisting of: —CH$_2$NH—, —CH$_2$S—, —CH$_2$—CH$_2$—, —CH=CH— (cis and trans), —COCH$_2$—, —CH(OH)CH$_2$—, and —CH$_2$SO—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., *Trends Pharm Sci* (1980) pp. 463–468

(general review); Hudson, D. et al., *Int J Pept Prot Res* (1979) 14:177–185 (—CH$_2$NH—, CH$_2$CH$_2$—); Spatola, A. F. et al., *Life Sci* (1986) 38:1243–1249 (—CH$_2$—S); Hann, M. M., *J Chem Soc Perkin Trans I* (1982) 307–314 (—CH—CH—, cis and trans); Almquist, R. G. et al., *J Med Chem* (1980) 23:1392–1398 (—COCH$_2$—); Jennings-White, C. et al., *Tetrahedron Lett* (1982) 23:2533 (—COCH$_2$—); Szelke, M. et al., European Appln. EP 45665 (1982) CA: 97:39405 (1982) (—CH(OH)CH$_2$—); Holladay, M. W. et al., *Tetrahedron Lett* (1983) 24:4401–4404 (—C(OH)CH$_2$—); and Hruby, V. J., *Life Sci* (1982) 31:189–199 (—CH$_2$—S—); each of which is incorporated herein by reference. A particularly preferred non-peptide linkage is —CH$_2$NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) (e.g., p53) to which the peptidomimetic binds to produce the therapeutic effect. Derivitization (e.g., labelling) of peptidomimetics should not substantially interfere with the desired biological or pharmacological activity of the peptidomimetic. Peptidomimetics of WBP1 or p53UBC may be used as competitive or noncompetitive agonists or antagonists of WBP1 or p53UBC function, respectively. For example, a WBP1 peptidomimetic administered to a cell containing WBP1 protein and may compete with the naturally-occurring WBP1 protein and reduce WBP1 activity. Alternatively, an WBP1 peptidomimetic administered to a cell lacking WBP1 may provide WBP1 function (e.g., modulation of p53 activity) or the like.

Systematic substitution of one or more amino acids of a consensus sequence with a D-amino acid of the same type (e.g., D-lysine in place of L-lysine) may be used to generate more stable peptides. In addition, constrained peptides (including cyclized peptides) comprising a consensus sequence or a substantially identical consensus sequence variation may be generated by methods known in the art (Rizo and Gierasch (1992) *Ann. Rev. Biochem.* 61: 387, incorporated herein by reference); for example, by adding internal cysteine residues capable of forming intramolecular disulfide bridges which cyclize the peptide.

The amino acid sequences of WBP1 or p53UBC polypeptides identified herein will enable those of skill in the art to produce polypeptides corresponding to WBP1 or p53UBC peptide sequences and sequence variants thereof. Such polypeptides may be produced in prokaryotic or eukaryotic host cells by expression of polynucleotides encoding a WBP1 or p53UBC peptide sequence, frequently as part of a larger polypeptide. Alternatively, such peptides may be synthesized by chemical methods. Methods for expression of heterologous proteins in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N.Y.; Berger and Kimmel, *Methods in Enzymology, Volume 152, Guide to Molecular Cloning Techniques* (1987), Academic Press, Inc., San Diego, Calif.; Merrifield, J. (1969) *J. Am. Chem. Soc.* 91: 501; Chaiken I. M. (1981) *CRC Crit. Rev. Biochem.* 11: 255; Kaiser et al.(1989) *Science* 243: 187; Merrifield, B. (1986) *Science* 232: 342; Kent, S.B.H. (1988) *Ann. Rev. Biochem.* 57: 957; and Offord, R. E. (1980) *Semisynthetic Proteins*, Wiley Publishing, which are incorporated herein by reference).

Production and Applications of α-WBP1 or α-p53UBC Antibodies

Native p53-interacting polypeptides, fragments thereof, or analogs thereof, may be used to immunize an animal for the production of specific antibodies. These antibodies may comprise a polyclonal antiserum or may comprise a monoclonal antibody produced by hybridoma cells. For general methods to prepare antibodies, see *Antibodies: A Laboratory Manual*, (1988) E. Harlow and D. Lane, Cold Spring Harbor Laboratory, Cold Spring Harbor, N.Y., which is incorporated herein by reference.

For example but not for limitation, a recombinantly produced fragment of human WBP1 or p53UBC can be injected into a rat along with an adjuvant following immunization protocols known to those of skill in the art so as to generate an immune response. Typically, approximately at least 1–50 µg of a WBP1 or p53UBC fragment or analog is used for the initial immunization, depending upon the length of the polypeptide. Alternatively or in combination with a recombinantly produced WBP1 or p53UBC polypeptide, a chemically synthesized peptide having a WBP1 or p53UBC sequence (e.g., peptides exemplified in Tables III and IV, infra) may be used as an immunogen to raise antibodies which bind a WBP1 or p53UBC protein, respectively, such as a native human WBP1 or p53UBC polypeptide having the sequence shown essentially in FIGS. 1A–1D or FIG. 2. Immunoglobulins which bind the recombinant fragment with a binding affinity of at least 1×10$^7$ M$^{-1}$ can be harvested from the immunized animal as an antiserum, and may be further purified by immunoaffinity chromatography or other means. Additionally, spleen cells are harvested from the immunized animal (typically rat or mouse) and fused to myeloma cells to produce a bank of antibody-secreting hybridoma cells. The bank of hybridomas can be screened for clones that secrete immunoglobulins which bind the recombinantly produced WBP1 or p53UBC polypeptide (or chemically synthesized WBP1 or p53UBC polypeptide) with an affinity of at least 1×10$^6$ M–1. Animals other than mice and rats may be used to raise antibodies; for example, goats, rabbits, sheep, and chickens may also be employed to raise antibodies reactive with a WBP1 or p53UBC protein. Transgenic mice having the capacity to produce substantially human antibodies also may be immunized and used for a source of a-WBP1 or a-p53UBC antiserum and/or for making monoclonal-secreting hybridomas.

Bacteriophage antibody display libraries may also be screened for binding to a WBP1 or p53UBC polypeptide, such as a full-length human protein, a fragment (e.g., a peptide having a sequence shown in Table III or IV, infra), or a fusion protein comprising a WBP1 or p53UBC polypeptide sequence of at least 14 contiguous amino acids as shown in FIGS. 1A–1D or FIG. 2 or a polypeptide sequence of Table III or IV (infra). Combinatorial libraries of antibodies have been generated in bacteriophage lambda expression systems which may be screened as bacteriophage plaques or as colonies of lysogens (Huse et al. (1989) *Science* 246: 1275; Caton and Koprowski (1990) *Proc. Natl. Acad. Sci. (U.S.A.)* 87: 6450; Mullinax et al (1990) *Proc. Natl. Acad. Sci. (U.S.A.)* 87: 8095; Persson et al. (1991) *Proc. Natl. Acad. Sci. (U.S.A.)* 88: 2432). Various embodiments of bacteriophage antibody display libraries and lambda phage expression libraries have been described (Kang et al. (1991) *Proc. Natl. Acad. Sci. (U.S.A.)* 88: 4363; Clackson et al. (1991) *Nature* 352: 624; McCafferty et al. (1990) *Nature* 348: 552; Burton et al. (1991) *Proc. Natl. Acad. Sci. (U.S.A.)*

88: 10134; Hoogenboom et al. (1991) *Nucleic Acids Res.* 19: 4133; Chang et al. (1991) *J. Immunol.* 147: 3610; Breitling et al. (1991) *Gene* 104: 147; Marks et al. (1991) *J. Mol. Biol.* 222: 581; Barbas et al. (1992) *Proc. Natl. Acad. Sci. (U.S.A.)* 89: 4457; Hawkins and Winter (1992) *J. Immunol.* 22: 867; Marks et al. (1992) *Biotechnology* 10: 779; Marks et al. (1992) *J. Biol. Chem.* 267: 16007; Lowman et al (1991) *Biochemistry* 30: 10832; Lerner et al. (1992) *Science* 258: 1313, incorporated herein by reference). Typically, a bacteriophage antibody display library is screened with a WBP1 or p53UBC polypeptide that is immobilized (e.g., by covalent linkage to a chromatography resin to enrich for reactive phage by affinity chromatography) and/or labeled (e.g., to screen plaque or colony lifts).

WBP1 or p53UBC polypeptides which are useful as immunogens, for diagnostic detection of α-WBP1 or α-p53UBC antibodies in a sample, for diagnostic detection and quantitation of WBP1 or p53UBC protein in a sample (e.g., by standardized competitive ELISA), or for screening a bacteriophage antibody display library, are suitably obtained in substantially pure form, that is, typically about 50 percent (w/w) or more purity, substantially free of interfering proteins and contaminants. Preferably, these polypeptides are isolated or synthesized in a purity of at least 80 percent (w/w) and, more preferably, in at least about 95 percent (w/w) purity, being substantially free of other proteins of humans, mice, or other contaminants. Preferred immunogens comprise at least one WBP1 or p53UBC polypeptide sequence shown in Table III or IV, either as a discrete peptide or as part of a fusion polypeptide (e.g., with a β-galactosidase or glutathione S-transferase sequence). WBP1 or p53UBC immunogens comprise at least one, typically several of such immunogenic epitopes.

For some applications of these antibodies, such as identifying immunocrossreactive proteins, the desired antiserum or monoclonal antibody(ies) is/are not monospecific. In these instances, it may be preferable to use a synthetic or recombinant fragment of WBP1 or p53UBC as an antigen rather than using the entire native protein. More specifically, where the object is to identify immunocrossreactive polypeptides that comprise a particular structural moiety, such as a p53-binding domain, it is preferable to use as an antigen a fragment corresponding to part or all of a commensurate structural domain in the p53-interacting polypeptide. Production of recombinant or synthetic fragments having such defined amino- and carboxy-termini is provided by the WBP1 and p53UBC sequences shown in FIGS. 1A–1D and FIG. 2, respectively.

If an antiserum is raised to a WBP1 or p53UBC fusion polypeptide, such as a fusion protein comprising a WBP1 or p53UBC immunogenic epitope fused to β-galactosidase or glutathione S-transferase, the antiserum is preferably preadsorbed with the non-p53-interacting polypeptide fusion partner (e.g, β-galactosidase or glutathione S-transferase) to deplete the antiserum of antibodies that react (i.e., specifically bind to) the non-p53-interacting polypeptide portion of the fusion protein that serves as the immunogen. Monoclonal or polyclonal antibodies which bind to the human and/or murine WBP1 or p53UBC protein can be used to detect the presence of human or murine WBP1 or p53UBC polypeptides in a sample, such as a Western blot of denatured protein (e.g., a nitrocellulose blot of an SDS-PAGE) obtained from a cell sample of a patient. Preferably quantitative detection is performed, such as by densitometric scanning and signal integration of a Western blot. The monoclonal or polyclonal antibodies will bind to the denatured WBP1 or p53UBC epitopes and may be identified visually or by other optical means with a labeled second antibody or labeled *Staphylococcus aureus* protein A by methods known in the art. Frequently, denatured WBP1 or p53UBC will be used as the target antigen so that more epitopes may be available for binding.

TABLE III

| WBP1 Polypeptide Sequences and Epitopes | |
|---|---|
| -HYNTSLLAAAAAAVSDDQDL- | (SEQ ID NO:70) |
| -LHSSRFFPYTSSQMFLDQLSA- | (SEQ ID NO:71) |
| -LPPTKNGVEPKRPSRPINI- | (SEQ ID NO:72) |
| -SLVRLSTTVPNTIVVSWTA- | (SEQ ID NO:73) |
| -KELYRRRFPQKIMTPADLSIPN- | (SEQ ID NO:74) |
| -KLQKLPFYDLLDELIK- | (SEQ ID NO:75) |
| -EKLTADPDSEIATTSLRVS- | (SEQ ID NO:76) |
| -LLCPLGKMRLTIPCRALTCS- | (SEQ ID NO:77) |
| -IGRNYSMAVYLVKQLSSTV- | (SEQ ID NO:78) |
| -LLQRLRAKGIRNPDHSRALI- | (SEQ ID NO:79) |
| -DFTVQVQLRFCLSETSCPQE- | (SEQ ID NO:80) |
| -HFPPNLCVKVNTKPCSLPG- | (SEQ ID NO:81) |
| -TSLASDNSQRFRETCFAF- | (SEQ ID NO:82) |
| -PQQVQQISSSMDISGTKC- | (SEQ ID NO:83) |
| -LQCFDATLYIQMNEKKPTW- | (SEQ ID NO:84) |
| -VCPVGDKKAPYEHLIIDGL- | (SEQ ID NO:85) |
| -EILKYCTDCDEIQFKEDGT- | (SEQ ID NO:86) |
| -WAPMRSKKEVQEVSASYNGV- | (SEQ ID NO:87) |
| -DGCLSSTLEHQVASHHQSSN- | (SEQ ID NO:88) |
| -KNKKVEVIDLTIDSSSDEEEEE- | (SEQ ID NO:89) |
| -EEPSAKRTCPSLSPTSPLNN- | (SEQ ID NO:90) |
| -KGILSLPHQASPVSRTPSLP- | (SEQ ID NO:91) |
| -AVDTSYINTSLIQDYRHPFH- | (SEQ ID NO:92) |
| -TPMPYDLQGLDFFPFLSGD- | (SEQ ID NO:93) |
| -SLVSSNSLRESHSHTVTNR- | (SEQ ID NO:94) |
| -SSTDTASIFGIIPDIISLD- | (SEQ ID NO:95) |
| -HSSPMPATLSPSTIPQLTYDG- | (SEQ ID NO:96) |
| -HPASSPLLPVSLLGPKHELELPH- | (SEQ ID NO:97) |
| -ELPHLTSALHPVHPDIKLQ- | (SEQ ID NO:98) |
| -FAFALTPQQVQQISSSMDISGTKC- | (SEQ ID NO:99) |

Such WBP1 sequences as shown in Table III may be used as an immunogenic peptide directly (e.g., to screen bacteriophage antibody display libraries or to immunize a rabbit), or may be conjugated to a carrier macromolecule (e.g., BSA) or may compose part of a fusion protein to be used as an immunogen. A preferred WBP1 polypeptide comprises the following amino acids sequences:

| -PASSPLLPVSLLGPKHELEH-; | (SEQ ID NO:100) |
|---|---|
| -PQQVQQISSSMDISGTKC-; | (SEQ ID NO:83) |
| -LLQRLRAKGIRNPDHSRALI-; | (SEQ ID NO:79) |
| -WAPMRSKKEVQEVSASYNGV-; | (SEQ ID NO:87) |
| -EEPSAKRTCPSLSPTSPLNN-; | (SEQ ID NO:90) |
| -TPMPYDLQGLDFFPFLSGD-; | (SEQ ID NO:93) |
| -SLVSSNSLRESHSHTVTNR-; | (SEQ ID NO:94) |
| -SSTDTASIFGIIPDIISLD-; | (SEQ ID NO:95) | and may comprise other intervening and/or terminal sequences; generally such polypeptides are less than 1000 amino acids in length, more usually less than about 500 amino acids in length; often spacer peptide sequences or terminal peptide sequences, if present, correspond to naturally occurring polypeptide sequences, generally mammalian polypeptide sequences. Preferably, the order of the amino acid sequences, from amino-terminal to carboxy-terminal direction are:

| (1) -PASSPLLPVSLLGPKHELEH-; | (SEQ ID NO:100) |
|---|---|
| (2) -PQQVQQISSSMDISGTKC-; | (SEQ ID NO:83) |
| (3) -LLQRLRAKGIRNPDHSRALI-; | (SEQ ID NO:79) |
| (4) -WAPMRSKKEVQEVSASYNGV-; | (SEQ ID NO:87) |
| (5) -EEPSAKRTCPSLSPTSPLNN-; | (SEQ ID NO:90) |
| (6) -TPMPYDLQGLDFFPFLSGD-; | (SEQ ID NO:93) |

-continued
(7) -SLVSSNSLRESHSHTVTNR-;  (SEQ ID NO:94)
(8) -SSTDTASIFGIIPDIISLD-.  (SEQ ID NO:95)

One application of the preferred WBP1 polypeptide just recited is as a commercial immunogen to raise α-WBP1 antibodies in a suitable animal and/or as a commercial immunodiagnostic reagent for quantitative ELISA (e.g., competitive ELISA) or competitive RIA in conjunction with the anti-WBP1 antibodies provided by the invention, such as for calibration of standardization of such immunoassays for staging or diagnosis of WBP1-expressing tumors in humans or cell typing or identification of cells. Such immunological detection may be used to detect denatured WBP1 polypeptides (e.g., Western blots of SDS-polyacrylamide gels) wherein a variety of epitopes are exposed in the denatured WBP1 protein or peptide fragments (e.g., following proteolytic digestion). The preferred WBP1 polypeptide just recited will find many other uses in addition to serving as an immunogen or immunological reagent. One or more of the above-listed sequences may be incorporated into a fusion protein with a fusion partner such as human serum albumin, GST, etc. For such fusion proteins in excess of 1000 amino acids, deletions in the fusion partner (albumin) moiety may be made to bring the size to about 1000 amino acids or less, if desired.

In some embodiments, it will be desirable to employ a polyvalent WBP1 antigen, comprising at least two WBP1 immunogenic epitopes in covalent linkage, usually in peptide linkage. Such polyvalent WBP1 antigens typically comprise multiple WBP1 antigenic peptides from the same species (e.g., human or mouse), but may comprise a mix of antigenic peptides from WBP1 proteins of different species (i.e., an interspecies WBP1 polyvalent antigen). Frequently, the spatial order of the antigenic peptide sequences in the primary amino acid sequence of a polyvalent antigen occurs in the same orientation as in the naturally occurring WBP1 protein (i.e., a first antigenic peptide sequence that is amino-terminal to a second antigenic peptide sequence in a naturally occurring WBP1 protein will be amino-terminal to said second antigenic peptide sequence in a polyvalent antigen. Frequently, spacer peptide sequences will be used to link antigenic peptide sequences in a polyvalent antigen, such spacer peptide sequences may be predetermined, random, or pseudorandom sequences. Spacer peptide sequences may correspond to sequences known to be non-immunogenic to the animal which is to be immunized with the polyvalent antigen, such as a sequence to which the animal has been tolerized. Although many examples of such polyvalent antigens may be given, the following embodiment is provided for illustration and not limitation:

-PQQVQQISSSMDISGTKC-(aa1)-EEPSAKRTCPSLSPTSPLNN-
(aa2)-SLVSSNSLRESHSHTVNR-  (SEQ ID NO:101)

where (aa1) and (aa2) are peptide spacers of at least one amino acid and less than 1000 amino acids; aa1 is a peptide sequence selected independently from the aa2 peptide sequence; the length of aa1 (which may be composed of multiple different amino acids) is independent of the length of aa2 (which may be composed of multiple different amino acids).

A preferred type of WBP1 polypeptide immunogen comprises the 597 amino acid long polypeptide sequence (SEQ ID NO:102):

| | | | | | |
|---|---|---|---|---|---|
| 1 | MKIKELYRRR | FPQKIMTPAD | LSIPNVHSSP | MPATLSPSTI | PQLTYDGHPA |
| 51 | SSPLLPVSLL | GPKHELELPH | LTSALHPVHP | DIKLQKLPFY | DLLDELIKPT |
| 101 | SLASDNSQRF | RETCFAFALT | PQQVQQISSS | MDISGTKCDF | TVQVQLRFCL |
| 151 | SETSCPQEDH | FPPNLCVKVN | TKPCSLPGYL | PPTKNGVEPK | RPSRPINITS |
| 201 | LVRLSTTVPN | TIVVSWTAEI | GRNYSMAVYL | VKQLSSTVLL | QRLRAKGIRN |
| 251 | PDHSRALIKE | KLRADPDSEI | ATTSLRVSLL | CPLGKMRLTI | PCRALTCSHL |
| 301 | QCFDATLYIQ | MNEKKPTWVC | PVCDKKAPYE | HLIIDGLFME | ILKYCTDCDE |
| 351 | IQFKEDGTWA | PMRSKKEVQE | VSASYNGVDG | CLSSTLEHQV | ASHHQSSNKN |
| 401 | KKVEVIDLTI | DSSSDEEEEE | PSAKRTCPSL | SPTSPLNNKG | ILSLPHQASP |
| 451 | VSRTPSLPAV | DTSYINTSLI | QDYRHPFHMT | PMPYDLQGLD | FFPFLSGNDQ |
| 501 | HYNTSLLAAA | AAAVSDDQDL | LHSSRFFPYT | SSQMFLDQLS | AGGSTSLPTT |
| 551 | NGSSSGSNSS | LVSSNSLRES | HSHTVTNRSS | TDTASIFGII | PDIISLD 597 |

A preferred species consists of the 597 amino acid sequence shown above, without amino-terminal or carboxy-terminal extensions.

In one variation a WBP1 polypeptide comprises a p53-binding segment comprising the sequence (SEQ. ID NO:103):

-SSTLEHQVASHHQSSNKNKKVEVIDLTIDSSSDEEEEEPSAKRTCPSLSPTSPLNNKG
ILSLPHQASPVSRTPSLPAVDTSYINTSLIQDYRHPFHMTPMP-.
For example and not limitation, such a polypeptide can consist of the sequence (SEQ ID NO:103):
SSLTEHQVASHHQSSNKNKKVEVIDLTIDSSSDEEEEEPSAKRTCP
SLSPTSPLNNKGILSLPHQASPVSRTPSLPAVDTSYINTSLIQDYRHPFHMTPMP.

Polynucleotides encoding epitopes having substantial identity to these preferred epitopes are often employed. Such polynucleotides have a variety of uses, including as WBP1 probes, as templates for producing polypeptides comprising a WBP1 epitope whereby such proteins are WBP1 immunogens or commercial diagnostic reagents for standardizing a WBP1 immunoassay, as polynucleotide vaccines (immunogens) when fused to a secretory sequence for administering to an animal and making α-WBP1 antisera and hybridomas; such polynucleotides can also be used as foodstuffs, combustible energy sources, and viscosity-enhancing solutes.

TABLE IV

| p53UBC Polypeptide Sequence and Epitopes | |
|---|---|
| -GTLNMSGIALSRLAQERKA-; | (SEQ ID NO:104) |
| -DHPFGFVAVPTKNPDGTMNLMNW-; | (SEQ ID NO:105) |
| -TPWEGGLFKLRMLFKDDYPSSPPK-; | (SEQ ID NO:106) |
| -VYFGTVCLSILEEDKDWRPA-; | (SEQ ID NO:107) |
| -QELLNEPNIQDPAQAEAYTIYCQNR-; | (SEQ ID NO:108) |
| -AQAKNLRPHKQRPCGIV-; | (SEQ ID NO:109) |
| -RVCGLDSLNCPFPYRVSSSVFCIFD-; | (SEQ ID NO:110) |
| -LFKLRMLFKDDYPSSPPKCKFEPP- | (SEQ ID NO:111) |

Such p53UBC sequences as shown in Table IV may be used as an immunogenic peptide directly (e.g., to screen bacteriophage antibody display libraries or to immunize a rabbit), or may be conjugated to a carrier macromolecule (e.g., BSA) or may compose part of a fusion protein to be used as an immunogen. A preferred p53UBC polypeptide comprises the following amino acids sequences:

| | |
|---|---|
| -RKAWRKDHPFGFVAVPTKNP-; | (SEQ ID NO:112) |
| -NIQPAQAEAYTIYCQNRVEYE-; | (SEQ ID NO:113) |
| -GLVWQELVYNIFANLKLLHT-; | (SEQ ID NO:114) |
| -GLDSLNCPFPYRVSSSVFCI- | (SEQ ID NO:115) |
| -KLAFILILMSVFQL-; | (SEQ ID NO:116) | and may comprise other intervening and/or terminal sequences; generally such polypeptides are less than 1000 amino acids in length, more usually less than about 500 amino acids in length; often spacer peptide sequences or terminal peptide sequences, if present, correspond to naturally occurring polypeptide sequences, generally mammalian polypeptide sequences. Preferably, the order of the amino acid sequences, from amino-terminal to carboxy-terminal direction are:

| | |
|---|---|
| (1) -RKAWRKDHPFGFVAVPTKNP-; | (SEQ ID NO:112) |
| (2) -NIQPAQAEAYTIYCQNRVEYE-; | (SEQ ID NO:113) | as for calibration of standardization of such immunoassays for staging or diagnosis of p53UBC-expressing tumors in humans or cell typing or identification of cells. Such immunological detection may be used to detect denatured p53UBC polypeptides (e.g., Western blots of SDS-polyacrylamide gels) wherein a variety of epitopes are exposed in the denatured p53UBC protein or peptide fragments (e.g., following proteolytic digestion). The preferred p53UBC polypeptide just recited will find many other uses in addition to serving as an immunogen or immunological reagent. One or more of the above-listed sequences may be incorporated into a fusion protein with a fusion partner such as human serum albumin, GST, etc. For such fusion proteins in excess of 1000 amino acids, deletions in the fusion partner (albumin) moiety may be made to bring the size to about 1000 amino acids or less, if desired.

In some embodiments, it will be desirable to employ a polyvalent p53UBC antigen, comprising at least two p53UBC immunogenic epitopes in covalent linkage, usually in peptide linkage. Such polyvalent p53UBC antigens typically comprise multiple p53UBC antigenic peptides from the same species (e.g., human or mouse), but may comprise a mix of antigenic peptides from p53UBC proteins of different species (i.e., an interspecies p53UBC polyvalent antigen). Frequently, the spatial order of the antigenic peptide sequences in the primary amino acid sequence of a polyvalent antigen occurs in the same orientation as in the naturally occurring p53UBC protein (i.e., a first antigenic peptide sequence that is amino-terminal to a second antigenic peptide sequence in a naturally occurring p53UBC protein will be amino-terminal to said second antigenic peptide sequence in a polyvalent antigen. Frequently, spacer peptide sequences will be used to link antigenic peptide sequences in a polyvalent antigen, such spacer peptide sequences may be predetermined, random, or pseudorandom sequences. Spacer peptide sequences may correspond to sequences known to be non-immunogenic to the animal which is to be immunized with the polyvalent antigen, such as a sequence to which the animal has been tolerized. Although many examples of such polyvalent antigens may be given, the following embodiment is provided for illustration and not limitation:

-TLNMSGIALSRLAQER-(aa1)-GIQELLNEPNIQPAQAEAYTI-(aa2)-AGMLLTVQSCTWPQLAVWKCT- (SEQ ID NO:117)

-continued

| | |
|---|---|
| (3) -GLVWQELVYNIFANLKLLHT-; | (SEQ ID NO:114) |
| (4) -GLDSLNCPFPYRVSSSVFCI- | (SEQ ID NO:115) |
| (5) -KLAFILILMSVFQL-. | (SEQ ID NO:116) |

One application of the preferred p53UBC polypeptide just recited is as a commercial immunogen to raise α-p53UBC antibodies in a suitable animal and/or as a commercial immunodiagnostic reagent for quantitative ELISA (e.g., competitive ELISA) or competitive RIA in conjunction with the anti-p53UBC antibodies provided by the invention, such where (aa1) and (aa2) are peptide spacers of at least one amino acid and less than 1000 amino acids; aal is a peptide sequence selected independently from the aa2 peptide sequence; the length of aa1 (which may be composed of multiple different amino acids) is independent of the length of aa2 (which may be composed of multiple different amino acids).

A preferred species of p53UBC polypeptide immunogen is the 253 amino acid long human p53UBC protein shown below:

| | | | | | | |
|---|---|---|---|---|---|---|
| 1 | RGTLNMSGIA | LSRLAQERKA | WRKDHPFGFV | AVPTKNPDGT | MNLMNWESAI | (SEQ ID NO:118) |
| 51 | PGKKGTPWEG | GLFKLRMLFK | DDYPSSPPKC | KFEPPLFHPN | VYFGTVCLSI | |
| 101 | LEEDKDWRPA | ITIKQILLGI | QELLNEPNIQ | DPAQAEAYTI | YCQNRVEYEK | |
| 151 | RVRAQAKNLR | PHKQRPCGIV | RRKGLVWQEL | VYNIFANLKL | LHTMTSHLGG | |

```
201  LGGRHLPLPP   RVCGLDSLNC   PFPYRVSSSV   FCIFDCYVKL   AFILILMSVF
251  QLL
```

Immunogenic WBP1 or p53UBC peptides may be used to immunize an animal to raise anti-WBP1 and anti-p53UBC antibodies and/or as a source of spleen cells for making a hybridoma library from which to select hybridoma clones which secrete a monoclonal antibody which binds to a WBP1 or p53UBC protein with an affinity of $1\times10^7$ $M^{-1}$ or greater, preferably at least $1\times10^8$ $M^{-1}$ to $1\times10^9$ $M^{-1}$. Such immunogenic WBP1 or p53UBC peptides can also be used to screen bacteriophage antibody display libraries directly.

One use of such antibodies is to screen cDNA expression libraries, preferably containing cDNA derived from human or murine mRNA from various tissues, for identifying clones containing cDNA inserts which encode structurally-related, immunocrossreactive proteins, that are candidate novel p53-interacting polypeptides. Such screening of cDNA expression libraries is well known in the art, and is further described in Young et al. (1983) Proc. Natl. Acad. Sci. (U.S.A.) 80: 1194 as well as other published sources. Another use of such antibodies is to identify and/or purify immunocrossreactive proteins that are structurally or evolutionarily related to the native WBP1 or p53UBC protein or to the corresponding WBP1 or p53UBC fragment (e.g., functional domain; p53-binding domain) used to generate the antibody. It is believed that such antibodies will find commercial use as such reagents for research applications, just as other antibodies (and biological reagents—such as restriction enzymes and polymerases) are sold commercially.

Various other uses of such antibodies are to diagnose and/or stage neoplasms or other cell proliferation disease states, and for therapeutic application (e.g., as cationized antibodies or by targeted liposomal delivery) to treat neoplasia, inflammation, wound healing, graft rejection, and the like. The antibodies can also be used to quantitate WBP1 and/or p53UBC protein in a sample (e.g., via ELISA or Western blot) to provide a standard value(s) for comparison to other polypeptides detected in the same sample (e.g., to verify that lanes of a polyacrylamide gel transferred to a membrane in a Western blot each comprise comparable levels of WBP1 and/or p53UBC and specifically differ in levels of a test polypeptide). Polynucleotides encoding epitopes having substantial identity to these preferred epitopes are often employed. Such polynucleotides have a variety of uses, including as p53UBC probes, as templates for producing polypeptides comprising a p53UBC epitope whereby such proteins are p53UBC immunogens or commercial diagnostic reagents for standardizing a p53UBC immunoassay, as polynucleotide vaccines (immunogens) when fused to a secretory sequence for administering to an animal and making α-p53UBC antisera and hybridomas; such polynucleotides can also be used as foodstuffs, combustible energy sources, and viscosity-enhancing solutes.

WBP1 Polynucleotides

Disclosure of the coding sequence for human WBP1 shown in FIGS. 1A–1D and the sequence of the 597 amino acid long WBP1 polypeptide (supra) makes possible the construction of isolated polynucleotides that can direct the expression of WBP1, fragments thereof, or analogs thereof. Such polypeptides can comprise any degenerate nucleotide sequence encoding a WBP1 polypeptide sequence of FIGS. 1A–1D. Further, the sequences in FIGS. 1A–1D make possible the construction of nucleic acid hybridization probes and PCR primers that can be used to detect RNA and DNA sequences encoding WBP1.

Polynucleotides encoding full-length WBP1 or fragments or analogs thereof, may include sequences that facilitate transcription (expression sequences) and translation of the coding sequences, such that the encoded polypeptide product is produced. Construction of such polynucleotides is well known in the art and is described further in Maniatis et al., Molecular Cloning: A Laboratory Manual, 2nd Ed. (1989), Cold Spring Harbor, N.Y. For example, but not for limitation, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector. A typical eukaryotic expression cassette will include a polynucleotide sequence encoding a WBP1 polypeptide linked downstream (i.e., in translational reading frame orientation; polynucleotide linkage) of a promoter such as the HSV tk promoter or the pgk (phosphoglycerate kinase) promoter, optionally linked to an enhancer and a downstream polyadenylation site (e.g., an SV40 large T Ag poly A addition site).

A preferred WBP1 polynucleotide encodes a WBP1 polypeptide that comprises at least one of the amino acids sequences shown in Table III. The degeneracy of the genetic code gives a finite set of polynucleotide sequences encoding these amino acid sequences; this set of degenerate sequences may be readily generated by hand or by computer using commercially available software (Wisconsin Genetics Software Package Release 7.0). Thus, isolated polynucleotides typically less than approximately 10,000 nucleotides in length and comprising sequences encoding each of the following amino acid sequences:

| | |
|---|---|
| -ELPHLTSALHPVHPD-; | (SEQ ID NO:119) |
| -PQQVQQISSSMDISGTKC-; | (SEQ ID NO:83) |
| -LLQRLRAKGIRNPDHSRALI-; | (SEQ ID NO:79) |
| -WAPMRSKKEVQEVSASYNGV-; | (SEQ ID NO:87) |
| -EEPSAKRTCPSLSPTSPLNN-; | (SEQ ID NO:90) |
| -TPMPYDLQGLDFFPFLSGD-; | (SEQ ID NO:93) |
| -SLVSSNSLRESHSHTVTNR-; | (SEQ ID NO:94) |
| -SSTDTASIFGIIPDIISLD-; | (SEQ ID NO:95) | are provided and may be used for, among other uses, the expression of a WBP1 polypeptide which can be used as an immunogen, immunological reagent, and the like. Such polynucleotides typically comprise an operably linked promoter for driving expression in a suitable prokaryotic or eukaryotic host cell. One exemplification of such a polynucleotide is the human WBP1 cDNA sequence of FIGS. 1A–1D cloned in operable linkage to the mammalian expression vector pSRα, many alternative embodiments will be apparent to those of skill in the art, including the use of alternative expression vectors (e.g., pBC12BI and p91023 (B); Hanahan J (1983) J. Mol. Biol. 166: 577; Cullen et al. (1985) J. Virol. 53: 515; Lomedico PT (1982) Proc. Natl. Acad. Sci. (U.S.A.) 79: 5798; Morinaga et al. (1984) BiolTechnology 2: 636).

Additionally, where expression of a polypeptide is not desired, polynucleotides of this invention need not encode a functional protein. Polynucleotides of this invention may serve as hybridization probes and/or PCR primers (amplimers) and/or LCR oligomers for detecting WBP1 RNA or DNA sequences.

Alternatively, polynucleotides of this invention may serve as hybridization probes or primers for detecting RNA or DNA sequences of related genes, such genes may encode structurally or evolutionarily related proteins. For such hybridization and PCR applications, the polynucleotides of the invention need not encode a functional polypeptide. Thus, polynucleotides of the invention may contain substantial deletions, additions, nucleotide substitutions and/or transpositions, so long as specific hybridization or specific amplification to the WBP1 sequence is retained.

Specific hybridization is defined hereinbefore, and can be roughly summarized as the formation of hybrids between a polynucleotide of the invention (which may include substitutions, deletions, and/or additions) and a specific target polynucleotide such as human WBP1 mRNA so that a single band is identified corresponding to each WBP1 isoform on a Northern blot of RNA prepared from WBP1-expressing cells (i.e., hybridization and washing conditions can be established that permit detection of discrete WBP1 mRNA band(s)). Thus, those of ordinary skill in the art can prepare polynucleotides of the invention, which may include substantial additions, deletions, substitutions, or transpositions of nucleotide sequence as compared to sequences shown in FIGS. 1A–1D and determine whether specific hybridization is a property of the polynucleotide by performing a Northern blot using RNA prepared from a cell line which expresses WBP1 mRNA and/or by hybridization to a WBP1 DNA clone (cDNA or genomic clone).

Specific amplification is defined as the ability of a set of PCR amplimers, when used together in a PCR reaction with a WBP1 polynucleotide, to produce substantially a single major amplification product which corresponds to a WBP1 gene sequence or mRNA sequence. Generally, human genomic DNA or mRNA from WBP1 expressing human cells is used as the template DNA sample for the PCR reaction. PCR amplimers that exhibit specific amplification are suitable for quantitative determination of WBP1 mRNA by quantitative PCR amplification. WBP1 allele-specific amplification products, although having sequence and/or length polymorphisms, are considered to constitute a single amplification product for purposes of this definition.

Generally, hybridization probes comprise approximately at least 25 consecutive nucleotides of a sequence shown in FIGS. 1A–1D (for human WBP1 detection, respectively), preferably the hybridization probes contain at least 50 consecutive nucleotides of a sequence shown in FIGS. 1A–1D, and more preferably comprise at least 100 consecutive nucleotides of a sequence shown in FIGS. 1A–1D. PCR amplimers typically comprise approximately 25 to 50 consecutive nucleotides of a sequence shown in FIGS. 1A–1D, and usually consist essentially of approximately 25 to 50 consecutive nucleotides of a sequence shown in FIGS. 1A–1D with additional nucleotides, if present, generally being at the 5' end so as not to interfere with polymerase-mediated chain extension. PCR amplimer design and hybridization probe selection are well within the scope of discretion of practioners of ordinary skill in the art.

p53UBC Polynucleotides

Disclosure of the coding sequence for human p53UBC shown in FIG. 2 and the sequence of the 253 amino acid long p53UBC polypeptide (supra) makes possible the construction of isolated polynucleotides that can direct the expression of p53UBC, fragments thereof, or analogs thereof. Further, the sequences in FIGS. 1A–1D make possible the construction of nucleic acid hybridization probes and PCR primers that can be used to detect RNA and DNA sequences encoding p53UBC.

Polynucleotides encoding full-length p53UBC or fragments or analogs thereof, may include sequences that facilitate transcription (expression sequences) and translation of the coding sequences, such that the encoded polypeptide product is produced. Construction of such polynucleotides is well known in the art and is described further in Maniatis et al., *Molecular Cloning: A Laboratory Manual*, 2nd Ed. (1989), Cold Spring Harbor, N.Y. For example, but not for limitation, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector. A typical eukaryotic expression cassette will include a polynucleotide sequence encoding a p53UBC polypeptide linked downstream (i.e., in translational reading frame orientation; polynucleotide linkage) of a promoter such as the HSV tk promoter or the pgk (phosphoglycerate kinase) promoter, optionally linked to an enhancer and a downstream polyadenylation site (e.g., an SV40 large T Ag poly A addition site).

A preferred p53UBC polynucleotide encodes a p53UBC polypeptide that comprises at least one of the amino acids sequences shown in Table IV. The degeneracy of the genetic code gives a finite set of polynucleotide sequences encoding these amino acid sequences; this set of degenerate sequences may be readily generated by hand or by computer using commercially available software (Wisconsin Genetics Software Package Release 7.0). Thus, isolated polynucleotides typically less than approximately 10,000 nucleotides in length and comprising sequences encoding each of the following amino acid sequences:

| | |
|---|---|
| – RKAWRKDHPFGFVAVPTKNP –; | (SEQ ID NO:112) |
| – NIQDPAQAEAYTTYCQNRVEYE –; | (SEQ ID NO:113) |
| – GLVWQELVYNIFANLKLLHY –; | (SEQ ID NO:114) |
| – GLDSLNCPFPYRVSSSVFCI –; | (SEQ ID NO:115) |
| – KLAFILILMSVFQL –; | (SEQ ID NO:116) | are provided and may be used for, among other uses, the expression of a p53UBC polypeptide which can be used as an immunogen, immunological reagent, and the like. Such polynucleotides typically comprise an operably linked promoter for driving expression in a suitable prokaryotic or eukaryotic host cell. One exemplification of such a polynucleotide is the human p53UBC cDNA sequence of FIG. 2 cloned in operable linkage to the mammalian expression vector pSRα, many alternative embodiments will be apparent to those of skill in the art, including the use of alternative expression vectors (e.g., pBC12BI and p91023(B); Hanahan J (1983) *J. Mol. Biol.* 166: 577; Cullen et al. (1985) *J. Virol.* 53: 515; Lomedico PT (1982) *Proc. Natl. Acad. Sci. (U.S.A.)* 79: 5798; Morinaga et al. (1984) *Bio/Technology* 2: 636).

Additionally, where expression of a polypeptide is not desired, polynucleotides of this invention need not encode a functional protein. Polynucleotides of this invention may serve as hybridization probes and/or PCR primers (amplimers) and/or LCR oligomers for detecting p53UBC RNA or DNA sequences.

Alternatively, polynucleotides of this invention may serve as hybridization probes or primers for detecting RNA or DNA sequences of related genes, such genes may encode structurally or evolutionarily related proteins. For such hybridization and PCR applications, the polynucleotides of the invention need not encode a functional polypeptide. Thus, polynucleotides of the invention may contain substantial deletions, additions, nucleotide substitutions and/or transpositions, so long as specific hybridization or specific amplification to the p53UBC sequence is retained.

Specific hybridization is defined hereinbefore, and can be roughly summarized as the formation of hybrids between a polynucleotide of the invention (which may include substitutions, deletions, and/or additions) and a specific target polynucleotide such as human p53UBC MRNA so that a single band is identified corresponding to each p53UBC isoform on a Northern blot of RNA prepared from p53UBC-expressing cells (i.e., hybridization and washing conditions can be established that permit detection of discrete p53UBC mRNA band(s)). Thus, those of ordinary skill in the art can prepare polynucleotides of the invention, which may include substantial additions, deletions, substitutions, or transpositions of nucleotide sequence as compared to sequences shown in FIGS. 1A–1D and determine whether specific hybridization is a property of the polynucleotide by performing a Northern blot using RNA prepared from a cell line which expresses p53UBC mRNA and/or by hybridization to a p53UBC DNA clone (cDNA or genomic clone).

Specific amplification is defined as the ability of a set of PCR amplimers, when used together in a PCR reaction with a p53UBC polynucleotide, to produce substantially a single major amplification product which corresponds to a p53UBC gene sequence or mRNA sequence. Generally, human genomic DNA or mRNA from p53UBC expressing human cells is used as the template DNA sample for the PCR reaction. PCR amplimers that exhibit specific amplification are suitable for quantitative determination of p53UBC mRNA by quantitative PCR amplification. p53UBC allele-specific amplification products, although having sequence and/or length polymorphisms, are considered to constitute a single amplification product for purposes of this definition.

Generally, hybridization probes comprise approximately at least 25 consecutive nucleotides of a sequence shown in FIG. 2 (for human p53-interacting polypeptide detection, respectively), preferably the hybridization probes contain at least 50 consecutive nucleotides of a sequence shown in FIG. 2, and more preferably comprise at least 100 consecutive nucleotides of a sequence shown in FIG. 2. PCR amplimers typically comprise approximately 25 to 50 consecutive nucleotides of a sequence shown in FIG. 2, and usually consist essentially of approximately 25 to 50 consecutive nucleotides of a sequence shown in FIG. 2 with additional nucleotides, if present, generally being at the 5' end so as not to interfere with polymerase-mediated chain extension. PCR amplimer design and hybridization probe selection are well within the scope of discretion of practioners of ordinary skill in the art.

WBP1 and p53UBC polynucleotides have many utilities, including but not limited to their use as viscosity-enhancing solutes (typically WBP1 and p53UBC polynucleotides of 25–100,000 nucleotides or more are dissolved in an aqueous solvent, such as PBS, to produce a solution having substantial viscosity or as carrier polynucleotides to co-precipitate other polynucleotide species present in solution at low abundance), their use as nutritive foodstuffs, their use as a combustible energy source, and other uses described herein or apparent to the practitioner.

Methods Relating to Genetic Disease

In one preferred embodiment of the invention, hybridization probes that specifically identify the WBP1 or p53UBC gene may be used in methods for diagnosing genetic disease. For example, but not for limitation, the genetic disease thus diagnosed may involve a lesion in the relevant WBP1 or p53UBC structural or regulatory sequences, or may involve a lesion in a genetic locus closely linked to the WBP1 or p53UBC locus and which can be identified by restriction fragment length polymorphism or DNA sequence polymorphism at the linked WBP1 or p53UBC locus. In a further preferred embodiment, WBP1 or pS3UBC gene probes are used to diagnose or identify genetic disease involving predisposition to immunological disease, wherein the amount or functionality of endogenous WBP1 or p53UBC is sufficient for the individual to exhibit an increased probability of developing a disease, particularly a disease of cell proliferation (e.g., neoplasia, senescence, wound healing), arthritis, or autoimmune disease.

Antisense Polynucleotides

Additional embodiments directed to modulation of p53 functional activity include methods that employ specific antisense polynucleotides complementary to all or part of the sequences shown in FIGS. 1A–1D or FIG. 2. Such complementary antisense polynucleotides may include nucleotide substitutions, additions, deletions, or transpositions, so long as specific hybridization to the relevant target sequence corresponding to FIGS. 1A–1D or FIG. 2 is retained as a functional property of the polynucleotide. Complementary antisense polynucleotides include soluble antisense RNA or DNA oligonucleotides which can hybridize specifically to WBP1 or p53UBC mRNA species and prevent transcription of the mRNA species and/or translation of the encoded polypeptide (Ching et al. (1989) *Proc. Natl. Acad. Sci. U.S.A.* 86: 10006; Broder et al. (1990) *Ann. Int. Med.* 113: 604; Loreau et al. (1990) *FEBS Letters* 274: 53; Holcenberg et al., W091/11535; U.S. Ser. No. 07/530,165; W091/09865; W091/04753; W090/13641; and EP 386563, each of which is incorporated herein by reference). The antisense polynucleotides therefore inhibit production of WBP1 or p53UBC polypeptides. Since WBP1 or p53UBC protein expression is associated with p53 binding and function, antisense polynucleotides that prevent transcription and/or translation of MRNA corresponding to WBP1 or p53UBC polypeptides may modulate p53 function and/or reverse the p53 phenotype of cells. Compositions containing a therapeutically effective dosage of WBP1 or p53UBC antisense polynucleotides may be administered for treatment of diseases, including neoplasia, hyperplasia, wound healing, inflammation, and for inhibition of transplant rejection reactions, and the like, if desired. Antisense polynucleotides of various lengths may be produced, although such antisense polynucleotides typically comprise a sequence of about at least 25 consecutive nucleotides which are substantially identical to a naturally-occurring WBP1 or p53UBC polynucleotide sequence, and typically which are identical to a sequence shown in FIGS. 1A–1D or FIG. 2.

Antisense polynucleotides may be produced from a heterologous expression cassette in a transfectant cell or transgenic cell, such as a transgenic pluripotent hematopoietic stem cell used to reconstitute all or part of the hematopoietic stem cell population of an individual. Alternatively, the antisense polynucleotides may comprise soluble oligonucleotides that are administered to the external milieu, either in the culture medium in vitro or in the circulatory system or interstitial fluid in vivo. Soluble antisense polynucleotides present in the external milieu have been shown to gain access to the cytoplasm and inhibit translation of specific mRNA species. In some embodiments the antisense polynucleotides comprise methylphosphonate moieties. For general methods relating to antisense polynucleotides, see *Antisense RNA and DNA*, (1988), D. A. Melton, Ed., Cold Spring Harbor Laboratory, Cold Spring Harbor, N.Y.). The antisense polynucleotides may comprise phosphordithiolate DNA (Marshall WS and Caruthers MH (1993) *Science* 259: 1564), peptide nucleic acids (Egholm et al. (1992) *J. Am. Chem. Soc.* 114: 1895; Hanvey et al. (1992) *Science* 258: 1481), and other polynucleotide-mimetic chemical architectures known or apparent to those of skill in the art.

Isolation of the Cognate Human WBP1 and p53UBC Genes

The human homolog of the WBP1 and p53UBC cDNA sequences are identified and isolated by screening a human genomic clone library, such as a human genomic library in yeast artificial chromosomes, cosmids, or bacteriophage λ (e.g., λ Charon 35), with a polynucleotide probe comprising a sequence of about at least 24 contiguous nucleotides (or their complement) of the cDNA sequence shown in FIGS. 1A–1D or FIG. 2, respectively. Typically, hybridization and washing conditions are performed at high stringency according to conventional hybridization procedures. Positive clones are isolated and sequenced. For illustration and not for limitation, a full-length polynucleotide corresponding to the sequence of FIGS. 1A–1D or FIG. 2 may be labeled and used as a hybridization probe to isolate genomic clones from a human or murine genomic clone library in λEMBL4 or λGEM11 (Promega Corporation, Madison, Wisc.); typical hybridization conditions for screening plaque lifts (Benton and Davis (1978) *Science* 196: 180) can be: 50% formamide, 5×SSC or SSPE, 1–5×Denhardt's solution, 0.1–1% SDS, 100–200 µg sheared heterologous DNA or tRNA, 0–10% dextran sulfate, $1\times10^5$ to $1\times10^7$ cpm/ml of denatured probe with a specific activity of about $1\times10^8$ cpm/µg, and incubation at 42° C. for about 6–36 hours. Prehybridization conditions are essentially identical except that probe is not included and incubation time is typically reduced. Washing conditions are typically 1–3×SSC, 0.1–1% SDS, 50°–70° C. with change of wash solution at about 5–30 minutes.

Nonhuman WBP1 or p53UBC cDNAs and genomic clones (i.e., cognate nonhuman WBP1 or p53UBC genes) can be analogously isolated from various nonhuman cDNA and genomic clone libraries available in the art (e.g., Clontech, Palo Alto, Calif.) by using probes based on the sequences shown in FIG. 1A–1D (SEQ ID NO: 1) and FIG. 2 (SEQ ID NO: 3), with hybridization and washing conditions typically being less stringent than for isolation of human WBP1 or p53UBC clones.

Polynucleotides comprising sequences of approximately at least 30–50 nucleotides, preferably at least 100 nucleotides, corresponding to or complementary to the nucleotide sequences shown in FIGS. 1A–1D (SEQ ID NO:1) or FIG. 2 (SEQ ID NO:3) can serve as PCR primers and/or hybridization probes for identifying and isolating germline genes corresponding to WBP1 or p53UBC, respectively. These germline genes may be human or may be from a related mammalian species, preferably rodents or primates. Such germline genes may be isolated by various methods conventional in the art, including, but not limited to, by hybridization screening of genomic libraries in bacteriophage λ or cosmid libraries, or by PCR amplification of genomic sequences using primers derived from the sequences shown in FIGS. 1A–1D or FIG. 2. Human genomic libraries are publicly available or may be constructed de novo from human DNA.

Genomic clones of WBP1 or p53UBC, particularly of the murine cognate WBP1 or p53UBC gene, may be used to construct homologous targeting constructs for generating cells and transgenic nonhuman animals having at least one functionally disrupted WBP1 or p53UBC allele, preferably homozygous for knocked out WBP1 or p53UBC alleles. Guidance for construction of homologous targeting constructs may be found in the art, including: Rahemtulla et al. (1991) *Nature* 353: 180; Jasin et al. (1990) *Genes Devel.* 4: 157; Koh et al. (1992) *Science* 256: 1210; Molina et al. (1992) *Nature* 357: 161; Grusby et al. (1991) *Science* 253: 1417; Bradley et al. (1992) *Bio/Technology* 10: 534, incorporated herein by reference). Homologous targeting can be used to generate so-called "knockout" mice, which are heterozygous or homozygous for an inactivated WBP1 or p53UBC allele. Such mice may be sold commercially as research animals for investigation of apoptosis, neoplasia, cell proliferation, signal transduction, drug screening, and other uses.

Chimeric targeted mice are derived according to Hogan, et al., *Manipulating the Mouse Embryo: A Laboratory Manual*, Cold Spring Harbor Laboratory (1988) and *Teratocarcinomas and Embryonic Stem Cells: A Practical Approach*, E. J. Robertson, ed., IRL Press, Washington, D.C., (1987) which are incorporated herein by reference. Embryonic stem cells are manipulated according to published procedures (*Teratocarcinomas and Embryonic Stem Cells: A Practical Approach*, E. J. Robertson, ed., IRL Press, Washington, D.C. (1987); Zjilstra et al. (1989) *Nature* 342:435; and Schwartzberg et al. (1989) *Science* 246: 799, each of which is incorporated herein by reference).

Additionally, a WBP1 or p53UBC cDNA or genomic gene copy may be used to construct transgenes for expressing WBP1 or p53UBC polypeptides at high levels and/or under the transcriptional control of transcription control sequences which do not naturally occur adjacent to the WBP1 or p53UBC gene. For example but not limitation, a constitutive promoter (e.g., a HSV-tk or pgk promoter) or a cell-lineage specific transcriptional regulatory sequence (e.g., a CD4 or CD8 gene promoter/enhancer) may be operably linked to a WBP1- or p53UBC-encoding polynucleotide sequence to form a transgene (typically in combination with a selectable marker such as a neo gene expression cassette). Such transgenes can be introduced into cells (e.g., ES cells, hematopoietic stem cells, cultured primary hepatocytes) and transgenic cells and transgenic nonhuman animals may be obtained according to conventional methods. Transgenic cells and/or transgenic nonhuman animals may be used to screen for antineoplastic agents and/or to screen for potential cell proliferation modulating agents, as overexpression of WBP1 or p53UBC or inappropriate expression of WBP1 or p53UBC may result in a hyperproliferative state or hypoproliferative state.

Identification of Proteins That Bind WBP1 or p53UBC

Proteins that bind to WBP1 or p53UBC are potentially important regulatory proteins. Such proteins may be targets for novel therapeutic agents. These proteins are referred to herein as accessory proteins. For purposes of this invention, p53 is defined as not being an accessory protein of WBP1 or p53UBC, although p53 polypeptide sequences bind to WBP1 and p53UBC polypeptides in a yeast two-hybrid system. Accessory proteins may be isolated by various methods known in the art.

One preferred method of isolating accessory proteins is by contacting a WBP1 or p53UBC polypeptide to an antibody that binds the WBP1 or ps3UBC polypeptide, and isolating resultant immune complexes. These immune complexes may contain accessory proteins bound to the WBP1 or p53UBC polypeptide. The accessory proteins may be identified and isolated by denaturing the immune complexes with a denaturing agent and, preferably, a reducing agent. The denatured, and preferably reduced, proteins can be electrophoresed on a polyacrylamide gel. Putative accessory proteins can be identified on the polyacrylamide gel by one or more of various well known methods (e.g., Coomassie staining, Western blotting, silver staining, etc.), and isolated by resection of a portion of the polyacrylamide gel containing the relevant identified polypeptide and elution of the polypeptide from the gel portion.

A putative accessory protein may be identified as an accessory protein by demonstration that the protein binds to WBP1 or p53UBC protein. Such binding may be shown in vitro by various means, including, but not limited to, binding assays employing a putative accessory protein that has been renatured subsequent to isolation by a polyacrylamide gel electrophoresis method. Alternatively, binding assays employing recombinant or chemically synthesized putative accessory protein may be used. For example, a putative accessory protein may be isolated and all or part of its amino acid sequence determined by chemical sequencing, such as Edman degradation. The amino acid sequence information may be used to chemically synthesize the putative accessory protein. The amino acid sequence may also be used to produce a recombinant putative accessory protein by: (1) isolating a cDNA clone encoding the putative accessory protein by screening a cDNA library with degenerate oligonucleotide probes according to the amino acid sequence data, (2) expressing the cDNA in a host cell, and (3) isolating the putative accessory protein. Alternatively, a polynucleotide encoding a WBP1 or p53UBC polypeptide may be constructed by oligonucleotide synthesis, placed in an expression vector, and expressed in a host cell.

Putative accessory proteins that bind WBP1 and/or p53UBC in vitro are identified as accessory proteins. Accessory proteins may also be identified by crosslinking in vivo with bifunctional crosslinking reagents (e.g., dimethylsuberimidate, glutaraldehyde, etc.) and subsequent isolation of crosslinked products that include a WBP1 or p53UBC polypeptide. For a general discussion of crosslinking, see Kunkel et al. (1981) Mol. Cell. Biochem. 34: 3, which is incorporated herein by reference. Preferably, the bifunctional crosslinking reagent will produce crosslinks which may be reversed under specific conditions after isolation of the crosslinked complex so as to facilitate isolation of the accessory protein from the WBP1 or p53UBC polypeptide. Isolation of crosslinked complexes that include a WBP1 or p53UBC polypeptide is preferably accomplished by binding an antibody that binds a WBP1 or p53UBC polypeptide with an affinity of at least $1 \times 10^7$ M$^{-1}$ to a population of crosslinked complexes and recovering only those complexes that bind to the antibody with an affinity of at least $1 \times 10^7$ M$^{-1}$. Polypeptides that are crosslinked to a WBP1 or p53UBC polypeptide are identified as accessory proteins.

Screening assays can be developed for identifying candidate immunomodulatory agents as being agents which inhibit binding of WBP1 or p53UBC to an accessory protein under suitable binding conditions.

Expression of WBP1 and p53UBC Polypeptides

The nucleic acid sequences of the present invention capable of ultimately expressing the desired WBP1 or p53UBC polypeptides can be formed from a variety of different polynucleotides (genomic or cDNA, RNA, synthetic oligonucleotides, etc.) as well as by a variety of different techniques.

As stated previously, the DNA sequences will be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection markers, e.g., tetracycline resistance or hygromycin resistance, to permit detection and/or selection of those cells transformed with the desired DNA sequences (see, e.g., U.S. Pat. No. 4,704,362, which is incorporated herein by reference).

E. coli is one prokaryotic host useful particularly for cloning the DNA sequences of the present invention. Other microbial hosts suitable for use include bacilli, such as Bacillus subtilis, and other Enterobacteriaceae, such as Salmonella, Serratia, and various Pseudomonas species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. Saccharomyces is a preferred host, with suitable vectors having expression control sequences, such as promoters, including 3-phosphoglycerate kinase or other glycolytic enzymes, and an origin of replication, termination sequences and the like as desired.

In addition to microorganisms, mammalian tissue cell culture may also be used to express and produce the polypeptides of the present invention (see, Winnacker, "From Genes to Clones," VCH Publishers, N.Y., N.Y. (1987), which is incorporated herein by reference). Eukaryotic cells are actually preferred, because a number of suitable host cell lines capable of secreting intact human proteins have been developed in the art, and include the CHO cell lines, various COS cell lines, HeLa cells, myeloma cell lines, Jurkat cells, etc. Expression vectors for these cells can include expression control sequences, such as an origin of replication, a promoter, an enhancer (Queen et al. (1986) Immunol. Rev. 89: 49, which is incorporated herein by reference), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papillomavirus, and the like. The vectors containing the DNA segments of interest (e.g., polypeptides encoding a WBP1 or p53UBC polypeptide) can be transferred into the host cell by well-known methods, which vary depending on the type of cellular host. For example, CaCl transfection is commonly utilized for prokaryotic cells, whereas CaPO$_4$ treatment or electroporation may be used for other cellular hosts. (See, generally, Maniatis, et al., Molecular Cloning: A Laboratory Manual, Cold Spring Harbor Press, (1982), which is incorporated herein by reference). Usually, vectors are episomes and are maintained extrachromosomally.

Expression of recombinant WBP1 or p53UBC protein in cells, may be used to identify and isolate genes that are transcriptionally modulated, either positively or negatively, by the presence of WBP1 or p53UBC protein, either directly or via its interaction with p53. Such genes are typically initially identified as cDNA clones isolated from subtractive cDNA libraries, wherein RNA isolated from cells expressing recombinant WBP1 or p53UBC and RNA isolated from control cells (i.e., not expressing recombinant WBP1 or p53UBC) are used to generate the subtractive libraries and screening probes. In such a manner, WBP1- or p53UBC-dependent genes may be isolated. WBP1- or p53UBC-dependent genes (or their regulatory sequences operably linked to a reporter gene) may be used as a component of an in vitro transcription assay.

Methods for Forensic Identification

The WBP1 or p53UBC polynucleotide sequences of the present invention can be used for forensic identification of individual humans, such as for identification of decedents, determination of paternity, criminal identification, and the like. For example but not limitation, a DNA sample can be obtained from a person or from a cellular sample (e.g., crime scene evidence such as blood, saliva, semen, and the like) and subjected to RFLP analysis, allele-specific PCR, or PCR cloning and sequencing of the amplification product to determine the structure of the WBP1 or pS3UBC gene region. On the basis of the WBP1 or p53UBC gene structure, the individual from which the sample originated will be identified with respect to his/her WBP1 or p53UBC genotype. The WBP1 or p53UBC genotype may be used alone or in conjunction with other genetic markers to conclusively identify an individual or to rule out the individual as a possible perpetrator.

In one embodiment, human genomic DNA samples from a population of individuals (typically at least 50 persons from various racial origins) are individually aliquoted into reaction vessels (e.g., a well on a microtitre plate). Each aliquot is digested (incubated) with one or more restriction enzymes (e.g., EcoRI, HindIII, SmaI, BamHI, SalI, NotI, AccI, ApaI, BglII, XbaI, PstI) under suitable reaction conditions (e.g., see New England Biolabs or ProMega 1993 catalogs). Corresponding digestion products from each individual are loaded separately on an electrophoretic gel (typically agarose), electrophoresed, blotted to a membrane by Southern blotting, and hybridized with a labeled WBP1 or p53UBC probe (e.g., a sequence of FIGS. 1A–1D or FIG. 2). Restriction fragments (bands) which are polymorphic among members of the population are used as a basis to discriminate WBP1 or p53UBC genotypes and thereby classify individuals on the basis of their WBP1 or p53UBC genotype.

Similar categorization of WBP1 or p53UBC genotypes may be performed by sequencing PCR amplification products from a population of individuals and using sequence polymorphisms to identify alleles (genotypes), and thereby identify or classify individuals.

Yeast Two-Hybrid Screening Assays

Yeast two-hybrid systems may be used to screen a mammalian (typically human) cDNA expression library, wherein cDNA is fused to a GAL4 DNA binding domain or activator domain, and a WBP1 or p53UBC polypeptide sequence is fused to a GAL4 activator domain or DNA binding domain, respectively. Such a yeast two-hybrid system can screen for cDNAs encoding proteins which bind to WBP1 or p53UBC sequences. For example, a cDNA library can be produced from mRNA from a human cell line or other suitable cell type. Such a cDNA library cloned in a yeast two-hybrid expression system (Chien et al. (1991) *Proc. Natl. Acad. Sci. (U.S.A.)* 88: 9578; Zervos et al. (1993) *Cell* 72: 233) can be used to identify cDNAs which encode proteins that interact with WBP1 or p53UBC and thereby produce expression of the GAL4-dependent reporter gene. Polypeptides which interact with WBP1 or p53UBC can also be identified by immunoprecipitation of WBP1 or p53UBC with antibody and identification of co-precipitating species. Further, polypeptides that bind WBP1 or p53UBC can be identified by screening a peptide library (e.g., a bacteriophage peptide display library, a spatially defined VLSIPS peptide array, and he like) with a WBP1 or p53UBC polypeptide.

Methods for Rational Drug Design

WBP1 or p53UBC polypeptides, especially those portions which form direct contacts in p53 complexes, can be used for rational drug design of candidate p53-modulating gents (e.g., antineoplastics and p53 modulators). The substantially purified WBP1 or p53UBC protein and the identification of p53 as a docking partner for WBP1 and p53UBC as provided herein permits production of substantially pure WBP1:p53 and p53UBC:p53 polypeptide complexes and computational models which can be used for protein X-ray crystallography or other structure analysis methods, such as the DOCK program (Kuntz et al. (1982) *J. Mol. Biol.* 161: 269; Kuntz ID (1992) *Science* 257: 1078) and variants thereof. Potential therapeutic drugs may be designed rationally on the basis of structural information thus provided. In one embodiment, such drugs are designed to prevent formation of a WBP1:p53 or p53UBC:p53 polypeptide complexes. Thus, the present invention may be used to design drugs, including drugs with a capacity to inhibit binding of WBP1 or p53UBC to p53.

Methods of Identifying Novel p53-Modulating Agents

A basis of the present invention is the experimental finding that WBP1 and p53UBC polypeptides binds specifically to p53, a protein known to modulate cell proliferation in cells and which is known to be bound (sequestered) by viral-encoded oncogenic proteins. For example, agents which block p53 function and/or block WBP1 or p53UBC function may be developed as potential human therapeutic drugs.

Candidate therapeutic agents are then tested further for antineoplastic activity or cell proliferation enhancement activity in assays which are routinely used to predict suitability for use as human antineoplastic drugs. Examples of these assays include, but are not limited to: (1) ability of the candidate agent to inhibit the ability of anchorage-independent transformed cells to grow in soft agar, (2) ability to reduce tumorigenicity of transformed cells transplanted into nu/nu mice, (3) ability to reverse morphological transformation of transformed cells, (4) ability to reduce growth of transplanted tumors in nu/nu mice, (5) ability to inhibit formation of tumors or preneoplastic cells in animal models of spontaneous or chemically-induced carcinogenesis, and (6) ability to induce a more differentiated phenotype in transformed cells to which the agent is applied.

WBP1:p53 and p53UBC:p53 Intermolecular Binding

A basis of the present invention is the surprising finding that the WBP1 and p53UBC protein sequences form a complex with the p53 protein under physiological conditions. This finding indicates that the WBP1 and p53UBC proteins serve as a modulators of p53 function, and vice versa. Such functional modulation can serve to couple a signal transduction pathway (via WBP1 or p53UBC) to an cell proliferation regulatory protein (i.e., p53).

Assays for detecting the ability of agents to inhibit the binding of WBP1 or p53UBC to p53 provide for facile high-throughput screening of agent banks (e.g., compound libraries, peptide libraries, and the like) to identify WBP1 or p53UBC (or p53) antagonists or agonists. Such WBP1 or p53UBC (or p53) antagonists and agonists may modulate WBP1 or p53UBC (or p53) activity and thereby modulate cell proliferation and neoplasia.

Administration of an efficacious dose of an agent capable of specifically inhibiting WBP1:p53 or p53UBC:p53 complex formation or p53:p53 complex formation to a patient can be used as a therapeutic or prophylactic method for treating pathological conditions (e.g., cancer, inflammation, proliferative diseases, autoimmune disease, and the like) which are effectively treated by modulating WBP1 and/or pS3UBC and/or p53 activity and cell proliferation.

Binding assays generally take one of two forms: immobilized p53-interacting polypeptide(s) can be used to bind labeled p53 polypeptide(s), or conversely, immobilized p53 polypeptide(s) can be used to bind labeled WBP1 or p53UBC polypeptides. Alternatively, a binding assay can be performed to detect binding of a WBP1 or p53UBC polypeptide to form homodimers. Typically, a labeled WBP1 or pS3UBC polypeptide is contacted with an immobilized p53 polypeptide under aqueous binding conditions and the extent of binding is determined by measuring the amount of immobilized labeled p53. In each case, the labeled polypeptide is contacted with the immobilized polypeptide under aqueous conditions that permit specific binding of the polypeptides(s) to form a p53:p53-interacting polypeptide complex in the absence of added agent. Particular aqueous conditions may be selected by the practitioner according to conventional methods. For general guidance, the following buffered aqueous conditions may be used: 10–250 mM NaCl, 5–50 mM Tris HCl, pH 5–8, with optional addition of divalent cation(s) and/or metal chelators and/or nonionic detergents and/or membrane fractions. It is appreciated by those in the art that additions, deletions, modifications (such as pH) and substitutions (such as KCl substituting for NaCl or buffer substitution) may be made to these basic conditions. Modifications can be made to the basic binding reaction conditions so long as specific binding of WBP1 or p53UBC polypeptide(s) to p53 polypeptides occurs in the control reaction(s). In some embodiments, where the assay detects formation of homodimers, modifications can be made to the basic binding reaction conditions so long as specific binding of a WBP1, p53UBC, or p53 polypeptide to form homodimers occurs in the control reaction(s). Conditions that do not permit specific binding in control reactions (no agent included) are not suitable for use in binding assays.

Preferably, at least one polypeptide species is labeled with a detectable marker. Suitable labeling includes, but is not limited to, radiolabeling by incorporation of a radiolabeled amino acid (e.g., $^{14}$C-labeled leucine, $^{3}$H-labeled glycine, $^{35}$S-labeled methionine), radiolabeling by post-translational radioiodination with $^{125}$I or $^{131}$I (e.g., Bolton-Hunter reaction and chloramine T), labeling by post-translational phosphorylation with $^{32}$P (e.g., phosphorylase and inorganic radiolabeled phosphate) fluorescent labeling by incorporation of a fluorescent label (e.g., fluorescein or rhodamine), or labeling by other conventional methods known in the art. In embodiments where one of the polypeptide species is immobilized by linkage to a substrate, the other polypeptide is generally labeled with a detectable marker.

Additionally, in some embodiments a WBP1, p53UBC, or p53 polypeptide may be used in combination with an accessory protein (e.g., a protein which forms a complex with the polypeptide in vivo), it is preferred that different labels are used for each polypeptide species, so that binding of individual and/or heterodimeric and/or multimeric complexes can be distinguished. For example but not limitation, a WBP1 or p53UBC polypeptide may be labeled with fluorescein and an accessory polypeptide may be labeled with a fluorescent marker that fluroresces with either a different excitation wavelength or emission wavelength, or both. Alternatively, double-label scintillation counting may be used, wherein a WBP1 or p53UBC polypeptide is labeled with one isotope (e.g., $^{3}$H) and a second polypeptide species is labeled with a different isotope (e.g., $^{14}$C) that can be distinguished by scintillation counting using discrimination techniques.

Labeled polypeptide(s) are contacted with immobilized polypeptide(s) under aqueous conditions as described herein. The time and temperature of incubation of a binding reaction may be varied, so long as the selected conditions permit specific binding to occur in a control reaction where no agent is present. Preferable embodiments employ a reaction temperature of about at least 15 degrees Centigrade, more preferably 35 to 42 degrees Centigrade, and a time of incubation of approximately at least 15 seconds, although longer incubation periods are preferable so that, in some embodiments, a binding equilibrium is attained. Binding kinetics and the thermodynamic stability of bound p53:p53-interacting polypeptide complexes determine the latitude available for varying the time, temperature, salt, pH, and other reaction conditions. However, for any particular embodiment, desired binding reaction conditions can be calibrated readily by the practitioner using conventional methods in the art, which may include binding analysis using Scatchard analysis, Hill analysis, and other methods (*Proteins, Structures and Molecular Principles*, (1984) Creighton (ed.), W. H. Freeman and Company, New York).

Specific binding of labeled WBP1 or p53UBC polypeptide to immobilized p53 polypeptide, respectively, is determined by including unlabeled competitor protein(s) (e.g., albumin). After a binding reaction is completed, labeled polypeptide(s) that is/are specifically bound to immobilized polypeptide is detected. For example and not for limitation, after a suitable incubation period for binding, the aqueous phase containing non-immobilized protein is removed and the substrate containing the immobilized polypeptide species and any labeled protein bound to it is washed with a suitable buffer, optionally containing unlabeled blocking agent(s), and the wash buffer(s) removed. After washing, the amount of detectable label remaining specifically bound to the immobilized polypeptide is determined (e.g., by optical, enzymatic, autoradiographic, or other radiochemical methods).

In some embodiments, addition of unlabeled blocking agents that inhibit non-specific binding are included. Examples of such blocking agents include, but are not limited to, the following: calf thymus DNA, salmon sperm DNA, yeast RNA, mixed sequence (random or pseudorandom sequence) oligonucleotides of various lengths, bovine serum albumin, nonionic detergents (NP-40, Tween, Triton X-100, etc.), nonfat dry milk proteins, Denhardt's reagent, polyvinylpyrrolidone, Ficoll, and other blocking agents.

Practitioners may, in their discretion, select blocking agents at suitable concentrations to be included in binding assays; however, reaction conditions are selected so as to permit specific binding between a WBP1 or p53UBC polypeptide and a p53 polypeptide in a control binding reaction. Blocking agents are included to inhibit nonspecific binding of labeled protein to immobilized protein and/or to inhibit nonspecific binding of labeled polypeptide to the immobilization substrate.

In embodiments where a polypeptide is immobilized, covalent or noncovalent linkage to a substrate may be used. Covalent linkage chemistries include, but are not limited to, well-characterized methods known in the art (Kadonaga and Tijan (1986) *Proc. Natl. Acad. Sci. (U.S.A.)* 83: 5889, which is incorporated herein by reference). One example, not for limitation, is covalent linkage to a substrate derivatized with cyanogen bromide (such as CNBr-derivatized Sepharose 4B). It may be desirable to use a spacer to reduce potential steric hindrance from the substrate. Noncovalent bonding of proteins to a substrate include, but are not limited to, bonding of the protein to a charged surface and binding with specific antibodies.

In one class of embodiments, parallel binding reactions are conducted, wherein one set of reactions serves as control and at least one other set of reactions include various quantities of agents, mixtures of agents, or biological extracts, that are being tested for the capacity to inhibit binding of a p53-interacting polypeptide to a p53 polypeptide, and/or to inhibit binding of a WBP1, p53UBC, or p53 polypeptides to form homomultimers (homodimers).

The following examples are offered by way of example and not by way of limitation. Variations and alternate embodiments will be apparent to those of skill in the art.

EXPERIMENTAL EXAMPLES

EXAMPLE 1. Determination of the nucleotide and deduced amino acid sequence of human cDNAs encoding P53-binding proteins This example describes the identification of human cDNAs that encode p53-binding proteins active in a yeast two-hybrid screening system.

Cloned polynucleotides were isolated from a yeast two-hybrid screening system comprising a polynucleotide encoding a human p53 polypeptide sequence fused to a GAL4 DNA-binding domain and a polynucleotide encoding a human cDNA library sequence fused to activation domain. The yeast two hybrid system contained (1) a cDNA library derived from HeLa cells that had been cloned into the GAL4 plasmid PGAD, described in Chien et al. (1991) op.cit and (2) a polynucleotide sequence encoding a human p53 polypeptide spanning from amino acid 72 to amino acid 393 of a wild-type human p53 polypeptide sequence cloned into the GAL4 plasmid pGBT8, described in Freed et al. (1994) *Science* 265: 1713.

Colonies were identified as positive by growth on minimal medium containing adenine and lacking tryptophan, leucine, and histidine. Positive colonies were selected and the polynucleotide sequence of the cDNA insert was isolated. For WBP1, the cDNA insert was isolated by digestion with EcoRI and XhoI, the EcoRI/XbaI fragment cloned into pBluescript, and sequenced by Sanger dideoxy sequencing. For p53UBC, the cDNA insert was isolated by digestion with BamHI and SmaI, the BamHI/SmaI fragment cloned into pBluescript, and sequenced by Sanger dideoxy sequencing.

Two positive clones were isolated and sequenced.

WBP1

One clone, designated clone 85 (WBP1), specifically binds a conformationally wild-type human p53 and substantially lacks binding to mutant p53 proteins that have a pAb240 epitope. The pAB240 monoclonal antibody specifically recognizes a common conformational change found in many mutant p53 polypeptides. Wild-type human p53 comprised amino acids 72–393 of human p53, and mutant human p53 comprised that sequence with a point mutation at amino acid #141 (Cys→Arg) or at amino acid #175 (Arg→His).

The nucleotide and deduced amino acid sequences of WBP1 are shown in FIGS. 1A–1D. A region of 152 amino acids encoded by clone WBP1 was found to be sufficient to bind wild-type human p53 in vitro. Full-length WBP1 and various deletions were transcribed and translated in vitro in the presence of $^{35}$S-methionine and mixed with wild-type p53 (purified from a baculovirus expression system). The mixture was incubated at 4° C. for three hours, whereupon a monoclonal antibody (pAB421) that binds p53 and Protein A-Sepharose beads were added, and the incubation was continued for an additional hour at 4° C. The Protein A-Sepharose immune complexes were recovered and washed three times with 20 mM Tris (pH 8.0), 150 mM NaCl, 0.1% NP-40, and dissolved in SDS-gel sample buffer for SDS-PAGE. The samples were resolved on an 11 percent polyacrylamide gel containing SDS. Interaction with p53 was scored by the ability of the p53-specific monoclonal antibody pAB421 to immunoprecipitate the WBP1 polypeptide being tested. These experiments demonstrated that a 152 amino acid segment of the WBP1 protein (encoded by the approximately 450 nucleotide PstI fragment) was sufficient to confer the property of binding to p53 in vitro. This fragment has the sequence:

ELPHLTSALHPVHPDIKLQKLPFYDLLDELIKPTSLASDNSQRFRETCFAFALTPQQVQQ (SEQ ID NO:103)

ISSSMDISGTKCDFTVQVQLRFCLSETSCPQEDHFPPNLCVKVNTKPCSLPGYLPPTKNG

VEPKRPSRPINITSLVRLSTTVPNTIVVSWTA.

Sequence analysis of WBP1 revealed partial identity with HFBDQ46 (*Nature Genetics* (1993) 4: 256), a randomly isolated 351 bp cDNA of unknown function obtained for use as a genetic marker (i.e., an expressed sequence tag). The segment of WBP1 spanning from nucleotide 201 to nucleotide 599 was aligned to the complete sequence of HFBDQ46 (designated T06215) and is shown below (top sequence is WBP1(SEQ. ID NO: 120), bottom sequence is HFBDQ46(SEQ. ID NO:121):

```
201 CACAGAAAATCATGACGCCTGCAGACTTGTCCATCCCCAACGTACATTCA 250
                          | |||||||||||||||||||||||||||
1   .....................CTGACTTGTCCATCCCCAACGTACATTCA 29

251 AGTCCTATGCCAGCAACTTTGTCTCCATCTACCATTCCACAACTCACTTA 300
    ||||||||||||||||||||||||||||||||||||||||||||||||||
30  AGTCCTATGCCAGCAACTTTGTCTCCATCTACCATTCCACAACTCACTTA 79

301 CGATGGTCACCCTGCATCATCGCCATTACTCCCTGTTTCTCTTCTGGGAC 350
    ||||||||||||||||||||||||||||||||||||||||||||||||||
80  CGATGGTCACCCTGCATCATCGCCATTACTCCCTGTTTCTCTTCTGGGAC 129

351 CTAAACATGAACTGGAACTCCCACATCTTACATCAGCTCTTCACCCAGTC 400
    ||||||||||||||||||||||||||||||||||||||||||||||||||
130 CTAAACATGAACTGGAACTCCCACATCTTACATCAGCTCTTCACCCAGTC 179

401 CATCCGGATATAAAACTTCAAAAATTACCATTTTATGATTTACTGGATGA 450
    ||||||||||||||||||||||||||||||||||||||||||||||||||
180 CATCCGGATATAAAACTTCAAAAATTACCATTTTATGATTTACTGGATGA 229

451 ACTGATAAAACCCACCAGTCTAGCATCAGACAACAGTCAGCGCTTTCGAG 500
    ||||||||||||||||||||||||||||||||||||||||||||||||||
230 ACTGATAAAACCCACCAGTCTAGCATCAGACAACAGTCAGCGCTTTCGAG 279

501 AAACCTGTTTTGCATTTGCCTTGACACCACAACAAG.TGCAGCAAATCAG 549
    |||||||||||||||||||||||||||||||||||| :||||||||||||
280 AAACCTGTTTTGCATTTGCCTTGACACCACAACAAGTNGCAGCAAATCAG 329

550 TAGTTCCATGGATATTTCTGGGACCAAATGTGACTTCACAGTACAGGTCC 599
    |||||||||||| |||||||||||
330 TAGTTCCATGGGTATTTCTGGG............................ 351
```

The deduced amino acid sequence of WBP1 was used to search the GenBank data base for other polynucleotides encoding homologous (i.e., related sequence) polypeptides. No significant homologies were found.

pS3UBC

One positive clone, designated clone 75A (p53UBC) was isolated. p53UBC binds to a carboxy-terminal portion of human p53 (aa72 to aa393). The p53UBC polypeptide binds both wild-type and mutant p53 polypeptides, with a slight preference for binding to wild-type p53 (described supra), as determined in a yeast two-hybrid system.

The p53UBC clone was sequenced and the nucleotide sequence and deduced amino acid sequences are shown in FIG. 2. Sequence analysis of p53UBC revealed that the encoded polypeptide sequence has significant homology to certain ubiquitin conjugating enzymes. Ubiquitin conjugating enzymes have been reported to be involved in mediating degradation of certain intracellular proteins (Chen et al. (1993) Cell 74: 357).

Although the present invention has been described in some detail by way of illustration for purposes of clarity of understanding, it will be apparent that certain changes and modifications may be practiced within the scope of the claims.

We claim:

1. An isolated WBP1 polypeptide comprising a polypeptide sequence shown in SEQ ID NO:1.

2. An isolated WBP1 polypeptide comprising a polypeptide sequence having at least a 95% sequence identity to SEQ. ID NO. 1 of claim 1, wherein said polypeptide specifically binds to p53.

3. An isolated WBP1 polypeptide comprising a polypeptide sequence having at least a 99% sequence identify to SEQ. ID NO. 1 of claim 1, wherein said polypeptide specifically binds to p53.

4. An isolated WBP1 polypeptide fragment having SEQ. ID NO. 102.

5. An isolated WBP1 polypeptide fragment having SEQ. ID NO. 103.

6. An isolated WBP1 polypeptide fragment having SEQ. ID NO. 122.

7. An isolated WBP1 polypeptide fragment having at least a 95% sequence identity to a WBP1 polypeptide fragment selected from the group consisting of SEQ. ID NO. 102, SEQ. ID NO. 103, or SEQ. ID NO. 122, wherein said polypeptide specifically binds to p53.

8. A mammalian or prokaryotic host cell comprising an isolated WBP1 polypeptide having SEQ. ID NO. 1.

9. A mammalian or prokaryotic host cell comprising an isolated WBP1 polypeptide of claims 3 or 4.

10. A mammalian or prokaryotic host cell comprising the isolated peptide fragments of claim 7.

11. An isolated polynucleotide that encodes WBP1 comprising SEQ. ID NO. 2.

12. An isolated polynucleotide having at least 95% identity to the polynucleotide of claim 11.

13. An isolated polynucleotide having at least 99% identity to the polynucleotide of claims 11.

14. A mammalian or prokaryotic host cell comprising the isolated polynucleotide of claim 11.

15. A mammalian or prokaryotic host cell comprising the isolated polynucleotide of claim 12.

* * * * *